US010006060B2

(12) United States Patent
Ramaen et al.

(10) Patent No.: US 10,006,060 B2
(45) Date of Patent: Jun. 26, 2018

(54) SELECTIVITY OF THE PRODUCTION OF VANILLOIDS IN A RECOMBINANT UNICELLULAR HOST

(71) Applicant: Rhodia Operations, Paris (FR)

(72) Inventors: Odile Ramaen, Ablis (FR); Rudy Pandjaitan, Maisons-Alfort (FR); Mirjana Gelo-Pujic, Serezin-sur-Rhone (FR)

(73) Assignee: RHODIA OPERATIONS, Paris (FR)

( * ) Notice: Subject to any disclaimer, the term of this patent is extended or adjusted under 35 U.S.C. 154(b) by 0 days. days.

(21) Appl. No.: 15/319,120

(22) PCT Filed: Jun. 17, 2015

(86) PCT No.: PCT/EP2015/063590
§ 371 (c)(1),
(2) Date: Dec. 15, 2016

(87) PCT Pub. No.: WO2015/193371
PCT Pub. Date: Dec. 23, 2015

(65) Prior Publication Data

US 2017/0114373 A1 Apr. 27, 2017

(30) Foreign Application Priority Data

Jun. 18, 2014 (EP) .................................... 14305936

(51) Int. Cl.

| | |
|---|---|
| ***C07C 45/58*** | (2006.01) |
| ***C12P 7/00*** | (2006.01) |
| ***C12P 9/00*** | (2006.01) |
| ***C12P 7/24*** | (2006.01) |
| ***C12N 15/52*** | (2006.01) |
| ***C12N 9/10*** | (2006.01) |
| ***C12N 9/12*** | (2006.01) |
| ***C12N 9/88*** | (2006.01) |
| ***C12N 9/02*** | (2006.01) |
| ***C07C 47/58*** | (2006.01) |

(52) U.S. Cl.
CPC ................ *C12P 7/24* (2013.01); *C07C 47/58* (2013.01); *C12N 9/0008* (2013.01); *C12N 9/1007* (2013.01); *C12N 9/1288* (2013.01); *C12N 9/88* (2013.01); *C12N 15/52* (2013.01); *C12Y 102/0103* (2013.01); *C12Y 201/01068* (2013.01); *C12Y 207/08007* (2013.01); *C12Y 402/01118* (2013.01)

(58) Field of Classification Search
CPC ......... C07C 45/58; C12P 7/24; C12N 9/0008; C12N 9/1007; C12N 9/1288; C12N 15/52; C12Y 102/0103; C12Y 201/01068; C12Y 402/01118
USPC .......................................................... 568/442
See application file for complete search history.

(56) References Cited

FOREIGN PATENT DOCUMENTS

WO 2004/036979 A2 5/2004
WO 2013/022881 A1 2/2013

OTHER PUBLICATIONS

Hansen et al.; "De Novo Biosynthesis of Vanillinin Fission Yeast (*Schizosaccharomyces pombe*) and Baker's Yeast (*Saccharomyces cerevisiae*)"; Applied and Environmental Microbiology, vol. 75, No. 1, May 2009, pp. 2765-2774.
Brochado et al.; "Improved vanillin production in baker's yeast through in silico design"; Microbial Cell Factories, vol. 9, No. 84, Nov. 8, 2010, pp. 1-15.

*Primary Examiner* — Sikarl A Witherspoon
(74) *Attorney, Agent, or Firm* — Whitham, Curtis & Cook, P.C.

(57) ABSTRACT

The present invention relates to methods for producing vanilloid compounds in a recombinant host, and in particular for converting a protocatechuic aldehyde into a substantially pure vanilloid. It further relates to novel yeast strains that are suitable for producing such vanilloid compounds.

23 Claims, 7 Drawing Sheets

SELECTIVITY OF THE PRODUCTION OF VANILLOIDS IN A RECOMBINANT UNICELLULAR HOST

FIELD OF THE INVENTION

The present invention relates to methods for producing vanilloid compounds in a recombinant host, and in particular for converting a protocatechuic aldehyde into a substantially pure vanilloid. It further relates to novel yeast strains that are suitable for producing such vanilloid compounds.

BACKGROUND OF THE INVENTION

Vanilloids (also referred herein as "vanilloid compounds") are defined as chemical compounds derived from a vanillyl group, the latter being formed by a benzyle group substituted with a hydroxyle and a methoxy group, and whose chemical structure is shown here below:

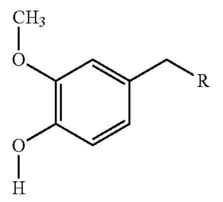

wherein R is generally selected from the group consisting of H, a lower alkyl such as a methyl ($—CH_3$) or an ethyl ($—CH_2CH_3$), an aldehyde and a carboxylic acid. Optionally, the —OH group is substituted with an O-glycosyl group.

In a non-limitative manner, vanilloids include vanillyl alcohol, vanillin, vanillic acid, vanillin-glycoside, acetovanillon, vanillylmandelic acid, homovanillic acid, and capsaicidoids such as capsaicin.

Among vanilloids, vanillin of chemical name 4-hydroxy-3-methoxybenzaldehyde is one of the most important aromatic flavor compound used in foods, beverages, fragrance, pharmaceuticals and polymers. Vanillin was historically extracted from *Vanilla planifolia, Vanilla tahitiensis* and *Vanilla pompona* pods. The demand getting higher, today, less than 5% of worldwide vanillin production comes from natural *vanilla* pods. Currently, chemical synthesis is the most important process for producing vanillin.

There is a growing interest in other sources of vanillin and in particular in bioconversion processes. The use of microbial cells and their enzymes as biocatalysts for the synthesis of chemicals and flavor compounds have attracted much attention lately. Advantageously, under certain criteria, the products of such bioconversion may be considered 'natural' by legislations, such as the European Community one.

Bioconversion processes are based on the following substrates: lignin, phenolic stilbenes, isoeugenol, eugenol, ferulic acid, sugars, phenolic stilbenes, waste residues and aromatic amino acids. The recent review from Kaur and Chakraborty (Kaur B, Chakraborty D. "*Biotechnological and molecular approaches for vanillin production: a review.*" Appl Biochem Biotechnol. 2013 February; 169(4): 1353-72) lists several biosynthetic pathways and appropriate cells used for bioconversion of vanilloids.

De novo synthesis from glucose using metabolically engineered yeast strains has been recently described (Hansen et al., De Novo Biosynthesis of Vanillin in Fission Yeast (*Schizossacharomyces pombe*) and Baker's Yeast (*Saccharomyces cerevisae*); Appl. Environ. Microbiol. 2009, 75(9): 2765). The engineered pathway involves a 3-dehydroshikimate dehydratase (3DSD), an aromatic carboxylic acid reductase (ACAR) and an O-methyltransferase (COMT), as shown in FIGS. 1 and 2 (see in particular FIG. 2, and pathways "1" and "2"), which relate to the global reaction scheme of vanillin biosynthesis from glucose. In *S. cerevisiae*, the ACAR enzyme requiring activation mediated by a phosphopantetheinyl transferase, this enzyme was also introduced.

So far, studies related to recombinant unicellular hosts capable of producing vanilloids had mostly focused on the use of O-methyltransferases of the catechol methyltransferase type (EC 2.1.1.6; CAS no 9012-25-3), which are known to catalyze the methylation of catechol into guaiacol. The catechol O-methyltransferase accepts flavanols like epicatechin and epigallocatechin, catecholamines like L-DOPA and adrenalin, 3,4-dihydroxyphenylacetic acid, caffeic acid as substrates.

Later, the same authors improved their pathway by using mutants of human catechol acid O-methyltransferase having a better specificity, thereby limiting the production of iso-vanillin (WO 2013/022881).

Other improvements of vanillin biosynthesis pathway have been proposed, and in particular:

- Alcohol dehydrogenases ADH6 & ADH7 are known to convert vanillin into its corresponding vanillyl alcohol. Studies have suggested the deletion of the adh6 gene in vanillin-producing yeasts (Hansen et al., 2009).
- Brochado (Brochado et al., 2010) suggested the deletion of genes encoding pyruvate decarboxylase (PDC1) and glutamate dehydrogenase (GDH1), since the deletion of these genes increases the availability of co-factors (ATP, NADPH . . . ) for the biosynthesis pathway of vanilloids.
- Most of phenolic compounds such as vanillin show some toxicity for many living organisms with increased concentration of vanilloids. In case of *Saccharomyces cerevisiae*, growth defect is significant with concentrations as low as 0.5 g/l. To avoid the impaired growth of producing microorganisms, it has also been proposed to isolate the produced vanilloids from the culture medium, in particular with resins. Another suggested solution is promoting conversion of vanillin into vanillin β-D-glucoside, this glycosylation inhibiting its toxic effect (Hansen et al., 2009; Brochado et al., 2010).

For comprehension purposes, FIGS. 2A and 2B summarizes the three main vanillin biosynthesis pathways. According to the invention, pathway "1" and pathway "2" are part of the "dehydroshikimic acid pathway". Within said dehydroshikimic acid pathway, pathway "1" represents a first alternative route and will be referred herein as the "AAD-dependent dehydroshikimic acid pathway". Pathway "2" represents a second alternative route, and will be referred herein as the "ACAR-dependent dehydroshikimic acid pathway".

The term "3-dehydroshikimic acid" also called 3-DHS designates the compound of the systemic name (4S,5R)-4,5-D-dihydroxy-3-oxocyclohexene-1-carboxylic acid.

Another pathway for producing a vanilloid in yeast is inspired from the natural biosynthesis pathway observed in the *Vanilla planifolia* orchid, such as the one described in patent application US 2003/0070188. This pathway, shown in FIG. 2 (pathway "3"), uses aromatic amino acids such as phenylalanine and tyrosine as primary substrates.

The term "aromatic amino acids" designates amino acids that include an aromatic ring. Among the twenty standard amino acids, four of them are aromatic: phenylalanine, tryptophan, histidine and tyrosine.

However, even if these pathways are effective for producing vanilloids in recombinant hosts such as yeasts, they do not allow a sufficient production of these compounds for being industrialized. Different propositions have been made to improve the production of vanilloids by fermentation in cells.

The production of vanillin in metabolically engineered yeast strains is hindered by the production of other vanilloids which may be undesirable, or to the least less desirable because of, for instance, a lack of pronounced aromatic flavor. In particular, the production of vanillin in *S. pombe* leads to the production of different sorts of vanilloid compounds such as vanillin, isovanillin, vanillyl alcohol, isovanillic acids and/or vanillic acids (see Hansen et al., 2009). Indeed isovanillin and isovanillic acids are closely related compounds which may be produced in large amounts during the production of Vanillin involving O-methyltransferases. Such production in the recombinant host is problematic, because isovanillin does not share the same aromatic properties as its counterpart.

Unfortunately, the ratio vanillin/isovanillin which is obtained using currently available engineered yeast strains is equal or inferior to 125:1, which means that those pathways are not 100% selective for vanillin production.

Thus, there remains a need for novel methods for producing vanilloid compounds in a recombinant unicellular host.

There also remains a need for improving the production of vanilloid compounds, and decreasing the production of isovanillin.

There also remains a need for improving selectivity of this production in a recombinant unicellular host such as yeast towards vanilloid compounds of interest, such as vanillin.

Thus there also remains a need for producing a substantially pure vanilloid compound with a recombinant unicellular host.

SUMMARY OF THE INVENTION

The invention relates to a method for producing a substantially pure vanilloid of formula (I):

(I)

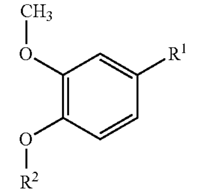

$R^1$ being selected from the group consisting of —CHO; —COOH; —COOR$^3$; —$CH_2OH$; —$CH_2COOH$; —C(═O)$CH_3$; —CR$^3$(OH)COOH; —CHR$^3$COOH; —$CH_2$NHC(═O)R$^3$; wherein $R^3$ is a lower alkyl, $R^2$ being different from a methyl (—$CH_3$), and being preferably selected from the group consisting of H, a sulfate, a phosphate and a glycoside, comprising the steps of:

a) providing a recombinant unicellular host capable of producing said vanilloid, wherein said recombinant host expresses at least a nucleic acid coding for a 3-dehydroshikimate dehydratase (3DSD) and at least a nucleic acid coding for an aromatic carboxylic acid reductase (ACAR);

b) cultivating said host in a suitable medium; and c) recovering the produced vanilloid from said host or from the culture supernatant thereof, wherein said recombinant host expresses at least a nucleic acid coding for a caffeic acid 3-O-methyltransferase polypeptide that is suitable for methylating selectively the 3-OH of a protocatechuic aldehyde, in particular for a caffeic acid O-methyltransferase polypeptide from *Medicago sativa, Rosa chinensis*, or *Vanilla planifolia.*

The invention further relates to a yeast suitable for producing a substantially pure vanilloid of formula (I):

(I)

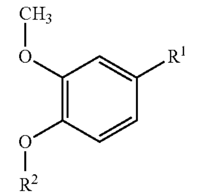

$R^1$ being selected from the group consisting of —CHO; —COOH; —COOR$^3$; —$CH_2OH$; —$CH_2COOH$; —C(═O)$CH_3$; —CR$^3$(OH)COOH; —CHR$^3$COOH; —$CH_2$NHC(═O)R$^3$; wherein $R^3$ is a lower alkyl, $R^2$ being different from a methyl (—$CH_3$), and being preferably be selected from the group consisting of H, a sulfate, a phosphate and a glycoside, and expressing at least a nucleic acid coding for an aromatic carboxylic acid reductase (ACAR) and a 3-dehydroshikimate dehydratase (3DSD), wherein said yeast expresses at least a nucleic acid coding for a caffeic acid 3-O-methyltransferase polypeptide that is suitable for methylating selectively the 3-OH of a protocatechuic aldehyde, in particular a caffeic acid 3-O-methyltransferase polypeptide from *Medicago sativa, Rosa chinensis*, or *Vanilla planifolia.*

The invention also relates to methods and recombinant hosts for production of a substantially pure vanilloid through any biosynthetic pathway comprising an aromatic carboxylic acid reductase (ACAR) and a caffeic acid 3-O-methyltransferase polypeptide that is suitable for methylating selectively the 3-OH of a protocatechuic aldehyde, except for the aromatic acid-dependent pathway, i.e. "pathway 3" as shown in FIG. 2B.

Thus, the invention also relates to a recombinant cellular host, preferably a yeast, suitable for producing a substantially pure vanilloid of formula (I):

(I)

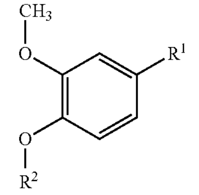

$R^1$ being selected from the group consisting of —CHO; —COOH; —COOR$^3$; —$CH_2OH$; —$CH_2COOH$; —C(═O)$CH_3$; —CR$^3$(OH)COOH; —CHR$^3$COOH; —$CH_2$NHC(═O)R$^3$; wherein $R^3$ is a lower alkyl, $R^2$ being different from a methyl (—$CH_3$), expressing at least a nucleic acid coding for an aromatic carboxylic acid reductase (ACAR), wherein said yeast expresses at least a nucleic acid coding for a caffeic acid 3-O-methyltransferase polypeptide that is suitable for methylating selectively the 3-OH of a protocatechuic aldehyde, and does not express nucleic acids coding for the following enzymes: a phenylalanine ammonia lyase (PAL) or a tyrosine ammonia lyase (TAL) or a phenylalanine/tyrosine ammonia lyase (PAL/TAL), a coA ligase, and a crotonase.

Thus the invention also relates to a method for converting a protocatechuic aldehyde into a substantially pure vanilloid of formula (I):

(I)

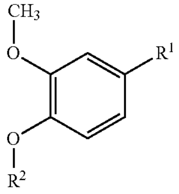

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, $R^2$ being different from a methyl (—$CH_3$), and comprising the steps of:

a) providing a recombinant unicellular host capable of producing said vanilloid, wherein said recombinant host expresses at least a nucleic acid coding for an aromatic carboxylic acid reductase (ACAR) and does not express nucleic acids coding for the following enzymes: a phenylalanine ammonia lyase (PAL) or a tyrosine ammonia lyase (TAL) or a phenylalanine/tyrosine ammonia lyase (PAL/TAL), a coA ligase, and a crotonase;

b) cultivating said host in a suitable medium; and c) recovering the produced vanilloid from said host or from the culture supernatant thereof, wherein said recombinant host expresses at least a nucleic acid coding for a caffeic acid 3-O-methyltransferase polypeptide that is suitable for methylating selectively the 3-OH of a protocatechuic aldehyde, in particular for a caffeic acid O-methyltransferase polypeptide from *Medicago sativa, Rosa chinensis*, or *Vanilla planifolia*.

The invention also relates to a method for converting a protocatechuic aldehyde into a substantially pure vanilloid of formula (I):

(I)

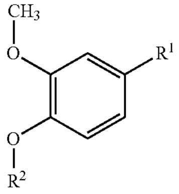

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, $R^2$ being different from a methyl (—$CH_3$), and comprising the steps of:

a) providing a recombinant unicellular host capable of producing said vanilloid, wherein said recombinant host expresses at least a nucleic acid coding for an aromatic carboxylic acid reductase (ACAR) and at least a nucleic acid coding for a 3-dehydroshikimate dehydratase (3DSD);

b) cultivating said host in a suitable medium; and c) recovering the produced vanilloid from said host or from the culture supernatant thereof, wherein said recombinant host expresses at least a nucleic acid coding for a caffeic acid 3-O-methyltransferase polypeptide that is suitable for methylating selectively the 3-OH of a protocatechuic aldehyde, in particular for a caffeic acid O-methyltransferase polypeptide from *Medicago saliva, Rosa chinensis*, or *Vanilla planifolia*.

The invention also relates to a yeast suitable for converting a protocatechuic aldehyde into a substantially pure vanilloid of formula (I)

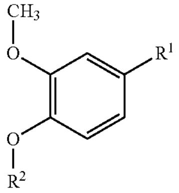

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, $R^2$ being different from a methyl (—$CH_3$), expressing at least a nucleic acid coding for an aromatic carboxylic acid reductase (ACAR), wherein said yeast expresses at least a nucleic acid coding for a caffeic acid 3-O-methyltransferase polypeptide that is suitable for methylating selectively the 3-OH of a protocatechuic aldehyde, and does not express nucleic acids coding for the following enzymes: a phenylalanine ammonia lyase (PAL) or a tyrosine ammonia lyase (TAL) or a phenylalanine/tyrosine ammonia lyase (PAL/TAL), a coA ligase, and a crotonase.

The invention also relates to a yeast suitable for converting a protocatechuic aldehyde into a substantially pure vanilloid of formula (I):

(I)

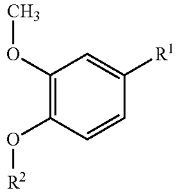

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, $R^2$ being different from a methyl (—$CH_3$), expressing at least a nucleic acid encoding an aromatic carboxylic acid reductase (ACAR) and at least a nucleic acid coding for a 3-dehydroshikimate dehydratase (3DSD), wherein said yeast expresses at least a nucleic acid coding for a caffeic acid 3-O-methyltransferase polypeptide that is suitable for methylating selectively the 3-OH of a protocatechuic aldehyde.

In addition, the present invention further relates to a composition comprising a vanilloid such as obtainable by the methods as disclosed above, and to the use of said composition as a flavoring in the human and animal nutrition field, in pharmacy, and as a fragrance in the cosmetics, perfumery and detergency industries.

DESCRIPTION OF THE INVENTION

Figure 1:
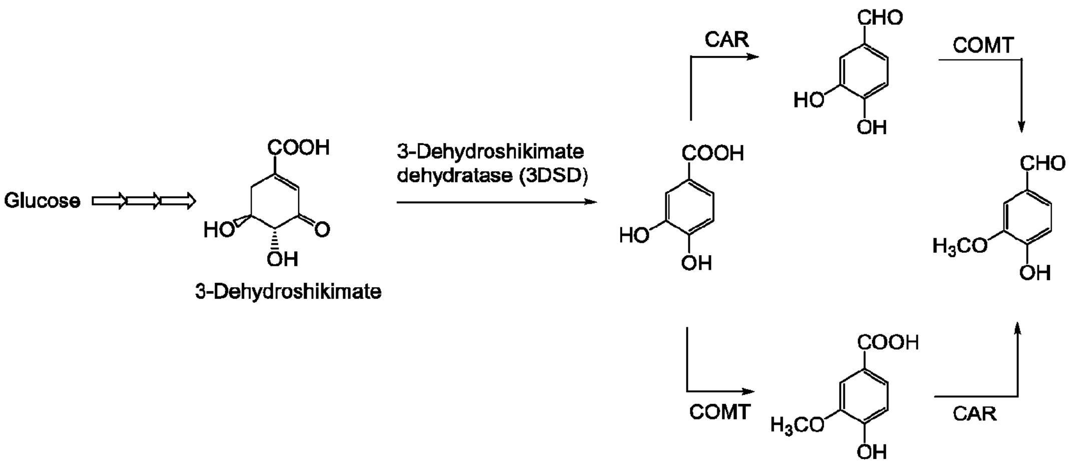
FIG. 1: Close view of part the shikimic acid pathway of vanillin biosynthesis in metabolically engineered microorganisms. CAR relates to an enzyme with carboxylic acid reductase activity and COMT relates to an enzyme with a 3-O-methyltransferase activity, such as a catechol 3-O-methyltransferase or a caffeic acid 3-O-methyltransferase.

The invention has for purpose to meet the aforementioned needs.

According to the invention, the terms "biosynthesis", "bioconversion" "fermentative production" and "production" have the same meaning, and designate the production of at least one vanilloid by a recombinant unicellular host, such as a yeast, when cultivated in appropriate conditions.

Thus, the invention relates to methods for producing vanilloid compounds in a recombinant unicellular host.

The present invention relates to a method for producing a substantially pure vanilloid of formula (I):

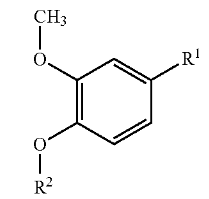

(I)

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, $R^2$ being different from a methyl (—$CH_3$), comprising the steps of:

a) providing a recombinant unicellular host capable of producing said vanilloid, wherein said recombinant host expresses at least a nucleic acid coding for a 3-dehydroshikimate dehydratase (3DSD) and at least a nucleic acid coding for an aromatic carboxylic acid reductase (ACAR);

b) cultivating said host in a suitable medium; and c) recovering the produced vanilloid from said host or from the culture supernatant thereof, wherein said recombinant host expresses at least a nucleic acid coding for a caffeic acid O-methyltransferase polypeptide that is suitable for methylating selectively the 3-OH of a protocatechuic aldehyde, in particular for a caffeic acid O-methyltransferase polypeptide from *Medicago sativa, Rosa chinensis*, or *Vanilla planifolia*, and more preferably from *Medicago sativa* or *Rosa chinensis.*

According to the most preferred embodiment, a recombinant host of the invention expresses at least a caffeic acid 3-O-methyltransferase polypeptide from *Medicago sativa.*

Thus, the invention relates to a method for producing a substantially pure vanilloid of formula (I):

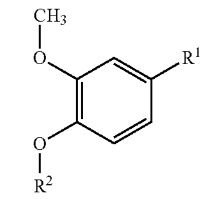

(I)

$R^1$ being selected from the group consisting of —CHO; —COOH; —$COOR^3$; —$CH_2OH$; —$CH_2COOH$; —C(═O)

$CH_3$; $—CR^3(OH)COOH$; $—CHR^3COOH$; $—CH_2NHC(=O)R^3$; wherein $R^3$ is a lower alkyl, $R^2$ being different from a methyl ($—CH_3$), comprising the steps of:

a) providing a recombinant unicellular host capable of producing said vanilloid, wherein said recombinant host expresses at least a nucleic acid coding for a 3-dehydroshikimate dehydratase (3DSD) and at least a nucleic acid coding for an aromatic carboxylic acid reductase (ACAR);

b) cultivating said host in a suitable medium; and c) recovering the produced vanilloid from said host or from the culture supernatant thereof, wherein said recombinant host expresses at least a nucleic acid coding for a caffeic acid 3-O-methyltransferase polypeptide from *Medicago sativa.*

According to the invention, a recombinant host «expressing at least a O-methyltransferase polypeptide» encompasses a recombinant host having a gene encoding a functional O-methyltransferase.

According to the invention, a «gene» relates to an exogenous or endogenous nucleic acid sequence comprising a promoter and a coding sequence, so that in said host, the polypeptide(s), and/or product(s) of said nucleic acid sequence(s), are expressed.

Most preferably, each nucleic acid encoding a polypeptide as described herein comprises, from its 5' end to its 3' end, (i) a regulatory sequence comprising one or more promoter sequences, the said regulatory sequence being functional in the recombinant host wherein it has been introduced, (ii) an Open Reading Frame (ORF) encoding a polypeptide of interest and (iii) one or more transcription terminator sequences.

In the sense of the present invention, it is understood that exogenous nucleic acids encoding polypeptides that are introduced into a recombinant unicellular host, such as yeasts, are "codon-optimized" to be expressed efficiently. The man skilled in the art knows some 'Codon Optimization Tools' that allow the preparation of synthetic genes from one host organism for an optimized expression in another, in particular in the yeast according to the invention.

Exogenous nucleic acids encoding the heterologous polypeptides are introduced into the host by transformation and this manipulation results into incorporation and expression of exogenous genetic material. Transformation of a host such as yeast can be performed by means well known by the man skilled in the art: yeast cells may be treated with enzymes to degrade their cell walls, or they may be exposed to alkali cations such as lithium acetate, or to polyethylene glycol. Electroporation using electric shock is also a technique that allows exogenous DNA to enter into yeasts. Some of those useful techniques are reviewed in Kawai et al., 2010.

In a preferred embodiment of the invention, transformations of a recombinant hosts such as competent yeast cells are performed as described by Gietz and Woods (*Transformation of yeast by the LiAc/ss Carrier DNA/PEG method.* Meth. Enzymol., 350, 87-96; 2002).

Exogenous DNA can be loaded on a plasmid that replicates into the host cell, or a plasmid that allows the integration of the DNA into the genome of the host cell. Preferably, the nucleic acids encoding heterologous polypeptides are stably integrated into the yeast genome, in particular by the technique of homologous recombination. Preferably, in a set of exogenous nucleic acids as described herein, the exogenous nucleic acids are assembled into a cluster, and said cluster is integrated into the yeast genome.

In particular, polynucleotides encoding a series of enzymes are provided as full-length polynucleotides which may be of different origin, wherein:

the 5' terminal sequence is of the polynucleotide encoding the first enzyme in the series, and the 3' terminal sequence is of the polynucleotide encoding the last enzyme in the series.

Most preferably, each nucleic acid encoding a polypeptide included in an exogenous nucleic acid as described herein comprises, from its 5' end to its 3' end, (i) a regulatory sequence comprising one or more promoter sequences, the said regulatory sequence being functional in the yeast organism wherein it has been introduced, (ii) an ORF encoding a polypeptide of interest and (iii) one or more transcription terminator sequences.

The polynucleotides encoding the enzymes may be in the order of the consecutive enzymatic reactions required for the biosynthesis pathway which is under consideration, or in any other order, provided that the required enzymes are actually produced.

According to the invention, a «functional» enzyme refers to an enzyme, either in its wild-type or in its mutated forms, of which the function has not been inactivated or removed, and which thus possesses its enzymatic activity.

Accordingly, a recombinant host «expressing» at least one given polypeptide encompasses both a recombinant host having at least one gene encoding a functional polypeptide, and a recombinant host expressing at least one nucleic acid encoding said polypeptide.

According to the invention, a «vanilloid» and a «vanilloid compound» are synonymous.

According to the invention, a «substantially pure vanilloid» relates to a composition comprising a vanilloid and only very small amounts (traces) of an isomer of said vanilloid compound, in particular isovanillin, or even no detectable presence of an isomer of said vanilloid compound.

According to the invention, an «isomer of vanilloid compound» relates to a vanilloid compound of formula (II):

(II)

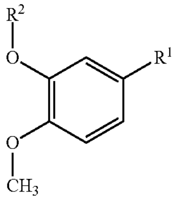

$R^1$ and $R^2$ being as described for the corresponding produced vanilloid.

A «substantially pure vanilloid» is a vanilloid that is produced in a «vanilloid/isomer of vanilloid» molar ratio of more, than 125:1, which is equivalent to 99.2% of purity according to the invention.

In particular, a «substantially pure vanilloid» can be a vanilloid that is produced in a «vanilloid/isomer of vanilloid» molar ratio of at least, and preferably more, than 150:1, which may further include 175:1 or even 200:1.

In particular, a «substantially pure vanilloid» can be a vanilloid with a level of purity that is superior to about 99.2%; 99.3%; 99.4%; 99.5%; 99.6%; 99.7%; 99.8%; 99.9% of purity; or even equal to 100% of purity.

This high level of purity is obtained with the use of a selective Caffeic Acid 3-O-methyltransferase that is able to discriminate between the 3-OH (meta position) and the 4-OH (para position) of a protocatechuic aldehyde or acid, and therefore that does not methylate the 4-OH of said protocatechuic aldehyde or acid, and does not produce any isomer of vanilloid, or only traces as presented above.

Purity is measured by methods appropriate for the compound of interest, e.g. chromatographic methods, agarose or polyacrylamide gel electrophoresis, HPLC analysis, UPLC analysis and the like.

According to a particular embodiment, a method appropriate for measuring purity of the vanilloid of interest is HPLC or UPLC analysis (Ultra Performance Liquid Chromatography).

According to one embodiment, HPLC analysis may be performed on an Agilent 1260 or 1290 series HPLC system using an ACE5-C18 column (4.6×250 mm, 5-μm particle size).

According to another embodiment, UPLC analysis may be performed on a ZORBAX Eclipse Plus RRHD column (3×100 mm; 1.8 μm), at a flow rate of 0.8 ml/min. and at a temperature of 30° C.

Advantageously, an elution profile can be obtained using an acetonitrile/water gradient, using a ($H_2O$/0.1% HCOOH) solution against a ($CH_2CN$/0.1% HCOOH) solution in order to obtain the said gradient. Quantitative assessment of the elution profile can be followed at a wavelength $\lambda$=260 nm and $\lambda$=280 nm using a diode array detector according to standard protocols, such as the one described in the Examples.

In other words, the inventors provide a method for producing a vanilloid compound, comprising a step of methylation that is selective towards the 3-OH of a protocatechuic aldehyde, and which thus provides high selectivity for the production of vanillin in particular.

For reference, a protocatechuic acid is as described in formula (III):

(III)

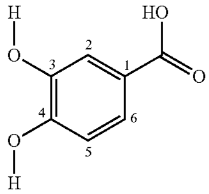

For reference, a protocatechuic aldehyde is as described in formula (IV):

(IV)

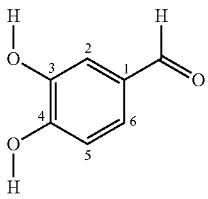

Thus, the invention also relates to methods for converting protocatechuic aldehyde into a substantially pure vanilloid in a recombinant unicellular host.

Preferably, said method for converting a protocatechuic aldehyde into a substantially pure vanilloid or for producing a substantially pure vanilloid is performed with a recombinant host expressing at least a nucleic acid coding for an aromatic carboxylic acid reductase (ACAR), at least a nucleic acid coding for a caffeic acid O-methyltransferase polypeptide that is suitable for methylating selectively the 3-OH of a protocatechuic aldehyde, and at least a nucleic acid coding for a polypeptide having 3-dehydroshikimate dehydratase (3DSD) activity.

Thus, the invention also relates to a method for converting a protocatechuic aldehyde into a substantially pure vanilloid of formula (I):

(I)

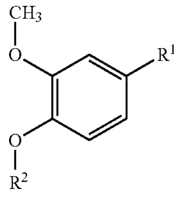

$R^1$ being selected from the group consisting of —CHO; —COOH; —$COOR^3$—$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, $R^2$ being different from a methyl (—$CH_3$), and comprising the steps of:

a) providing a recombinant unicellular host capable of producing said vanilloid, wherein said recombinant host expresses at least a nucleic acid coding for an aromatic carboxylic acid reductase (ACAR) and at least a nucleic acid coding for a polypeptide having 3-dehydroshikimate dehydratase (3DSD) activity;

b) cultivating said host in a suitable medium; and c) recovering the produced vanilloid from said host or from the culture supernatant thereof, wherein said recombinant host expresses at least a nucleic acid coding for a caffeic acid O-methyltransferase polypeptide that is suitable for methylating selectively the 3-OH of a protocatechuic aldehyde, in particular for a caffeic acid O-methyltransferase polypeptide from *Medicago sativa*, *Rosa chinensis*, or *Vanilla planifolia*.

The inventors have now found that, by expressing specifically in a recombinant unicellular host a class of caffeic acid 3-O-methyltransferases of plant origin, they could achieve 100% selectivity for the production of vanillin and vanillic acid, while improving or at least maintaining the same level of production.

In particular, it has been found that said class of caffeic acid 3-O-methyltransferases is able to discriminate between the 3-OH (meta position) and the 4-OH (para position) of a protocatechuic aldehyde.

In the sense of the invention, a "selective" or "specific" caffeic acid 3-O-methyltransferase is a caffeic acid 3-O-methyltransferase that is able to discriminate between the 3-OH and the 4-OH of a protocatechuic acid or a protocatechuic aldehyde, and thus that is not methylating the 4-OH of said protocatechuic acid or said protocatechuic aldehyde in a detectable manner, as shown from the experimental conditions that are set up in example 1.

"Selective" and "specific" are considered herein as synonymous.

Preferably, a "selective" caffeic acid 3-O-methyltransferase is a caffeic acid 3-O-methyltransferase that is able to methylate selectively the 3-OH of a protocatechuic aldehyde.

According to one embodiment, a "selective" caffeic acid 3-O-methyltransferase can be a caffeic acid 3-O-methyltransferase that is able to methylate selectively the 3-OH of a protocatechuic aldehyde, and which also recognizes selectively a protocatechuic aldehyde as a substrate in comparison to a protocatechuic acid.

According to said embodiment, a "selective" caffeic acid 3-O-methyltransferase can be a caffeic acid 3-O-methyltransferase that is able to methylate selectively the 3-OH of a protocatechuic aldehyde, and that is not methylating the 3-OH and the 4-OH of a protocatechuic acid.

Figure 3:
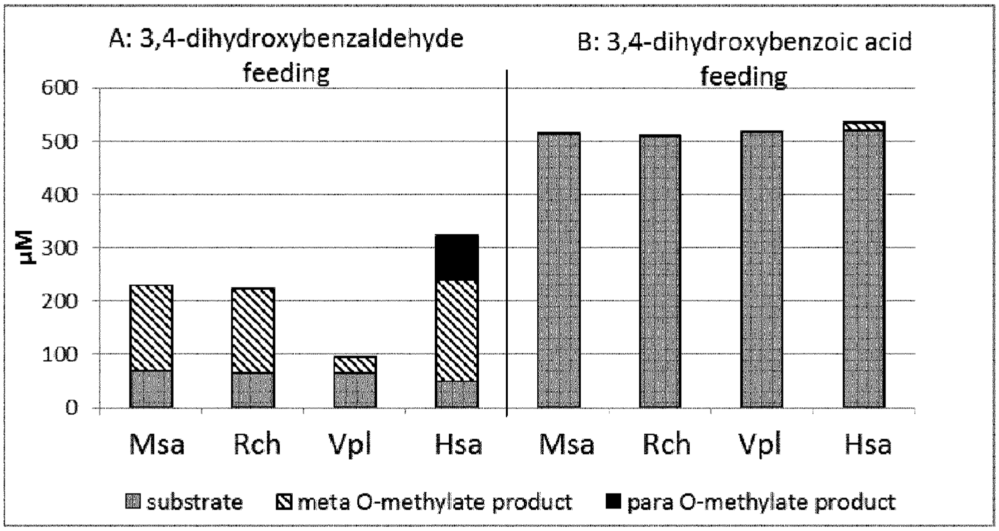
FIG. 3: Substrate specificity of caffeic acid O-methyltransferases for meta-position compared to catechol O-methyltransferases. Supernatant of the yeast cell expressing COMT proteins are illustrated. A: 3,4-dihydroxybenzaldehyde feeding B: 3,4-dihydroxybenzoic acid feeding. Remaining substrate (acid form only) and products are indicated. The y-axis scale is in M. Legend: msa=caffeic acid O-methyltransferase from *Medicago sativa*; rch=caffeic acid O-methyltransferase from *Rosa chinensis*; vpl=caffeic acid O-methyltransferase from *Vanilla planifolia*; hsa=catechol O-methyltransferase from *Homo sapiens.*
Figures 4A, 4B:
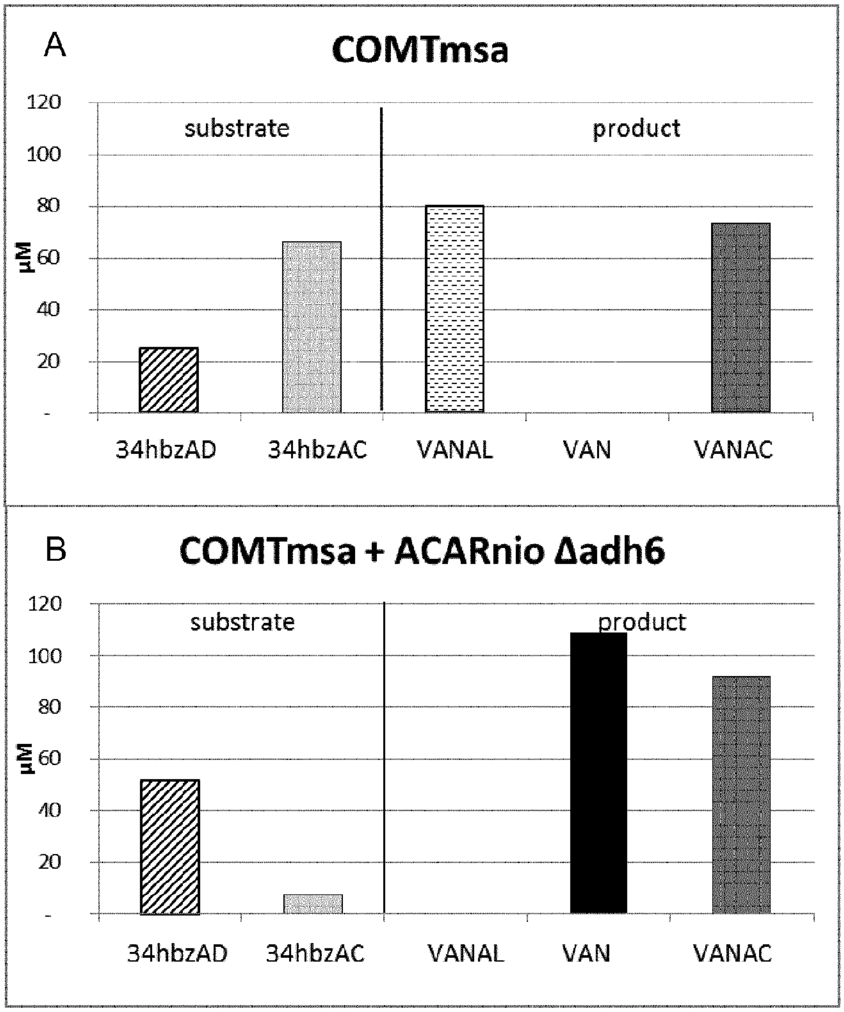
FIG. 4: Metabolite concentrations from a 300 μM 3,4-dihydroxybenzaldehyde feeding on a msa-expressing cell clarified supernatant (FIG. 4A) and in a msa and CAR-co-expressing Δadh6 yeast cell clarified supernatant (FIG. 4B). Chromatogram recorded at 260 nm and 280 nm on UPLC1290 of msa-expressing cell (FIG. 4C). Chromatogram recoded at 260 nm and 280 nm on HPLC1290 of msa and CAR/PPTase co-expressing cell in a Δadh6 yeast cell (FIG. 4D). Retention times of standard samples are indicated for reference along the x-axis (minutes): 3,4-dihydroxybenzaldehyde (34AD or 34hbzAD) 2.51 min; 3,4-dihydroxybenzoic acid (34AC or 34hbzAC) 2.25 min; vanillin (VAN) 2.91 min, isovanillin 2.84 min, vanillic acid (VANAC) 2.64 min, isovanillic acid 2.75 min, vanillyl alcohol (VANAL) 2.38 min. The y-axis scale is in mAU (Arbitrary Units).
Figures 4C, 4D:
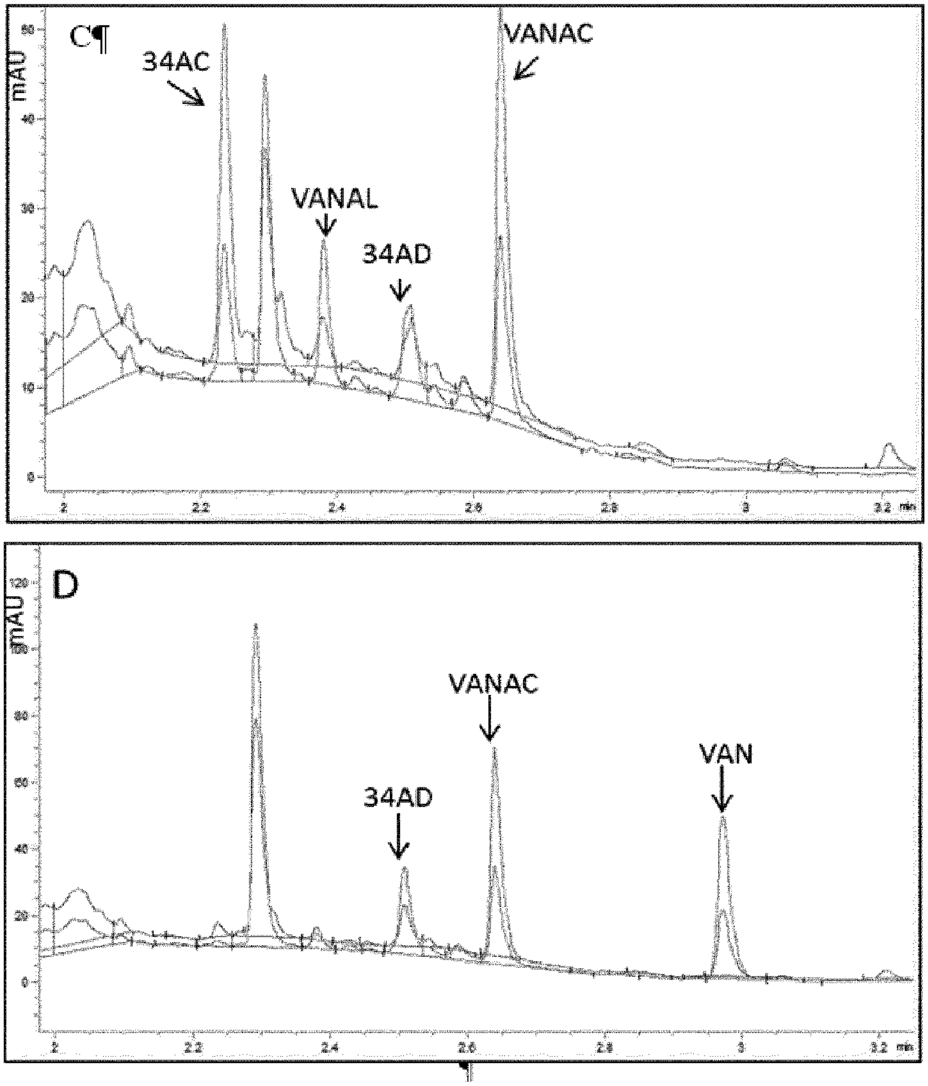

As shown in example 1 and FIGS. 3 and 4, a caffeic acid 3-O-methyltransferase of the invention is particularly suitable for methylating selectively the 3-OH of a protocatechuic aldehyde.

The caffeic acid O-methyltransferase (COMT) is an enzyme catalyzing the chemical conversion of 3,4-dihydroxy-trans-cinnamate (caffeate) to 3-methoxy-4-hydroxy-trans-cinnamate (ferulate). This enzyme is also capable of converting protocatechuic aldehyde to vanillin. This enzyme is classified EC 2.1.1.68. This enzyme is involved in phenylpropanoids biosynthesis and accepts, for instance, 3,4-dihydroxybenzaldehyde, 3,4-dihydroxybenzoate (protocatechuate) and catechol as acceptors. Eventually, the same reaction can be catalyzed by the caffeoyl-CoA O-methyl transferase belonging to EC 2.1.1.104.

Protocols for the purification and characterization of a caffeic acid 3-O-methyltransferase from *Medicago sativa* are known in the Art (see Edwards & Dixon; Archives of Biochemistry and Biophysics; Vol. 287, No. 2, pp. 372-379, 1991).

Without wishing to be bound by the theory, the inventors are of the opinion that caffeic acid 3-O-methyltransferases of plant origin are efficient and 100% selective in their native (wild-type) form for catalyzing a selective methylation of 3,4-dihydroxy-trans-cinnamate or caffeate into 3-methoxy-4-hydroxycinnamate or ferulate.

Of course, the invention further contemplates the use of mutated forms, and/or genetically engineered caffeic acid 3-O-methyltransferases as long as the corresponding polypeptides harbor a caffeic acid 3-O-methyltransferase activity with similar specificity. Specificity was evaluated by estimation of para- or meta-methylation product and was quantitatively determined by the HPLC and UPLC method as described in the experimental part.

In particular, the inventors have focused on caffeic acid 3-O-methyltransferases polypeptide from *Medicago sativa, Rosa chinensis*, and *Vanilla planifolia*, respectively of sequences SEQ ID No 1, SEQ ID No 2 and SEQ ID No 3.

Thus, the present invention also relates to recombinant hosts and methods, wherein the said host expresses a nucleic acid coding for a caffeic acid 3-O-methyltransferase polypeptide comprising a sequence selected from SEQ ID NO: 1, 2 or 3.

Caffeic acid 3-O methyltransferases polypeptide from *Medicago sativa, Rosa chinensis*, and *Vanilla planifolia* of sequences SEQ ID No 1, SEQ ID No 2 and SEQ ID No 3, may be encoded by nucleic acids respectively of sequences SEQ ID No 5, SEQ ID No 6 and SEQ ID No 7.

Moreover, caffeic acid 3-O-methyltransferases of the invention appear to be well-expressed in recombinant unicellular hosts which are capable of producing vanilloid compounds.

Thus, the present invention relates to a method for producing a substantially pure vanilloid of formula (I):

(I)

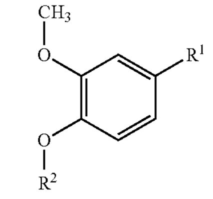

$R^1$ being selected from the group consisting of —CHO; —COOH; —$COOR^3$; —$CH_2OH$; —$CH_2COOH$; —C(=O)$CH_3$; —$CR^3$(OH)COOH; —$CHR^3COOH$; —$CH_2NHC$(=O)$R^3$; wherein $R^3$ is a lower alkyl, $R^2$ being different from a methyl (—$CH_3$), and comprising the steps of:

a) providing a recombinant unicellular host capable of producing said vanilloid, said recombinant host expresses at least a nucleic acid coding for a 3-dehydroshikimate dehydratase (3DSD) and at least a nucleic acid coding for an aromatic carboxylic acid reductase (ACAR);

b) cultivating said host in a suitable medium; and c) recovering the produced vanilloid from said host or from the culture supernatant thereof, wherein said recombinant host expresses at least a nucleic acid coding for a caffeic acid 3-O-methyltransferase polypeptide that is suitable for methylating selectively the 3-OH of a protocatechuic aldehyde, in particular for a caffeic acid O-methyltransferase polypeptide from *Medicago sativa, Rosa chinensis*, or *Vanilla planifolia*.

The term "biosynthesis pathway" as used in the present application refers to the different enzymes involved in specific biochemical steps and intermediates enabling the biosynthesis of products from a substrate in vivo by recombinant host cells. A biosynthesis pathway may be termed "artificial" when one or more of the enzymes comprised therein are encoded by exogenous nucleic acids, i.e. nucleic acids that have been introduced 'artificially' into a host cell, most preferably by using genetic engineering methods.

The specificity of a caffeic acid O-methyltransferase of the invention may be particularly useful when expressed within hosts, such as yeasts, for which the vanilloid metabolic pathway is oriented towards the "dehydroshikimic acid pathway".

According to a particular embodiment, a recombinant host of the invention is cultivated in a suitable medium which does not comprise aromatic amino acids, because such aromatic acids may limit dehydroshikimic acid biosynthesis.

For instance, a recombinant host of the invention may be cultivated in a suitable medium which does not comprise aromatic amino acids such as phenylalanine or tyrosine.

A recombinant host, which may be a genetically modified yeast, may express exogenous and/or endogenous nucleic acids coding for the following enzymes, in order to convert a dehydroshikimic acid into a vanilloid: a 3-dehydroshikimate dehydratase (3DSD), an aromatic carboxylic acid reductase (ACAR) and a caffeic acid O-methyltransferase (COMT).

Of note, ACARs require specific phosphopantetheinylation in order to be functional. Thus, when this activity is absent, it is recommended to either select a recombinant host in which this activity is already present, or alternatively to modify the recombinant host so that it expresses a nucleic acid coding for a phosphopantetheinyl transferase (PPTase).

Preferably, the recombinant host expresses at least a nucleic acid coding for a phosphopantetheinyl transferase (PPTase).

Any of the hosts described herein can further express a uridine 5'-diphosphoglucosyl transferase (UGT), such as a uridine 5'-diphosphoglucosyl transferase (UGT) from *Arabidopsis Thaliana*, or a nucleic acid encoding it.

Thus, any of the hosts described herein can express a UGT of sequence SEQ ID No 9 or 10, or a nucleic acid of sequence SEQ ID No 11 or 12 encoding it.

Suitable 3DSD polypeptides are known. A 3DSD polypeptide according to the present invention may be an enzyme with 3-dehydroshikimate dehydratase activity. Preferably, the 3DSD polypeptide is an enzyme capable of catalyzing conversion of 3-dehydro-shikimate to protocatechuate and $H_2O$. A 3DSD polypeptide according to the present invention is preferably an enzyme classified under EC 4.2.1.118. For example, a suitable polypeptide having 3DSD activity includes the 3DSD polypeptide made by *Podospora pauciseta, Ustilago maydis, Rhodoicoccus jostii, Acinetobacter* sp., *Aspergillus niger* or *Neurospora crassa.*

For reference, a suitable polypeptide having 3-dehydroshikimate dehydratase (3DSD) activity according to the invention may be of sequence SEQ ID No 13 to 16. For reference, a nucleic acid encoding a polypeptide having 3-dehydroshikimate dehydratase (3DSD) activity is of sequence SEQ ID No 17.

Suitable ACAR polypeptides are known. An ACAR polypeptide according to the present invention may be any enzyme having aromatic carboxylic acid reductase activity. Preferably, the ACAR polypeptide is an enzyme capable of catalyzing conversion of protocatechuic acid to protocatechuic aldehyde and/or conversion of vanillic acid to vanillin. An ACAR polypeptide according to the present invention is preferably an enzyme classified under EC 1.2.1.30. For example a suitable ACAR polypeptide is made by *Nocardia* sp., and more particularly *Nocardia iowensis.*

For reference, a suitable polypeptide having aromatic carboxylic acid reductase (ACAR) activity according to the invention may be of sequence SEQ ID No 18.

Suitable PPTase polypeptides are known. A PPTase polypeptide according to the present invention may be any enzyme capable of catalyzing phosphopantetheinylation. Preferably, the PPTase polypeptide is an enzyme capable of catalyzing phosphopantetheinylation of the said ACAR. For example, a suitable PPTase polypeptide is made by *E. coli, Corynebacterium glutamicum* or *Nocardia farcinica.*

For reference, a phosphopantetheinyl transferase (PPTase) of the invention may be of sequence SEQ ID No 19.

Glucosylation of vanilloids, such as vanillin, is particularly useful. Vanillin-β-D-glucoside is the storage form of vanillin found in the *vanilla* pod. It is non-toxic to most organisms, including yeast, and has a higher solubility in water, as compared to vanillin. In addition, the formation of vanillin-β-D-glucoside most likely directs the biosynthesis towards vanillin production. In other words, glycosylation, and more particularly glucosylation, serves to circumvent the inhibitory effect.

Accordingly, the recombinant host of this invention may also express a UGT polypeptide. Suitable UGT polypeptides are known. A UGT polypeptide may be any UDP-Glucose: Aglycon-glucosyltransferase. Preferably the UGT polypeptides can catalyze the glucosylation of vanillin, in particular to produce vanillin-β-D-glucoside. Thus, the UGT polypeptide may be a Family 1 glycosyltransferase. Preferred UGT polypeptides according to the invention are classified under EC 2.4.1.

For reference, a uridine 5'-diphosphoglucosyl transferase (UGT) of the invention may be of sequence SEQ ID No 11 or 12.

The recombinant host may include a heterologous nucleic acid encoding any one of the aforementioned polypeptides having 3DSD, ACAR, PPTase or UGT activity, or a functional homologue of any of the aforementioned polypeptides sharing at least 80%, 85%, 90%, 95%, or even at least 98% sequence identity therewith.

Likewise, a recombinant host of the invention may further express a nucleic acid coding for an additional wild-type or mutant O-methyltransferase, such as a catechol 3-O-methyltransferase, or an AROM polypeptide, as described in WO201302288A1.

For reference, a caffeic acid O-methyltransferase of the invention may be of sequence SEQ ID No 1, 2 or 3.

According to the invention, a recombinant host expressing at least one caffeic acid 3-O-methyltransferase polypeptide from *Medicago sativa, Rosa chinensis*, or *Vanilla planifolia*" of SEQ ID No 1, 2 or 3, may include a heterologous nucleic acid encoding any one of the aforementioned polypeptides, or a functional homologue of any of the aforementioned polypeptides sharing at least 80%, 85%, 90%, 95%, or even at least 98% sequence identity determined over the entire sequence of SEQ ID No 1, 2 or 3.

The "percentage of identity" between two nucleic acid or polypeptide sequences in the sense of the present invention, is as commonly understood in the Art, and is generally determined by comparing two sequences aligned optimally, through a window of comparison.

Part of the nucleotide or polypeptide sequence in the comparison window may comprise additions or deletions (e.g. "gaps") compared to the reference sequence (which does not include these additions or deletions) to obtain alignment optimum between the two sequences.

The percentage of identity is calculated by determining the number of positions at which an identical nucleic base or amino acid is observed for the two sequences compared, dividing the number of positions at which there is identity between two nucleotides or polypeptides by the total number of positions in the window of comparison and multiplying the result by one hundred to get the percentage of nucleotide or polypeptide identity between the two sequences.

Optimal alignment of sequences for comparison can be achieved by computer using known algorithms such as BLAST.

For example, an optimal alignment of sequences can be achieved by the BLASTP program (version 2.2.31+) under default parameters.

According to the invention, polypeptides "sharing at least 80% sequence identity" includes a functional homologue sharing at least 80%, 81%, 82%, 83%, 84%, 85%, 86%, 87%, 88%, 89%, 90%, 91%, 92%, 93%, 94%, 95%, 96%, 97%, 98% and 99% identity with the aforementioned polypeptides having caffeic acid 3-O-methyltransferase, 3DSD, ACAR, PPTase or UGT activity.

Even more advantageously, the recombinant host may be genetically modified in order to be oriented specifically towards the "ACAR-dependent dehydroshikimic acid pathway".

Figure 2A:
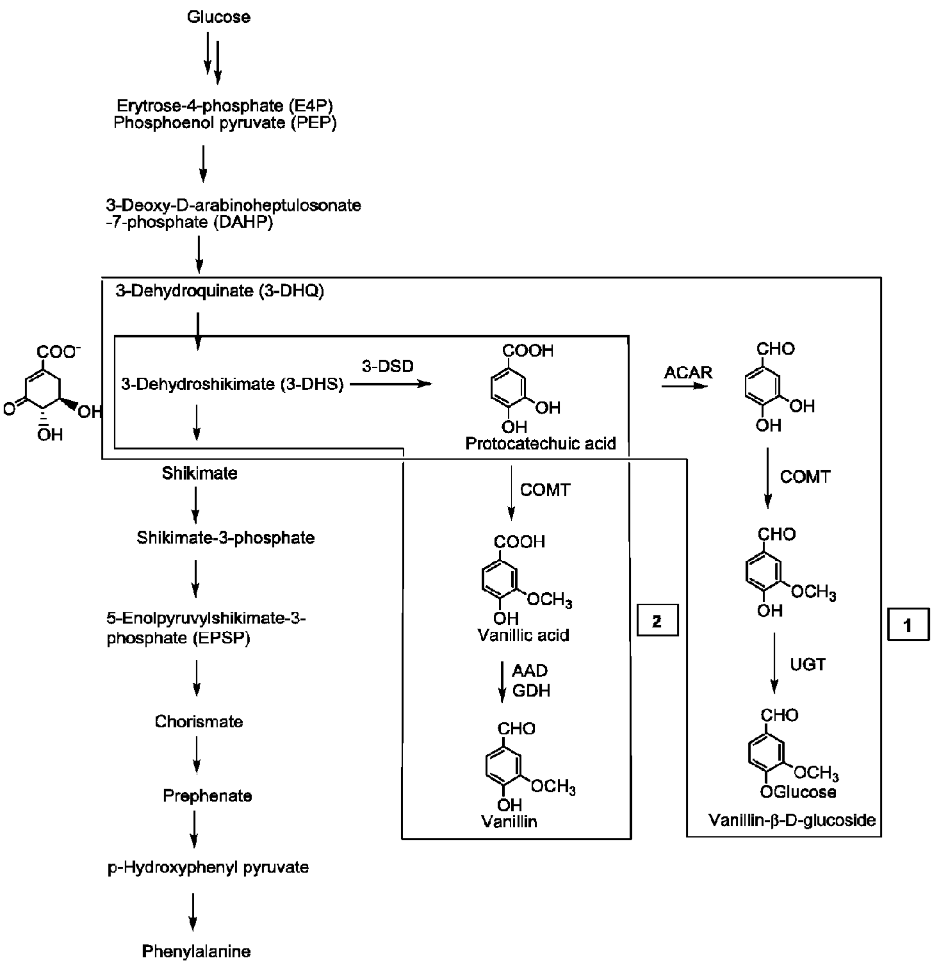
FIG. 2A, 2B: General view of the shikimic acid pathway (pathways 1 & 2—FIG. 2A) and of the aromatic acid-dependent pathway (pathway 3—FIG. 2B) of vanillin biosynthesis in metabolically engineered microorganisms. PAL relates to a phenylalanine ammonia lyase. C4H relates to a cinnamic acid hydroxylase. 4CL relates to a 4-coumarate-CoA ligase. HBH relates to a hydroxybenzoic acid hydroxylase. ECH relates to an enoyl-CoA hydratase/crotonase.
Figure 2B:
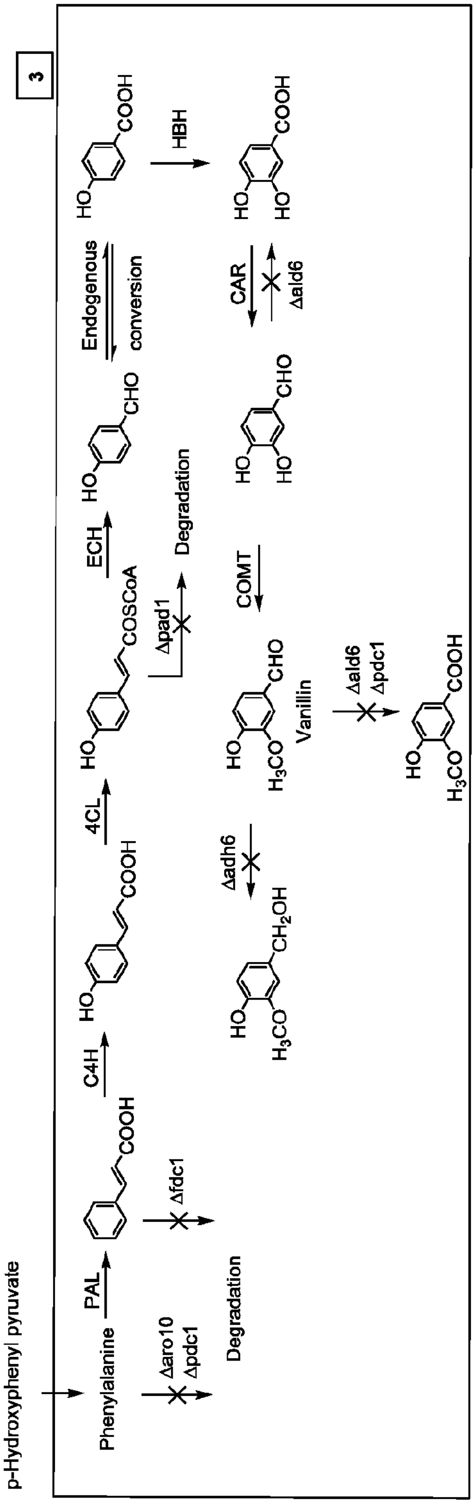

The invention also relates to methods and recombinant hosts for the production of a substantially pure vanilloid through any biosynthetic pathway comprising an aromatic carboxylic acid reductase (ACAR), and at least a nucleic acid coding for a caffeic acid 3-O-methyltransferase polypeptide that is suitable for methylating selectively the 3-OH of a protocatechuic aldehyde, except for the aromatic acid-dependent pathway '3', as shown in FIG. 2.

Thus, the invention also relates to a recombinant unicellular host capable of producing said vanilloid, wherein said recombinant host expresses at least a nucleic acid coding for an aromatic carboxylic acid reductase (ACAR), and at least a nucleic acid coding for a caffeic acid 3-O-methyltransferase polypeptide that is suitable for methylating selectively the 3-OH of a protocatechuic aldehyde, but does not express nucleic acids coding for the following enzymes: a phenylalanine ammonia lyase (PAL) or a tyrosine ammonia lyase (TAL) or a phenylalanine/tyrosine ammonia lyase (PAL/TAL), a CoA ligase, and a crotonase.

The term "phenylalanine ammonia lyase" (PAL) as used herein shall specifically refer to an enzyme catalyzing the phenylalanine deamination reaction (EC. 4.3.1.24). In enzymology, a phenylalanine ammonia-lyase is an enzyme that catalyzes the chemical conversion of L-phenylalanine to trans-cinnamate and ammonia. The systematic name of this enzyme class is L-phenylalanine ammonia-lyase (trans-cinnamate-forming). Other names commonly used include tyrase, phenylalanine deaminase, tyrosine ammonia-lyase, L-tyrosine ammonia-lyase, phenylalanine ammonium-lyase, PAL and L-phenylalanine ammonia-lyase. This enzyme participates in five metabolic pathways: tyrosine metabolism, phenylalanine metabolism, nitrogen metabolism, phenylpropanoid biosynthesis, and alkaloid biosynthesis.

The term "tyrosine ammonia lyase" (TAL, L-tyrosine ammonia-lyase, or Tyrase) as used herein shall specifically refer to an enzyme catalyzing the tyrosine deamination reaction (EC. 4.3.1.23). It is involved in the natural phenols biosynthesis pathway.

The term "phenylalanine/tyrosine ammonia lyase" (PAL/TAL) as used herein shall specifically refer to an enzyme catalyzing the phenylalanine or tyrosine deamination reaction (EC. 4.3.1.25). In enzymology, PAL/TAL catalyzes the non-oxidative deamination of L-phenylalanine and L-tyrosine to form trans-cinnamic acid and p-coumaric acid respectively with similar efficiencies.

The term "CoA ligase" as used herein shall specifically refer to an enzyme catalyzing the CoA esterification of coumaric acid or ferulic acid. Specifically the CoA ligase as described herein is the 4-coumarate-CoA ligase (4CL; EC 6.2.1.12) which catalyzes the chemical reaction of 4-coumarate and CoA to obtain 4-coumaroyl-CoA as a product. This enzyme belongs to the family of ligases, specifically those forming carbon-sulfur bonds as acid-thiol ligases. The systematic name of this enzyme class is 4-coumarate:CoA ligase (AMP-forming). Other names in common use include 4-coumaroyl-CoA synthetase, p-coumaroyl CoA ligase, p-coumaryl coenzyme A synthetase, p-coumaryl-CoA synthetase, p-coumaryl-CoA ligase, feruloyl CoA ligase, hydroxycinnamoyl CoA synthetase, 4-coumarate:coenzyme A ligase, caffeolyl coenzyme A synthetase, p-hydroxycinnamoyl coenzyme A synthetase, 4-coumaryl-CoA synthetase, hydroxycinnamate:CoA ligase, p-coumaryl-CoA ligase, p-hydroxycinnamic acid:CoA ligase, and 4L. This enzyme participates in phyenylpropanoid biosynthesis.

The term "crotonase" as used herein shall specifically refer to enzymes in the superfamily that have been shown to display dehalogenase, hydratase, and isomerase activities, while others have been implicated in carbon-carbon bond formation and cleavage as well as the hydrolysis of thiosters.

Thus the invention also relates to a method for producing a substantially pure vanilloid of formula (I) or for converting a protocatechuic aldehyde into a substantially pure vanilloid of formula (I):

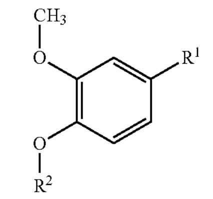

(I)

$R^1$ being selected from the group consisting of —CHO; —COOH; —$COOR^3$; —$CH_2OH$; —$CH_2COOH$; —C(=O)$CH_3$; —$CR^3$(OH)COOH; —$CHR^3COOH$; —$CH_2NHC$(=O)$R^3$; wherein $R^3$ is a lower alkyl, $R^2$ being different from a methyl (—$CH_3$), and comprising the steps of:

a) providing a recombinant unicellular host capable of producing said vanilloid, wherein said recombinant host expresses at least a nucleic acid coding for an aromatic carboxylic acid reductase (ACAR) and does not express nucleic acids coding for the following enzymes: a phenylalanine ammonia lyase (PAL) or a tyrosine ammonia lyase (TAL) or a phenylalanine/tyrosine ammonia lyase (PAL/TAL), a coA ligase, and a crotonase;

b) cultivating said host in a suitable medium; and c) recovering the produced vanilloid from said host or from the culture supernatant thereof, wherein said recombinant host expresses at least a nucleic acid coding for a caffeic acid 3-O-methyltransferase polypeptide that is suitable for methylating selectively the 3-OH of a protocatechuic aldehyde.

In our studies, it is shown that the deletion of the aryl aldehyde dehydrogenase (AAD) ald6 in a recombinant host such as yeast is promoting the production of vanillin.

According to one embodiment, a recombinant host suitable for the methods of the invention does not express a functional alcohol dehydrogenase ADH6.

In some preferred embodiments, the «absence of a functional gene» refers to a endogenous gene having been inactivated by introduction of a DNA insert, or refers to a gene whose coding sequence has been partially of completely deleted.

The man skilled in the art knows various means to obtain such absence of functionality and/or the inactivation of a gene, such as:

- introduction of a mutation into the gene, in particular generation of a stop codon inducing the expression of a non-functional, truncated protein;
- introduction of an 'insert' into the gene, inactivating its correct transcription; e.g. interruption of the gene sequence by introduction of one or more exogenous nucleic acids, which encompasses introduction of a set of exogenous nucleic acids,
- replacement of the natural promoter of the gene by a non-functional promoter, or complete suppression of the promoter,
- deletion complete or partial of the coding sequence of the gene.

In some embodiments, the introduction of a mutation into the gene may be achieved by mutagenesis, which includes random and directed mutagenesis.

Thus, according to a particular embodiment, the recombinant host, which may be a yeast, does not comprise a functional gene ald6 and/or does not express the aldehyde dehydrogenase ald6, or a functional homolog. For reference the ald6 protein sequence of *Saccharomyces cerevisiae*, of sequence SEQ ID No 21, is incorporated herein for reference, as well as a nucleic acid encoding it (SEQ ID No 20). Its disruption causes an improved availability of aldehyde intermediates in the biosynthesis pathway towards vanilloids.

Vanilloids of the Invention

Herebelow are described vanilloids which may be obtained and/or produced using the methods and yeasts of the invention.

Vanilloids of the invention include vanillyl alcohol, vanillin, vanillic acid, vanillin-glycoside, acetovanillone, vanillylmandelic acid, homovanillic acid, and capsaicin.

Vanilloids of the invention may also include the above-mentioned vanilloids in a glycosylated form, and more particularly vanillin glycosides.

According to an exemplary embodiment, a vanilloid of the invention is vanillin or vanillic acid. Thus, according to said embodiment, an isomer of vanilloid is isovanillin or isovanillic acid. For reference, the structures of vanillin, isovanillin, vanillic acid and isovanillic acid are respectively given herebelow:

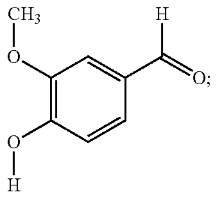
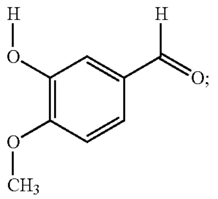

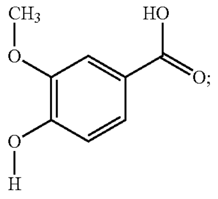
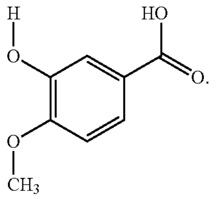

For reference, the structure of acetovanillon, also referred herein as apocynin or 4-hydroxy-3-methoxyacetophenon, is given herebelow:

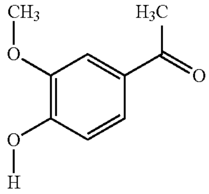

For reference, the structure of vanillylmandelic acid, also referred herein as VMA, is given herebelow:

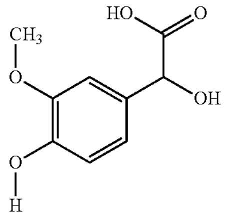

For reference, the structure of homovanillic acid is given herebelow:

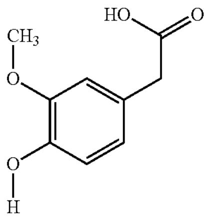

Vanilloids of the invention further include vanilloid derivatives known as capsaicinoids, which include in particular capsaicin, dihydrocapsaicin, nordihydrocapsaicin, homodihydrocapsaicin, homocapsaicin and nonivamide.

For reference, the structure of capsaicin, also referred herein as 8-methyl-N-vanillyl-6-nonenamide, is given herebelow:

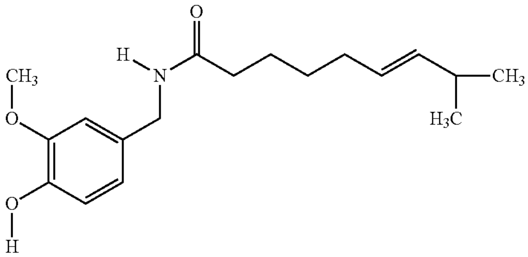 [SMILES: COc1cc(CNC(=O)CCCC/C=C/C(C)C)ccc1O]

Vanilloids of the invention can be defined according to the general formula (I):

(I)

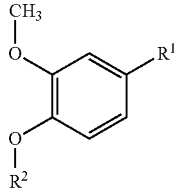

$R^1$ being generally selected from the group consisting of —CHO; —COOH; $COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, and $R^2$ being different from a methyl (—$CH_3$).

The expression "lower alkyl" is known in the Art and may include a linear or ramified, saturated or unsaturated $C_1$-$C_{10}$ alkyl, which thus encompasses a $C_1$-$C_2$ alkyl, a $C_1$-$C_3$ alkyl, a $C_1$-$C_4$ alkyl, a $C_1$-$C_5$ alkyl, a $C_1$-$C_6$ alkyl, a $C_1$-$C_7$ alkyl, a $C_1$-$C_8$ alkyl, a $C_1$-$C_9$ alkyl and a $C_1$-$C_{10}$ alkyl.

A "lower alkyl" may thus include a linear or ramified, saturated or insaturated $C_1$-$C_{10}$ alkyl, $C_1$-$C_4$ alkyl, $C_1$-$C_2$ alkyl, $C_1$-$C_3$ alkyl, $C_2$-$C_3$ alkyl, $C_2$-$C_4$ alkyl, $C_2$-$C_5$ alkyl, $C_2$-$C_6$ alkyl, $C_2$-$C_7$ alkyl, $C_2$-$C_8$ alkyl, $C_2$-$C_9$ alkyl, $C_2$-$C_{10}$ alkyl, $C_2$-$C_{10}$ alkyl, $C_3$-$C_4$ alkyl, $C_3$-$C_5$ alkyl, $C_3$-$C_6$ alkyl, $C_3$-$C_7$ alkyl, $C_3$-$C_8$ alkyl, $C_3$-$C_9$ alkyl, $C_3$-$C_{10}$ alkyl, $C_4$-$C_5$ alkyl, $C_4$-$C_6$ alkyl, $C_4$-$C_7$ alkyl, $C_4$-$C_8$ alkyl, $C_4$-$C_9$ alkyl, $C_4$-$C_{10}$ alkyl, $C_5$-$C_6$ alkyl, $C_5$-$C_7$ alkyl, $C_5$-$C_8$ alkyl, $C_5$-$C_9$ alkyl, $C_5$-$C_{10}$ alkyl, $C_6$-$C_7$ alkyl, $C_6$-$C_8$ alkyl, $C_6$-$C_9$ alkyl, $C_6$-$C_{10}$ alkyl, $C_7$-$C_8$ alkyl, $C_7$-$C_9$ alkyl, $C_7$-$C_{10}$ alkyl, $C_8$-$C_9$ alkyl, $C_8$-$C_{10}$ alkyl, $C_9$-$C_{10}$ alkyl or even a methyl (—$CH_3$).

According to a preferred embodiment, $R^1$ is —CHO.

According to a particular embodiment, $R^2$ may be selected from the group consisting of H, sulfate, phosphate and a glycoside.

According to a preferred embodiment, $R^2$ is H.

When the vanilloid of the invention comprises a glycoside, it is preferably a glucoside, and even more preferably a β-D-glucoside.

According to a particular embodiment, vanilloids of the invention can be defined according to the general formula (I):

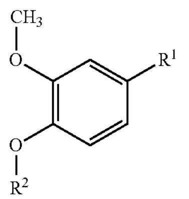

(I)

$R^1$ being selected from the group consisting of —CHO; —COOH, and $R^2$ being different from a methyl (—$CH_3$).

According to one embodiment, vanilloids of the invention can be defined according to the general formula (I), wherein $R^1$ is a glycoside, preferably a glucoside; and $R^2$ is different from a methyl (—$CH_3$).

According to another embodiment, a vanillin-β-D-glucoside can be defined according to the general formula (I), wherein $R^1$ is —CHO and $R^2$ is glucose.

For reference, the structure of a vanillin-β-D-glucoside is given herebelow:

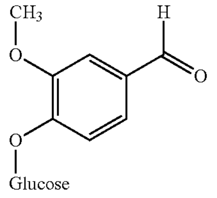

According to another particular embodiment, vanilloids of the invention can be defined according to the general formula (I), wherein $R^1$ is selected from —CHO and —COOH; and $R^2$ is different from a methyl (—$CH_3$). Preferably, $R^2$ is H.

According to a preferred embodiment, vanilloids of the invention can be defined according to the general formula (I), wherein $R^1$ is selected from —CHO and —COOH; and $R^2$ is H.

According to the most preferred embodiment, a vanilloid of the invention is vanillin.

Recombinant Unicellular Host

The invention relates to recombinant hosts, such as yeasts, as well as methods using said recombinant unicellular hosts.

According to the invention, a «recombinant unicellular host» may be a recombinant unicellular microorganism selected from a bacterium, an archaeon, a yeast, a protozoon, an alga, and a fungus.

According to the invention, a «recombinant unicellular host» may be for instance a bacterium, a cyanobacterium, an archaebacterium, a yeast or a fungus.

A species and strain selected for use as a vanillin or vanillin glucoside production strain is first analyzed to determine which production genes are endogenous to the strain and which ones are not present. Genes for which an endogenous counterpart is not present in the strain are assembled in one or more recombinant constructs, which are then transformed into the strain in order to supply the missing function(s).

In particular, recombinant hosts of the invention express at least one nucleic acid coding for a caffeic acid 3-O-methyltransferase polypeptide that is suitable for methylating selectively the 3-OH of a protocatechuic aldehyde, in particular a nucleic acid coding for said polypeptide from *Medicago sativa, Rosa chinensis*, and/or *Vanilla planifolia.*

Exemplary prokaryotic and eukaryotic species are described in more detail below. However, it will be appreciated that other species may be suitable.

In some embodiments, a recombinant host can be an Ascomycete.

In some embodiments, a recombinant host can be a cyanobacterium selected from the group consisting of *Synechocystis, Synechococcus, Anabaena, Cyanothece, Thermosynechococcus, Rhodopseudomonas.*

In some embodiments, a recombinant host can be of a genus selected from the group consisting of *Aspergillus, Candida, Pichia, Saccharomyces* and *Rhodotorula.*

In some embodiments, a recombinant host can be a photosynthetic microorganism. For example, the organism can be of a genus selected from the group consisting of *Chlamydomonas, Dunaliella, Chlorella, Botryococcus, Nannochloropsis, Physcomitrella* and *Ceratodon.*

In some embodiments, a recombinant host can be a prokaryote such as *Escherichia coli, Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of vanilloid compounds.

In some embodiments, a recombinant host can be of the genus *Saccharomyces*, which includes *Zygosaccharomyces fermentatii, Zygosaccharomyces bisporus, Debaromyces occidentalis, Torulaspora delbrueckii, Kluyvezromyces lactis, Pichia pastoris, Saccharomyces cerevisae* and *Schizosaccharomyces pombe.*

According to a particular embodiment, a recombinant host can be a yeast such as *Saccharomyces cerevisiae* or *Schizosaccharomyces pombe*, or a bacteria such as *Escherichia coli.*

Thus, a recombinant host can be selected from *Saccharomyces cerevisiae* and *Schizosaccharomyces pombe.*

By "recombinant yeast" or "genetically modified yeast" is meant a strain of yeast whose genetic material has been modified, either by suppression or inactivation of genes, and/or by addition of exogenous genetic material.

Yeasts are eukaryotic unicellular microorganisms. Yeasts are chemoorganotrophs, as they use organic compounds as a source of energy and do not require sunlight to grow. Over 1,500 species are currently known. A well-known genus of yeast is *Saccharomyces.*

In particular, *Saccharomyces cerevisiae* is another widely used chassis organism in synthetic biology, and can be used as the recombinant microorganism platform. Similar to *E. coli* and *Pseudomonas*, there are libraries of mutants, plasmids, detailed computer models of metabolism and other information available for *S. cerevisiae*, allowing for rational design of various modules to enhance product yield. Methods are known for making recombinant microorganisms.

Preferably, the recombinant unicellular host is a yeast such as *Saccharomyces cerevisiae* or *Schizosaccharomyces pombe.*

According to one exemplary embodiment, *Saccharomyces cerevisiae* strains can be isogenic haploids derived from BY4741, which are obtainable from EUROSCARF (haploid α-mater BY00 or α-mater BY10). For reference, the yeast strain BY4741 is derived from a strain collection that contains knock outs of auxotrophic (-ura3, -leu2, his3) marker genes.

Thus, according to one embodiment, a yeast strain according to the invention, can be a yeast strain that contains knock outs of auxotrophic (-ura3, -leu2, his3) marker genes.

According to another embodiment, the recombinant host is *Schizosaccharomyces pombe* and further expresses at least a nucleic acid encoding an aromatic carboxylic acid reductase (ACAR), and does not express nucleic acids coding for the following enzymes: a phenylalanine ammonia lyase (PAL) or a tyrosine ammonia lyase (TAL) or a phenylalanine/tyrosine ammonia lyase (PAL/TAL), a coA ligase, and a crotonase.

When the recombinant host is *Saccharomyces cerevisiae*, said host preferably expresses at least a nucleic acid encoding a phosphopantetheinyl transferase (PPTase).

According to one embodiment, the recombinant host is *Saccharomyces cerevisiae*, and further expresses at least a nucleic acid encoding an aromatic carboxylic acid reductase (ACAR) and at least a nucleic acid encoding a phosphopantetheinyl transferase (PPTase), and does not express nucleic acids coding for the following enzymes: a phenylalanine ammonia lyase (PAL) or a tyrosine ammonia lyase (TAL) or a phenylalanine/tyrosine ammonia lyase (PAL/TAL), a coA ligase, and a crotonase.

Thus, according to another embodiment, the recombinant host is *Saccharomyces cerevisiae* and further expresses at least a nucleic acid encoding a 3-dehydroshikimate dehydratase (3DSD), at least a nucleic acid encoding an aromatic carboxylic acid reductase (ACAR), and at least a nucleic acid encoding a phosphopantetheinyl transferase (PPTase).

According to one embodiment, the recombinant host is *Schizosaccharomyces pombe* and expresses at least a nucleic acid encoding a 3-dehydroshikimate dehydratase (3DSD) and at least a nucleic acid encoding an aromatic carboxylic acid reductase (ACAR).

According to one embodiment, a recombinant host does not express a functional alcohol dehydrogenase ADH6.

It is clear that said nucleic acids may be considered as independent nucleic acids, or as part of the same nucleic acid, for instance in the form of a polycistronic nucleic and/or for encoding a polyprotein, without departing from the scope of the invention.

It is also clear that the invention further relates to yeasts, as such, which are suitable for the methods of the invention. In particular, the invention further relates to yeasts which are suitable for producing a vanilloid of the invention, as described above.

Thus, the invention also relates to a yeast suitable for producing a substantially pure vanilloid, and to a yeast suitable for converting a protocatechuic aldehyde into a substantially pure vanilloid.

Thus, the invention also relates to a yeast suitable for producing a substantially pure vanilloid of formula (I):

(I)

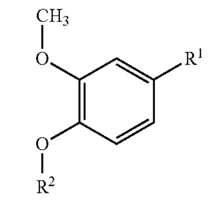

$R^1$ being selected from the group consisting of —CHO; —COOH; —COOR$^3$; —CH$_2$OH; —CH$_2$COOH; —C(═O)CH$_3$; —CR$^3$(OH)COOH; —CHR$^3$COOH; —CH$_2$NHC(═O)R$^3$; wherein $R^3$ is a lower alkyl, $R^2$ being different from a methyl (—CH$_3$), and expressing at least a nucleic acid coding for an aromatic carboxylic acid reductase (ACAR) and a 3-dehydroshikimate dehydratase (3DSD), wherein said yeast expresses at least a nucleic acid coding for a caffeic acid 3-O-methyltransferase polypeptide that is suitable for methylating selectively the 3-OH of a protocatechuic aldehyde, in particular for a caffeic acid O-methyltransferase polypeptide from *Medicago sativa, Rosa chinensis*, or *Vanilla planifolia.*

Thus, the invention also relates to a yeast suitable for producing a substantially pure vanilloid of formula (I):

(I)

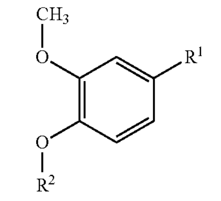

$R^1$ being selected from the group consisting of —CHO; —COOH; —COOR$^3$; —CH$_2$OH; —CH$_2$COOH; —C(═O)CH$_3$; —CR$^3$(OH)COOH; —CHR$^3$COOH; —CH$_2$NHC(═O)R$^3$; wherein $R^3$ is a lower alkyl, $R^2$ being different from a methyl (—CH$_3$), expressing at least a nucleic acid coding for an aromatic carboxylic acid reductase (ACAR), wherein said yeast expresses at least a nucleic acid coding for a caffeic acid 3-O-methyltransferase polypeptide that is suitable for methylating selectively the 3-OH of a protocatechuic aldehyde, and does not express nucleic acids coding for the following enzymes: a phenylalanine ammonia lyase (PAL) or a tyrosine ammonia lyase (TAL) or a phenylalanine/tyrosine ammonia lyase (PAL/TAL), a coA ligase, and a crotonase.

Thus, the invention also relates to a yeast suitable for producing a substantially pure vanilloid of formula (I):

(I)

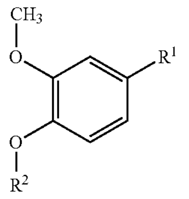

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyle, $R^2$ being different from a methyl (—$CH_3$), expressing at least a nucleic acid coding for an aromatic carboxylic acid reductase (ACAR), and at least a nucleic acid coding for a phosphopantetheinyl transferase (PPTase), wherein said yeast expresses at least a nucleic acid coding for a caffeic acid 3-O-methyltransferase polypeptide that is suitable for methylating selectively the 3-OH of a protocatechuic aldehyde, in particular for a caffeic acid O-methyltransferase polypeptide from *Medicago saliva, Rosa chinensis*, or *Vanilla planifolia*, and does not express nucleic acids coding for the following enzymes: a phenylalanine ammonia lyase (PAL) or a tyrosine ammonia lyase (TAL) or a phenylalanine/tyrosine ammonia lyase (PAL/TAL), a coA ligase, and a crotonase.

Thus, the invention also relates to a yeast suitable for producing a substantially pure vanilloid of formula (I):

(I)

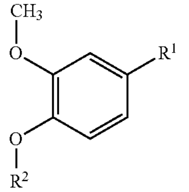

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, $R^2$ being different from a methyl (—$CH_3$), expressing at least a nucleic acid coding for an aromatic carboxylic acid reductase (ACAR), at least a nucleic acid coding for a phosphopantetheinyl transferase (PPTase), and at least a nucleic acid coding for a 3-dehydroshikimate dehydratase (3DSD), wherein said yeast expresses at least a nucleic acid coding for a caffeic acid 3-O-methyltransferase polypeptide that is suitable for methylating selectively the 3-OH of a protocatechuic aldehyde, in particular for a caffeic acid O-methyltransferase polypeptide from *Medicago sativa, Rosa chinensis*, or *Vanilla planifolia*.

The invention also relates to a yeast suitable for converting a protocatechuic aldehyde into a substantially pure vanilloid of formula (I):

(I)

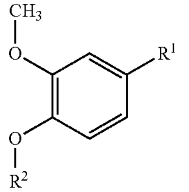

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, $R^2$ being different from a methyl (—$CH_3$), expressing at least a nucleic acid coding for an aromatic carboxylic acid reductase (ACAR), wherein said yeast expresses at least a nucleic acid coding for a caffeic acid 3-O-methyltransferase polypeptide that is suitable for methylating selectively the 3-OH of a protocatechuic aldehyde, and does not express nucleic acids coding for the following enzymes: a phenylalanine ammonia lyase (PAL) or a tyrosine ammonia lyase (TAL) or a phenylalanine/tyrosine ammonia lyase (PAL/TAL), a coA ligase, and a crotonase.

Thus, the invention also relates to a yeast suitable for converting a protocatechuic aldehyde into a substantially pure vanilloid of formula (I)

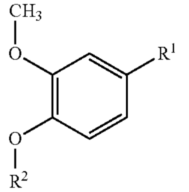

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, $R^2$ being different from a methyl (—$CH_3$), expressing at least a nucleic acid coding for an aromatic carboxylic acid reductase (ACAR) and at least a nucleic acid coding for a phosphopantetheinyl transferase (PPTase), wherein said yeast expresses at least a nucleic acid coding for a caffeic acid 3-O-methyltransferase polypeptide that is suitable for methylating selectively the 3-OH of a protocatechuic aldehyde, in particular for a caffeic acid O-methyltransferase polypeptide from *Medicago saliva, Rosa chinensis*, or *Vanilla planifolia*, and does not express nucleic acids coding for the following enzymes: a phenylalanine ammonia lyase (PAL) or a tyrosine ammonia lyase (TAL) or a phenylalanine/tyrosine ammonia lyase (PAL/TAL), a coA ligase, and a crotonase.

Although a 3-dehydroshikimate dehydratase (3DSD) may be optional when a vanilloid precursor such as protecatechuic aldehyde is produced and/or available to the said yeast, the invention also provides yeasts which comprise a gene encoding a 3-dehydroshikimate dehydratase (3DSD), Thus, the invention also relates to a yeast suitable for converting a protocatechuic aldehyde into a substantially pure vanilloid of formula (I):

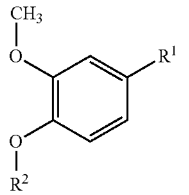

(I)

$R^1$ being selected from the group consisting of —CHO; —COOH; —COOR$^3$; —$CH_2OH$; —$CH_2COOH$; —C(═O)$CH_3$; —$CR^3(OH)COOH$; —$CHR^3COOH$; —$CH_2NHC$(═O)$R^3$; wherein $R^3$ is a lower alkyl, $R^2$ being different from a methyl (—$CH_3$), expressing at least a nucleic acid coding for an aromatic carboxylic acid reductase (ACAR) and at least a nucleic acid coding for a 3-dehydroshikimate dehydratase (3DSD), wherein said yeast expresses at least a nucleic acid coding for a caffeic acid 3-O-methyltransferase polypeptide that is suitable for methylating selectively the 3-OH of a protocatechuic aldehyde, in particular for a caffeic acid O-methyltransferase polypeptide from *Medicago sativa, Rosa chinensis*, or *Vanilla planifolia.*

Thus, the invention also relates to a yeast suitable for converting a protocatechuic aldehyde into a substantially pure vanilloid of formula (I):

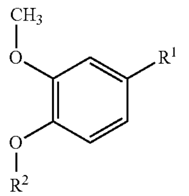

(I)

$R^1$ being selected from the group consisting of —CHO; —COOH; —COOR$^3$; —$CH_2OH$; —$CH_2COOH$; —C(═O)$CH_3$; —$CR^3(OH)COOH$; —$CHR^3COOH$; —$CH_2NHC$(═O)$R^3$; wherein $R^3$ is a lower alkyl, $R^2$ being different from a methyl (—$CH_3$), expressing at least a nucleic acid coding for an aromatic carboxylic acid reductase (ACAR), at least a nucleic acid coding for a 3-dehydroshikimate dehydratase (3DSD), and at least a nucleic acid coding for a phosphopantetheinyl transferase (PPTase), wherein said yeast expresses at least a nucleic acid coding for a caffeic acid 3-O-methyltransferase polypeptide that is suitable for methylating selectively the 3-OH of a protocatechuic aldehyde, in particular for a caffeic acid O-methyltransferase polypeptide from *Medicago sativa, Rosa chinensis*, or *Vanilla planifolia.*

According to the invention, the expressions "at least a gene" or "at least a nucleic acid" encompass "one gene"/"one nucleic acid", and "one or more genes"/"one or more nucleic acids". It also encompasses a gene that is present in the genome of a recombinant host in multiple copies.

Culture Process for Producing a Vanilloid

Examples of appropriate mediums for a selection of recombinant hosts is provided in WO2013022881A1 and Hansen et al., 2009 (Recombinant hosts such as yeasts use sugars as their main carbon and energy source, but non-conventional carbon sources can be accepted too. The major source for energy production in the yeast is glucose and glycolysis is the general pathway for conversion of glucose to pyruvate, whereby production of energy in form of ATP is coupled to the generation of intermediates and reducing power in form of NADH for biosynthetic pathways. Fructose is also a hexose that can be uptake and metabolized by yeast. Galactose is a 'non-conventional' nutrient for yeast, which however can be used as a sole carbon source when glucose is absent from the medium.

In yeast cells supplied with glucose, the GAL genes are repressed. They are activated a thousand fold in cells that are starved for glucose, and this is one of the few pathways in yeast which is regulated in a nearly 'all or-nothing' mode.

In particular, enzymes involved in conversion of galactose to glucose 1 phosphate may be: galactose kinase, galactose-1-phosphate-urydiltransferase, and UDP-glucose-4-epimerase.

Glycerol functions as a compatible solute in osmoregulation in osmotolerant yeasts that are capable of growing in high sugar or salt environments. Many types of yeast can grow on glycerol as a sole carbon source under aerobic conditions, but glycerol is a non-fermentable carbon source for many yeast species, including *S. cerevisiae.* To serve as a carbon source, glycerol after internalization has to convert by glycerol kinase to glycerol-3-phosphate, which is then transformed into dihydroxyacetone phosphate by glycerol-3-phosphate dehydrogenase that is a substrate in gluconeogenesis.

Many types of yeast have the capability of metabolizing ethanol or methanol. In presence of ethanol, ADH2, the enzyme that converts ethanol back into acetaldehyde, is expressed. Acetaldehyde is subsequently converted into acetyl-CoA, the substrate for the citric acid cycle.

According to the invention the term 'cultivating' is used to denote the growth of a recombinant host such as yeast. The term "appropriate medium" refers to a medium (e.g., a sterile, liquid media) comprising nutrients essential or beneficial to the maintenance and/or growth of the cell such as carbon sources or carbon substrates, nitrogen sources, urea, ammonium sulfate, ammonium chloride, ammonium nitrate and ammonium phosphate; phosphorus sources; metal salts, for example magnesium salts, cobalt salts and/or manganese salts; as well as growth factors such as amino acids and vitamins.

According to the invention, such "appropriate" or "suitable medium" is a medium with at least one source of carbon. The source of carbon, also defined as "the substrate", may be selected among the group consisting of glucose, galactose, fructose, arabinose, lactose, mannose, erythrose-4-phosphate, dehydroshikimic acid, catechol, protocatechuic acid, protocatechuic aldehyde, ethanol, glycerol and derivatives thereof.

The term "source of carbon" or "carbon substrate" according to the present invention denotes any source of carbon that can be used by those skilled in the art to support the normal growth of a recombinant unicellular host such as a yeast.

For instance, the source of carbon may be vanilloid precursor selected from the group consisting of protocatechuic aldehyde, protocatechuic acid, protocatechuic alcohol, 4-hydroxyaldehyde, 4-hydrobenzoic acid, 4-hydroxyl alcohol, cinnamic acid, coumaric acid, caffeic acid and ferulic acid.

The source of carbon may be also selected among the group consisting of glucose, fructose, mannose, xylose, arabinose, galactose, lactose, ethanol, cellobiose, glycerol and polysaccharides such as cellulose.

The source of carbon may be obtained from sugars such as hexoses (glucose, fructose, galactose) as well as alcohol compounds with two carbons (ethanol) or three carbons (glycerol).

In particular, said suitable medium comprises at least one compound selected from glucose, galactose, fructose, arabinose, lactose, mannose, erythrose-4-phosphate, dehydroshikimic acid, catechol, protocatechuic acid, protocatechuic aldehyde, ethanol, glycerol and derivatives thereof.

Preferably, said suitable medium comprises at least one compound selected from glucose, galactose, glycerol, ethanol and their mixtures, and protocatechuic aldehyde.

According to one exemplary embodiment, a suitable medium can be the YPGal medium (YEP medium with 3% galactose as the sole carbon source).

According to another exemplary embodiment, a suitable medium comprises at least protocatechuic aldehyde.

The cultivation process comprises a fermentation process (batch, fed-batch or continuous mode) under controlled conditions of pH, temperature, $pO_2$ and aeration, conditions well known to a person skilled in the art.

Composition Comprising Vanilloid

The present invention is also related to a composition comprising a vanilloid obtainable or obtained by one of the methods as disclosed above, and to the use of said composition as a flavoring in the human and animal nutrition field, in pharmacy, and as a fragrance in the cosmetics, perfumery and detergency industries.

Vanillin is a compound well-known for its aromatic properties. However, the flavor profile of an aromatic composition is dependent on for instance byproducts and impurities, and consequently on the preparation process. The composition comprising a vanilloid obtainable by the method of the invention may thus show aromatic notes different from other aromatic composition.

Thus, the present invention also relates to a composition comprising a vanilloid obtainable or obtained by one of the methods as disclosed above, from said host or from the culture supernatant thereof, which includes clarified culture supernatant.

A composition comprising said vanilloid, in the sense of the invention, may include pharmaceutical compositions, cosmetic compositions and/or compositions which are suitable for human and animal nutrition, including oral and topical administration.

According to some embodiments the composition is a culture supernatant or a clarified culture supernatant.

EXAMPLES

Example 1. Substrate Specificity of Isolated COMT Expressed in Yeast

Purpose of the Example

O-Methylation is catalyzed by a family of SAM-dependant methyltransferases (OMTs). According to the literature, substrates are methylated at the meta-positions of their phenyl rings by native O-methyltransferases, and some time from substitution of the para-hydroxyl (4-OH) position. Caffeic acid O-methyltransferases (EC 2.1.1.68) are central to lignin biosynthesis and catalyzes predominantly the O-methylation at meta-position of the phenyl ring. Catechol O-methyltransferases (EC 2.1.1.6) are involved in degradation of catecholamines such as dopamine, epinephrine, and norepinephrine.

3,4-Dihydroxybenzaldehyde (or protocatechuic aldehyde) is a precursor in vanillin biosynthesis. This benzaldehyde derivate possesses two vicinal hydroxyl groups in meta- and in para-position (catechol moiety). The methylation of the meta-hydroxyl is the latest step to get vanillin.

COMT from *Homo sapiens* (hs) of the catechol 3-O-methyltransferase class and COMT from *Medicago saliva* (msa), from *Rosa chinensis* (rch), and from *Vanilla planifola* (vpl), of the caffeic acid 3-O-methyltransferase class were assayed for methylation of 3,4-dihydroxybenzaldehyde.

Material & Methods

In order to compare substrate specificities of caffeic acid O-methyltransferase and catechol O-methyltransferase, genes encoding COMThs, COMTmsa, COMTrch, COMTvp1 were cloned into the yeast genome. Each gene was cloned using an adapted ("codon optimized") version for yeast strains, such as *Saccharomyces cerevisae*. For reference the nucleic acids corresponding to COMTmsa, COMTrch, COMTvp1 and COMThs correspond respectively to sequences SEQ ID No 22 to 25.

All of the *Saccharomyces cerevisiae* strains used in this work were isogenic haploids from BY4741 and were obtained from EUROSCARF (haploid α-mater BY00 or α-mater BY10). Yeast strain BY4741 is derived from a strain collection that contains knock outs of auxotrophic marker genes (-ura3, -leu2, his3).

Figure 5:
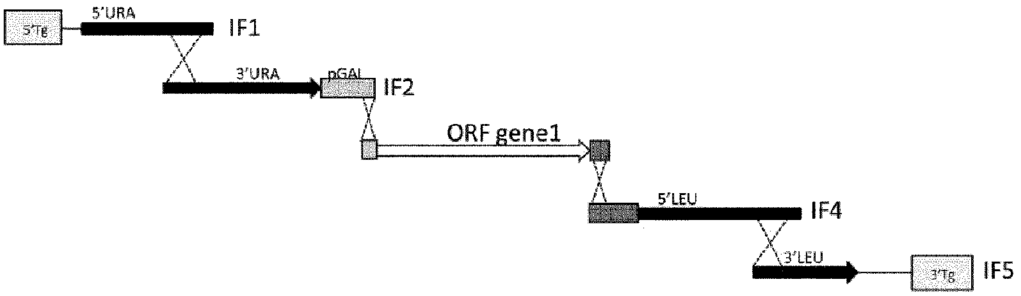
FIG. 5: Strategy for the integration of a candidate gene into the yeast genome. IF1 (IF=Integration Fragments) contains the 5' insertion site in the BUD31 region of the yeast chromosome and 5' end of URA marker, IF2 contains 3' end URA marker and pGAL promoter. IF4 contains tCYC terminator and 5' end of LEU marker and IF5 contains 3' end of LEU marker and 3' insertion site in the BUD31 region. The 5' end of the upstream oligonucleotides used for amplifying the gene of interest contains a sequence of 40 nucleotides homologous with the 3' end of the pGAL1 promoter. The downstream oligonucleotides contain a 40-nucleotide sequence homologous with the 5' end of the tCYC terminator. After assembly by homologous recombination in yeast transformant, the double selection permits the recombinant isolation. After recombination, the gene possesses one promoter (pGAL) and one terminator (tCYC) sequence allowing their expression in yeast cells.

For each gene, recombinant clones were constructed using in vivo homologous recombination at bud31 locus (see FIG. 5). Integration fragments (=IF) were designed. T5' and T3' correspond to the bud31 target sequences of the yeast genome allowing homologous integration into the chromosome locus. URA and LEU are the flanking markers for the double selection. Overlapping sequences correspond to the 5' part and the 3' part of the marker genes. All integration fragments IF1-IF2-IF4 and IF5 were amplified by PCR and amplicons were purified using Wizard PCR Clean-up System (Promega). Synthesized ORF was amplified from GeneArt plasmid. The 5' end of the upstream oligonucleotides used for amplifying the gene of interest contains a sequence of 40 nucleotides homologous with the 3' end of the pGAL1 promoter. The downstream oligonucleotides contain a 40-nucleotide sequence homologous with the 5' end of the tCYC terminator. After assembly by homologous recombination in yeast, the double selection allows selection of the recombinants. All genes are optimized for the yeast expression. Thus, recombinant gene expression is under control of GAL1 inducible promoter and tCYC terminator.

Recombinant clones were grown on induction medium, YPGal medium (YEP medium with 3% galactose as the sole carbon source). Cells were grown overnight in YPGal medium and 3,4-dihydroxybenzaldehyde or 3,4-dihydroxybenzoic acid was added at a final concentration of 500 μM.

Supernatants were then analyzed by high performance liquid chromatography (HPLC) to identify the appropriate product. Metabolites were analyzed using an Agilent 1290 series HPLC system using a ZORBAX RRHD Eclipse plus C18 (3.0×100 mm, 1.8 μm particle size) respectively. An acetonitrile/water gradient was used as an elution system and a diode array detector was used to detect eluted compounds by their UV spectra at 260 nm and 280 nm (see FIG. 3). All standards were obtained from Sigma Aldrich.

TABLE 1

| acetonitrile/water gradient | | |
|---|---|---|
| Time (min) | $H_2O$/0.1% HCOOH | $CH_3CN$/0.1% HCOOH |
| 0 | 95% | 5% |
| 1 | 95% | 5% |
| 2 | 70% | 30% |
| 4 | 69% | 31% |
| 5 | 0 | 100% |
| 5.33 | 0 | 100% |
| 6 | 95% | 5% |
| 7.5 | 95% | 5% |

TABLE 2

| Homology matrix | | | | |
|---|---|---|---|---|
| | COMTmsa | COMTrch | COMTvpl | COMThsa |
| COMTmsa | 100% | 85% | 57% | 12% |
| COMTrch | 85% | 100% | 58% | 9% |
| COMTvpl | 57% | 58% | 100% | 8% |
| COMThsa | 12% | 9% | 8% | 100% |

According to sequence analysis, protein sequences of COMTmsa and COMTrch share 85% sequence identity. COMTvp1 that is a caffeic acid O-methyltransferase too, is more phylogenetically distant from COMTmsa and COMTrch. The caffeic acid O-methylase structure is composed of two domains: the N-terminal part contains a dimerization domain (about 100 amino acids) and the C-terminal domain contains the methyltransferase domain. However, COMThs does not align to other COMTs as it belongs to the catechol O-methyltransferase type (8-12% homology sequence to other caffeic acid O-methyltransferases). This protein is shorter than other caffeic acid O-methyltransferases as it does not contain a dimerization domain.

Results

Substrate specificity was evaluated for those four proteins toward 3,4-dihydroxybenzaldehyde and 3,4-dihydroxyhenzoic acid (FIG. 3).

We clearly observed that COMT enzymes did not share the same regio-specificity for methylation.

1. Caffeic Acid O-Methyltransferases

COMTmsa was able to perform specific 3-O-methylation of 3,4-dihydroxybenzaldehyde (3-methylation of catechol moiety) leading to vanillin biosynthesis. Vanillin is then converted by the endogenous yeast enzyme into vanillic acid and one part of the substrate (3,4-dihydroxybenzaldehyde) is converted to acid (competition between endogenous proteins and COMT). COMTrch behaves exactly as COMTmsa. However, COMTvp1 was less specific towards 3,4-dihydroxybenzaldehyde.

The same test was performed using 3,4-dihydroxybenzoic acid as substrate, and almost no methylation was observed (less than 1%). Thus caffeic acid O-methyltransferases are specific towards the 3-position of the aldehyde form, and there exists a competition between endogenous enzymes that will convert 3,4-dihydroxybenzaldehyde into 3,4-dihydrobenzoic acid that is no more a substrate of COMT proteins.

2. Catechol O-Methyltransferases

When COMThs is expressed, substrates are methylated either at the meta-positions forming vanillin or at the para-positions of their phenyl rings leading to isovanillin production.

Vanillin and isovanillin were then converted by endogenous enzyme in vanillic acid and isovanillic acid respectively. The same test performed using 3,4-dihydroxybenzoic acid as substrate, resulted in very slight methylation (less than 5%). The catechol O-methyltransferases share the same specificity towards the aldehyde form compared to the acid form, but methylate both, meta- and para-position of the phenyl ring.

Example 2. Specificity of COMTmsa when Co-Expressed with CAR in a Δadh6 Yeast Host Cell Material & Methods In order to lower the reduction of the aldehyde form into the corresponding carboxylic acid, an aromatic carboxylic acid reductase (ACAR) protein was added with its activating coupling protein phosphopantetheinyl transferase (PPTase). The bicistronic construction was integrated into the ADH6 locus of the yeast genome by homologous recombination using URA as selectable marker. Prevention of vanillin reduction into vanillyl alcohol was achieved by knockout of the host alcohol dehydrogenase ADH6.

In order to remove the selectable marker, flanking repeated sequences were added to the URA3 gene in order to allow URA3 gene excision. Recombinant cells were selected on URA selective medium and the correct integration was verified by PCR. URA3 encodes an oritidine-5'-phosphate decarboxylase that is involved in uracil synthesis. 5FOA (5-fluoroorotic acid) is converted in 5-fluorouracil by URA3. This toxic metabolite is a selective pressure in favor of excision of URA3 with flanking repeated sequences leading to the ura3 genotype.

COMTmsa was introduced at bud31 locus as described in example 1. This strain was compared to the wild type strain expressing COMTmsa (FIG. 4). Both strains were grown overnight in YPGal medium and 3,4-dihydroxybenzaldehyde was added at a final concentration of 300 μM.

Results

The results show that when aldehyde degradation is lowered, competition between endogenous cell and COMTmsa is lowered, so the yield of 3-O methylation is increased from 53% to 80% and vanillin is thus more stable (0 μM when COMT is expressed alone, and 108 μM when COMTmsa is co expressed with ACAR and PPTase in an Δadh6 strain).

Of note, the yield increases but the specificity of the 3-position remains unchanged.

SEQUENCE LISTING

```
SEQ ID No 1:
Medicago sativa caffeic acid O-methyltransferase
(accession no ACY06328.1)
MGSTGETQITPTHISDEEANLFAMQLASASVLPMILKSALELDLLEIIAK
AGPGAQISPIEIASQLPTTNPDAPVMLDRMLRLLACYNILTCSVRTQQDG
KVQRLYGLATVAKYINKNEDGVSISALNLMNQDKVLMESWYHLKDAVLDG
GIPFNKAYGMTAFEYHGTDPRFNKVFNKGMSDHSTITMKKILETYTGFEG
LKSLVDVGGGTGAVINTIVSKYPTIKGINFDLPHVIEDAPSYPGVEHVGG
DMFVSIPKADAVFMKWICHDWSDEHCLKFLKNCYEALPDNGKVIVAECIL
PVAPDSSLATKGVVHEDVIMLAHNPGGKERTQKEFEDLAKGAGFQGFKVH
CNAFNTYIMEFLKKV

SEQ ID No 2:
Rosa chinensis caffeic acid O-methyltransferase
(accession no Q8GU25.1)
MGSTGETQMTPTQVSDEEANLFAMQLASASVLPMVLKAAIELDLLEIMAK
AGPGAFLSPNDLASQLPTKNPEAPVMLDRMLRLLASYSILTYSLRTLPDG
KVERLYGLGPVCKFLTKNEDGVSIAALCLMNQDKVLVESWYHLKDAVLDG
GIPFNKAYGMTAFDYHGTDPRFNKVFNKGMADHSTITMKKILETYKGFEG
LTSIVDVGGGTGAVVNMIVSKYPSIKGINFDLPHVIEDAPQYPGVQHVGG
```

-continued

SEQUENCE LISTING

DMFVSVPKGDATFMKWICHDWSDEHCLKFLKNCYAALPDNGKVILGECIL
PVAPDTSLATKGVVHTDVVMLAHNPGGKERTEQEFEALAKGSGFQGIRVA
CNAFNTYVIEFLKKI

SEQ ID No 3:
*Vanilla planifolia* caffeic acid O-methyl-
transferase (accession no AAS64572.1)
MATWVEHQQQQNGSKDVDEEACMYAMQLSSMVVTPMTLRVAVELGILEQI
QAGGPDSYLTAEDLAARLGNSNPLAPVMIERILRLLTSYSILNFTDTVDG
EGRTVRSYGAAHVCKYLTPNQDGVSMAPLVLMNTDKVLMESWYHMKDAVT
NGGIPFNLAYGMTAFEYHGKDLRFNKVFNEGMKNNSIIITKKILERYKRF
EDVNVLIDVGGGIGGTISMITAKYPHITIGINFDLPHVVSEAPPFQGVEH
VGGNMFESVPIGDAIFIKWILILDWSDEHCLKLLRNCAKSLPDKGKVIVV
ECILPDAPLVTPEAEGVFHLDMIMLAHNPGGKERTKKEFKELAMLSGFSN
FKALFSYANVWVMEFNK SEQ ID No 4:
Homo sapiens catechol acid O-methyltransferase
MPEAPPLLLAAVLLGLVLLVVLLLLLRHWGWGLCLIGWNEFILQPIHNLL
MGDTKEQRILNHVLQHAEPGNAQSVLEAIDTYCEQKEWAMNVGDKKGKIV
DAVIQEHQPSVLLELGAYCGYSAVRMARLLSPGARLTTIFINPDCAAITQ
RMVDFAGVKDKVTLVVGASQDHPQLKKKYDVDTLDMVFLDHWKDRYLPDT
LLLEECGLLRKGTVLLADNVICPGAPDFLAHVRGSSCFECTHYQSFLEYR
EVVDGLEKAIYKGPGSEAGP SEQ ID No 5:
ADN *Medicago sativa* caffeic acid O-methyl-
transferase (accession no ACY06328.1)
ATGGGTTCAACAGGTGAAACTCAAATAACACCAACCCACATATCAGATGA
AGAAGCAAACCTCTTCGCCATGCAACTAGCAAGTGCTTCAGTTCTTCCCA
TGATTTTGAAATCAGCTCTTGAACTTGATCTCTTAGAAATCATTGCTAAA
GCTGGACCTGGTGCTCAAATTTCACCTATTGAAATTGCTTCTCAGCTTCC
AACAACTAACCCTGATGCACCAGTCATGTTGGACCGAATGTTGCGTCTCT
TGGCTTGTTACAATATCCTCACTTGTTCTGTTCGTACTCAACAAGATGGA
AAGGTTCAGAGACTTTACGGTTTGGCTACTGTTGCTAAGTATTTGGTTAA
GAATGAAGATGGTGTTTCTATTTCTGCTCTTAATCTCATGAATCAGGATA
AAGTGCTCATGGAAAGCTGGTACCACCTAAAAGATGCAGTCCTTGATGGG
GGCATTCCATTCAACAAGGCTTATGGAATGACAGCCTTTGAATACCATGG
AACAGATCCAAGGTTTAACAAGGTTTTCAACAAGGGGATGTCTGATCACT
CTACCATCACAATGAAGAAAATTCTTGAGACCTACACAGGTTTTGAAGGC
CTTAAATCTCTTGTTGATGTAGGTGGTGGTACCGGAGCTGTAATTAACAC
GATTGTCTCAAAATATCCCACTATTAAGGGTATTAATTTTGATTTACCCC
ATGTCATTGAAGATGCTCCATCTTATCCAGGAGTTGAGCATGTTGGTGGA
GACATGTTTGTCAGTATTCCAAAGGCTGATGCTGTTTTTATGAAGTGGAT
TTGTCATGACTGGAGTGATGAGCACTGCTTGAAATTTTTGAAGAACTGCT
ATGAGGCACTGCCAGACAATGGAAAAGTGATTGTGGCAGAATGCATACTT
CCAGTGGCTCCAGATTCAAGCCTGGCCACAAAAGGTGTGGTTCACATTGA
TGTGATCATGTTGGCTCATAATCCAGGTGGGAAAGAGAGAACACAAAAAG
AGTTTGAGGATCTTGCCAAAGGTGCTGGATTCCAGGTTTCAAAGTCCATT
GTAATGCTTTCAACACATACATCATGGAGTTTCTTAAGAAGGTTTAA SEQ ID No 6:
ADN *Rosa chinensis* caffeic acid O-methyl-
transferase(accession no Q8GU25.1)
ATGGGTTCAACCGGCGAGACTCAGATGACTCCGACCCAAGTCTCCGACGA
GGAAGCCAACCTCTTCGCCATGCAACTCGCCAGCGCCTCCGTCCTCCCCA
TGGTTCTCAAAGCCGCCATTGAGCTCGACCTCTTGGAGATCATGGCCAAG
GCCGGACCCGGCGCGTTCCTCTCCCCTAATGACCTAGCCTCTCAGCTTCC
GACCAAGAACCCCGAAGCTCCAGTCATGCTTGACCGGATGCTTCGCCTTC
TGGCCAGCTACTCCATTCTAACCTACTCCTTGCGTACACTTCCGGACGGC
AAAGTTGAGAGGCTCTACGGTTTGGGACCTGTGTGTAAATTCTTGACCAA
GAACGAAGATGGTGTCTCCATTGCTGCTCTCTGCCTCATGAACCAAGACA
AGGTCCTCGTCGAGAGCTGGTATCATCTAAAGGATGCAGTTCTTGATGGT
GGGATTCCATTTAACAAGGCCTATGGAATGACTGCTTTTGATTACCATGG
AACTGACCCTAGATTCAACAAGGTCTTCAACAAGGGAATGGCTGACCACT
CCACCATTACCATGAAGAAAATCCTTGAGACTTATAAAGGCTTTGAGGGC
CTCACATCCATCGTTGATGTCGGAGGCGGCACCGGAGCTGTTGTTAACAT
GATCGTTTCTAAGTACCCTTCGATCAAGGGCATCAACTTTGACTTGCCTC
ATGTGATCGAAGATGCTCCTCAATATCCTGGTGTGCAACATGTTGGAGGG
GACATGTTTGTAAGTGTACCGAAAGGAGATGCAATTTTCATGAAGTGGAT
ATGTCACGACTGGAGTGACGAGCACTGCTTGAAATTCTTGAAGAATTGCT
ATGCAGCGCTTCCAGACAATGGGAAAGTGATTCTTGGTGAGTGCATTCTG
CCGGTAGCACCGGACACTAGCCTCGCCACCAAGGGAGTTGTCCATATCGA
CGTGGTCATGTTGGCTCACAACCCCGGTGGCAAAGAGAGGACGGAGCAGG
AGTTTGAAGCCCTGGCTAAGGGGTCTGGATTTCAAGGCATTCGAGTAGCA
TGTAATGCTTTCAACACCTATGTCATCGAATTTCTTAAGAAGATCTGA SEQ ID No 7:
ADN *Vanilla planifolia* caffeic acid O-methyl-
transferase (accession no AAS64572.1)
ATGGCTACATGGGTGGAGCACCAACAGCAGCAAAATGGATCCAAGGACGT
GGACGAGGAGGCGTGCATGTACGCCATGCAGTTGTCGAGCATGGTCGTCC
TCCCGATGACGCTTAGGGTAGCCGTCGAGCTCGGCATACTCGAACAAATC
CAGGCCGGGGGCCCAGATTCGTACCTTACTGCCGAGGATTTGGCGGCGAG
GCTCGGCAACTCCAACCCCTTAGCTCCGGTCATGATCGAGCGGATCCTGC
GCCTGCTCACCAGCTACTCCATCCTTAACTTCACCGACACCGTCGACGGG
GAGGGTAGGACCGTCCGGAGCTACGGCGCGGCGCATGTCTGCAAGTACCT
GACTCCCAACCAGGACGGCGTCTCCATGGCGCCTCTCGTCCTCATGAACA
CGGATAAGGTCCTTATGGAGAGCTGGTACCACATGAAGGATGCAGTGACA
AATGGTGGAATACCATTCAATCTAGCATATGGGATGACAGCTTTTGAGTA
TCATGGGAAAGATCTAAGGTTTAATAAGGTGTTCAACGAGGGCATGAAGA
ACAACTCGATCATTATAACGAAGAAGATTTTAGAGAGATACAAAAGGTTT
GAAGATGTCAATGTTTTAATTGATGTTGGTGGTGGAATTGGTGGAACTAT
CAGTATGATTACTGCAAAGTATCCACATATACATGGGATTAATTTTGACC
TTCCTCATGTTGTTTCTGAAGCTCCACCTTTCCAAGGGGTAGAACATGTC
GGTGGAAACATGTTTGAAAGTGTCCCCATTGGTGATGCAATCTTCATAAA
GTGGATTCTTCATGATTGGAGTGATGAGCATTGTTTGAAGCTCCTAAGAA
ATTGTGCAAAATCTTTACCTGACAAAGGAAAAGTCATAGTTGTGGAATGC
ATTCTTCCCGATGCACCTTTGGTGACGCCAGAGGCTGAAGGTGTCTTTCA
TTTGGACATGATAATGTTGGCTCACAATCCTGGGGGAAAGGAGAGAACAA
AGAAAGAGTTTAAAGAATTGGCTATGCTATCTGGTTTCTCTAATTTCAAG
GCACTTTTTAGTTATGCTAATGTTTGGGTCATGGAATTCAACAAATAG SEQ ID No 8:
ADN *Homo sapiens* catechol acid O-methyl-
transferase
ATGCCGGAGGCCCCGCCTCTGCTGTTGGCAGCTGTGTTGCTGGGCCTGGT
GCTGCTGGTGGTGCTGCTGCTGCTTCTGAGGCACTGGGGCTGGGGCCTGT
GCCTTATCGGCTGGAACGAGTTCATCCTGCAGCCCATCCACAACCTGCTC
ATGGGTGACACCAAGGAGCAGCGCATCCTGAACCATGTGCTGCAGCATGC
GGAGCCCGGGAACGCACAGAGCGTGCTGGAGGCCATTGACACCTACTGCG
AGCAGAAGGAGTGGGCCATGAACGTGGGCGACAAGAAAGGCAAGATCGTG
GACGCCGTGATTCAGGAGCACCAGCCCTCCGTGCTGCTGGAGCTGGGGGC
CTACTGTGGCTACTCAGCTGTGCGCATGGCCCGCCTGCTGTCACCAGGGG
CGAGGCTCATCACCATCGAGATCAACCCCGACTGTGCCGCCATCACCCAG
CGGATGGTGGATTTCGCTGGCATGAAGGACAAGGTCACCCTTGTGGTTGG
AGCGTCCCAGGACATCATCCCCCAGCTGAAGAAGAAGTATGATGTGGACA
CACTGGACATGGTCTTCCTCGACCACTGGAAGGACCGGTACCTGCCGGAC
ACGCTTCTCTTGGAGGAATGTGGCCTGCTGCGGAAGGGGACAGTGCTACT
GGCTGACAACGTGATCTGCCCAGGTGCGCCAGACTTCCTAGCACACGTGC
GCGGGAGCAGCTGCTTTGAGTGCACACACTACCAATCGTTCCTGGAATAC
AGGGAGGTGGTGGACGGCCTGGAGAAGGCCATCTACAAGGGCCCAGGCAG
CGAAGCAGGGCCCTGA SEQ ID No 9:
*Arabidopsis Thaliana* uridine 5'-diphosphoglucosyl
transferase 72E2
MHITKPHAAMFSSPGMGHVIPVIELGKRLSANNGFHVTVFVLETDAASAQ
SKFLNSTGVDIVKLPSPDIYGLVDPDDHVVTKIGVIMRAAVPALRSKIAA
MHQKPTALIVDLFGTDALCLAKEFNMLSYVFIPTNARFLGVSIYYPNLDK
DIKEEHTVQRNPLALPGCEPVRFEDTLDAYLVPDEPVYRDFVRHGLAYPK
ADGILVNTWEEMEPKSLKSLLNPKLLGRVARVPVYPIGPLCRPIQSSETD
HPVLDWLNEQPNESVLYISFGSGGCLSAKQLTELAWGLEQSQQRFVWVVR
PPVDGSCCSEYVSANGGGTEDNTPEYLPEGFVSRTSDRGFVVPSWAPQAE
ILSHRAVGGFLTHCGWSSTLESVVGGVPMIAWPLFAEQNMNAALLSDELG
IAVRLDDPKEDISRWKIEALVRKVMTEKEGEAMRRKVKKLRDSAEMSLSI
DGGGLAHESLCRVTKECQRFLERVVDLSRGA SEQ ID No 10:
*Arabidopsis Thaliana* uridine 5'-diphosphoglucosyl
transferase 72B1
MEESKTPHVAIIPSPGMGHLIPLVEFAKRLVHLHGLTVTFVIAGEGPPSK
AQRTVLDSLPSSISSVFLPPVDLTDLSSSTRIESRISLTVTRSNPELRKV
FDSFVEGGRLPTALVVDLFGTDAFDVAVEFHVPPYWYPTTANVLSFFLHL
PKLDETVSCEFRELTEPLMLPGCVPVAGKDFLDPAQDRKDDAYKWLLHNT
KRYKEAEGILVNTFFELEPNAMALQEPGLDKPPVYPVGPLVNIGKQEAKQ
TEESECLKWLDNQPLGSVLYVSFGSGGTLTCEQLNELALGLADSEQRFLW
VIRSPSGIANSSYFDSHSQTDPLTFLPPGFLERTKKRGFVIPFWAPQAQV
LAHPSTGGELTHCGWNSTLESVVSGIPLIAWPLYAEQKMNAVLLSEIRAA
LRPRAGDDGLVRREEVARVVKGLMEGEEGKGVRNKIVIKELKEAACRVLK
DDGTSTKALSLVALKWKAHKKELEQNGNH -continued

SEQUENCE LISTING

SEQ ID No 11:
ADN *Arabidopsis Thaliana* uridine 5'-diphospho-glucosyl transferase 72E2
ATAGAAACACATCATTAACAAAACAAAGCCTCTCTAAATAAAAACAAAAA
GCTAACTGAATAAGAAGAAGTAGTGATGCATATCACAAAACCACACGCCG
CCATGTTTTCCAGTCCCGGAATGGGCCATGTCATCCCGGTGATCGAGCTT
GGAAAGCGTCTCTCCGCTAACAACGGCTTCCACGTCACCGTCTTCGTCCT
CGAAACCGACGCAGCCTCCGCTCAATCCAAGTTCCTAAACTCAACCGGCG
TCGACATCGTCAAACTTCCATCGCCGGACATTTATGGTTTAGTGGACCCC
GACGACCATGTAGTGACCAAGATCGGAGTCATTATGCGTGCAGCAGTTCC
AGCCCTCCGATCCAAGATCGCTGCCATGCATCAAAAGCCAACGGCTCTGA
TCGTTGACTTGTTTGGCACAGATGCGTTATGTCTCGCAAAGGAATTTAAC
ATGTTGAGTTATGTGTTTATCCCTACCAACGCACGTTTTCTCGGAGTTTC
GATTTATTATCCAAATTTGGACAAAGATATCAAGGAAGAGCACACAGTGC
AAAGAAACCCACTCGCTATACCGGGGTGTGAACCGGTTAGGTTCGAAGAT
ACTCTGGATGCATATCTGGTTCCCGACGAACCGGTGTACCGGGATTTTGT
TCGTCATGGTCTGGCTTACCCAAAAGCCGATGGAATTTTGGTAAATACAT
GGGAAGAGATGGAGCCCAAATCATTGAAGTCCCTTCTAAACCCAAAGCTC
TTGGGCCGGGTTGCTCGTGTACCGGTCTATCCAATCGGTCCCTTATGCAG
ACCGATACAATCATCCGAAACCGATCACCCGGTTTTGGATTGGTTAAACG
AACAACCGAACGAGTCGGTTCTCTATATCTCCTTCGGGAGTGGTGGTTGT
CTATCGGCGAAACAGTTAACTGAATTGGCGTGGGGACTCGAGCAGAGCCA
GCAACGGTTCGTATGGGTGGTTCGACCACCGGTCGACGGTTCGTGTTGTA
GCGAGTATGTCTCGGCTAACGGTGGTGGAACCGAAGACAACACGCCAGAG
TATCTACCGGAAGGGTTCGTGAGTCGTACTAGTGATAGAGGTTTCGTGGT
CCCCTCATGGGCCCCACAAGCTGAAATCCTGTCCCATCGGGCCGTTGGTG
GGTTTTTGACCCATTGCGGTTGGAGCTCGACGTTGGAAAGCGTCGTTGGC
GGCGTTCCGATGATCGCATGGCCACTTTTTGCCGAGCAGAATATGAATGC
GGCGTTGCTCAGCGACGAACTGGGAATCGCAGTCAGATTGGATGATCCAA
AGGAGGATATTTCTAGGTGGAAGATTGAGGCGTTGGTGAGGAAGGTTATG
ACTGAGAAGGAAGGTGAAGCGATGAGAAGGAAAGTGAAGAAGTTGAGAGA
CTCGGCGGAGATGTCACTGAGCATTGACGGTGGTGGTTTGGCGCACGAGT
CGCTTTGCAGAGTCACCAAGGAGTGTCAACGGTTTTTGGAACGTGTCGTG
GACTTGTCACGTGGTGCTTAGAAATTGTTACCGTTTTCTAGCTCTTTTAT
TATTAGTGGTTGAATTATACGTGTCGTTCCTCTGTTAGTGTATAATATAA
TAATCGATTTACTCTTTGTAATATAATGATGTTTTTGATATTTTTCAACT
AATTTTCCATTGTAATATTGAATAATCGGGTGTTGTTGTAATTAATAATG
AGAAACAATTTGTT SEQ ID No 12:
ADN *Arabidopsis Thaliana* uridine 5'-diphospho-glucosyl transferase 72B1
AATGATTCACACAAACTCTCTATATAAAGCCATTACTTAATACCACACAA
ATTACAAAAAAAAAAAGAAAAAAGGAGATAATAATCACAAACTACAAAAG
TAGAAAGAAGAAAAAAGAACAAAGTATCAGTTCTTGAATATTTGCATCAA
TGGAGGAATCCAAAACACCTCACGTTGCGATCATACCAAGTCCGGGAATG
GGTCATCTCATACCACTCGTCGAGTTTGCTAAACGACTCGTCCATCTTCA
CGGCCTCACCGTTACCTTCGTCATCGCCGGCGAAGGTCCACCATCAAAAG
CTCAGAGAACCGTCCTCGACTCTCTCCCTTCTTCAATCTCCTCCGTCTTT
CTCCCTCCTGTTGATCTCACCGATCTCTCTTCGTCCACTCGCATCGAATC
TCGGATCTCCCTCACCGTGACTCGTTCAAACCCGGAGCTCCGGAAAGTCT
TCGACTCGTTCGTGGAGGGAGGTCGTTTGCCAACGGCGCTCGTCGTCGAT
CTCTTCGGTACGGACGCTTTCGACGTGGCCGTAGAATTTCACGTGCCACC
GTATATTTTCTACCCAACAACGGCCAACGTCTTGTCGTTTTTTCTCCATT
TGCCTAAACTAGACGAAACGGTGTCGTGTGAGTTCAGGGAATTAACCGAA
CCGCTTATGCTTCCTGGATGTGTACCGGTTGCCGGGAAAGATTTCCTTGA
CCCGGCCCAAGACCGGAAAGACGATGCATACAAATGGCTTCTCCATAACA
CCAAGAGGTACAAAGAAGCCGAAGGTATTCTTGTGAATACCTTCTTTGAG
CTAGAGCCAAATGCTATAAAGGCCTTGCAAGAACCGGGTCTTGATAAACC
ACCGGTTTATCCGGTTGGACCGTTGGTTAACATTGGTAAGCAAGAGGCTA
AGCAAACCGAAGAGTCTGAATGTTTAAAGTGGTTGGATAACCAGCCGCTC
GGTTCGGTTTTATATGTGTCCTTTGGTAGTGGCGGTACCCTCACATGTGA
GCAGCTCAATGAGCTTGCTCTTGGTCTTGCAGATAGTGAGCAACGGTTTC
TTTGGGTCATACGAAGTCCTAGTGGGATCGCTAATTCGTCGTATTTTGAT
TCACATAGCCAAACAGATCCATTGACATTTTTACCACCGGGATTTTTAGA
GCGGACTAAAAAAAGAGGTTTTGTGATCCCTTTTTGGGCTCCACAAGCCC
AAGTCTTGGCGCATCCATCCACGGGAGGATTTTTAACTCATTGTGGATGG
AATTCGACTCTAGAGAGTGTAGTAAGCGGTATTCCACTTATAGCATGGCC
ATTATACGCAGAACAGAAGATGAATGCGGTTTTGTTGAGTGAAGATATTC
GTGCGGCACTTAGGCCGCGTGCCGGGGACGATGGGTTAGTTAGAAGAGAA
GAGGTGGCTAGAGTGGTAAAAGGATTGATGGAAGGTGAAGAAGGCAAAGG
AGTGAGGAACAAGATGAAGGAGTTGAAGGAAGCAGCTTGTAGGGTGTTGA
AGGATGATGGGACTTCGACAAAAGCACTTAGTCTTGTGGCCTTAAAGTGG
AAAGCCCACAAAAAAGAGTTAGAGCAAAATGGCAACCACTAAATATTTGA
TGTTCTAATATGATTTGTATAATCAACGGTGGGATTTGTGCAAATGTGTT
TCTGTATGTATATGTATGTTCTACTTTTCTTTGCTTCGTTTGTCTCAACT -continued

SEQUENCE LISTING

TTTATTTGTATATGTTTTTGGCTTTTGATTAATTCGTAGAAGATGTTGCA
ATTAAGATCAGCTTAGAAGAAGATGTTGCATATATAGTTAAATATTGTTC
AAGAGAATCATCAATTGTCTATCGTCAATAGTTAAATATATATATGGCTT
ATAAAAAT

SEQ ID No 13:
*Podospora anserina* 3-dehydroshikimate dehydratase
MPSKLAITSMSLGRCYAGHSFTTKLDMARKYGYQGLELFHEDLADVAYRL
SGETPSPCGPSPAAQLSAARQILRMCQVRNIFIVCLQPFSQYDGLLDREE
HERRLEQLEFWIELAHELDTDIIQIPANFLPAEEVTEDISLIVSDLQEVA
DMGLQANPPIRFVYEALCWSTRVDTWERSWEVVQRVNRPNFGVCLDIPNI
AGRVYADPTVASGRTPNAEEAIRKSIARLVERVDVSKVFYVQVVDAEKLK
KPLVPGHRFYDPEQPARMSWSRNCRLFYGEKDRGAYLPVKEIAWAFFNGL
GFEGWVSLELFNRRMSDTGFGVPEELARRGAVSWAKLVRDMKITVDSPTQ
QQATQQPIRMLSLSAAL SEQ ID No 14:
*Ustilago maydis* 3-dehydroshikimate dehydratase
MSSIASTSASTMQHPRYSIFTHSVGYHTSKFIGLLSKLDAISAAGLAGVE
MFTDDLWSFAQSDEFGSILAASERETELLTPPDSPLSQPASLRNKIRTHE
NAERAGQHYSAHGACTPDERQREIAAATFIRSYCASRRLQVECLQPLRDV
EGWLKDEDRENAIERVKSRFDIMRALDTHLLLICSQNTRAPQITGDMATI
VRDLTHISDLAAAYTAQTGFETKIGYEALSWGAHIDLWSQAWNIVRTVDR
DNIGLILDSFNTLAREFADPCTRSGIQEPICTTLTSLHSSLQAIQSVPAD
KTFLLQIGDARRLPEPLVPSPRDGEPRPSRMIWSRSSRLMPSSKAS SEQ ID No 15:
*Acinetobacter* sp. 3-dehydroshikimate dehydratase
MKLTSLRVSLLALGLVTSGFAAAETYTVDRYQDDSEKGSLRWAIEQSNAN
SAQENQILIQAVGKAPYVIKVDKPLPPIKSSVKIIGTEWDKTGEFIAIDG
SNYIKGEGEKACPGANPGQYGTNVRTMTLPGLVLQDVNGVTLKGLDVHRF
CIGVLVNRSSNNLIQHNRISNNYGGAGVMITGDDGKGNPTSTTTNNNKVL
DNVFIDNGDGLELTRGAAFNLIANNLFTSTKANPEPSQGTFILWGNDNAV
VGNKFENYSDGLQINWGKRNYIAYNELTNNSLGFNLTGDGNIFDSNKVHG
NRIGIAIRSEKDANARITLIKNQIWDNGKDIKRCEAGGSCVPNQRLGAIV
FGVPALEHEGFVGSRGGGVVIEPAKLQKTCTQPNQQNCNAIPNQGIQAPK
LTVSKKQLTVEVKGTPNQRYNVEFFGNRNASSSEAEQYLGSIVVVTDHQG
LAKANWAPKVSMPSVTANVTDHLGATSELSSAVKMR SEQ ID No 16:
*Aspergillus niger* 3-dehydroshikimate dehydratase
MPNRLGIASMSLGRPGIFISLPWKLHEAARHGYSGIELFFDDLDHYATTH
FNGSHIAAAHAVHALCTTLNLTIICLQPFSFYEGLVDRKQTEYLLTVKLP
TWFQLARILDTDMIQVPSNFAPAQQTTGDRDVIVGDLQRLADIGLAQSPP
FRFVYEALAWGTRVNLWDEAYEIVEAVDRPNFGICLDTFNLAGRVYAHGR
QDGKTVNAEADLAASLKKLRETVDVKKVFYVQVVDGERLERPLDETHPFH
VEGQPVRMNWSRNARLFAFEEDRGGYLPIEETARAFFDTGFEGWVSLELF
SRTLAEKGTGVVTEHARRGLESWKELCRRLEFKGAEPGLDFVPGEVKVQS
VAVGSGKGVEQEEMGVVQHRL SEP ID No 17:
ADN *Aspergillus niger* 3-dehydroshikimate dehydratase
ATGCCCAACCGTCTCGGCATCGCCTCCATGTCCCTTGGACGCCCAGGCAT
CCACTCCCTCCCCTGGAAGCTCCACGAAGCCGCCCGCCACGGCTACAGCG
GGATCGAGCTCTTCTTCGACGACCTGGACCACTACGCAACCACCCACTTC
AATGGCAGCCACATCGCGGCTGCTCACGCCGTGCACGCTCTCTGCACGAC
CCTCAACCTCACCATCATCTGCCTGCAACCCTTCTCCTTCTACGAGGGGC
TCGTCGACCGCAAGCAAACCGAGTATCTATTGACCGTGAAGCTGCCCACA
TGGTTCCAGCTCGCTCGCATCCTCGACACCGACATGATCCAGGTGCCCTC
GAACTTCGCGCCCGCCCAGCAAACCACGGGTGACCGGGACGTGATCGTCG
GCGACCTCCAGCGCCTCGCAGACATCGGCCTGGCACAGTCCCCACCCTTC
CGCTTCGTATACGAAGCACTGGCCTGGGGCACGCGGGTGAACCTGTGGGA
CGAGGCGTACGAGATCGTCGAGGCCGTGGACCGTCCCAACTTCGGTATCT
GTCTTGATACGTTTAACCTTGCGGGTCGGGTGTATGCGCACCCTGGTCGG
CAGGACGGGAAGACGGTCAACGCGGAGGCGGATCTGGCTGCGTCGTTGAA
GAAGTTGCGCGAGACGGTGGATGTCAAGAAGGTGTTCTACGTGCAGGTTG
TGGATGGAGAGAGGCTGGAGAGGCCGTTGGATGAGACCCATCCGTTTCAT
GTGGAGGGGCAGCCGGTGCGGATGAACTGGAGTCGCAATGCGAGGTTGTT
TGCGTTTGAGGAGGATCGCGGCGGGTATTTGCCCATTGAGGAGACCGCGA
GGGCGTTCTTTGATACGGGGTTCGAGGGCTGGGTGTCGTTGGAGTTGTTT
AGTCGCACGTTGGCGGAGAAGGGCACGGGGGTGGTCACGGAGCATGCGAG
ACGCGGGTTGGAGTCGTGGAAGGAGTTGTGTAGGAGGTTGGAGTTTAAGG
GGGCGGAGCCGGGACTGGATTTTGTTCCTGGGGAGGTGAAGGTGCAGTCG
GTTGCTGTGGGGAGTGGGAAGGGGGTGGAACAGGAGGAGATTTGGGTTTT
GTGCAGCATCGGTTGTAG -continued

SEQUENCE LISTING

SEQ ID No 18:
*Nocardia iowensis* Aromatic Carboxylic Acid
Reductase
IVIAVDSPDERLQRRIAQLFAEDEQVKAARPLEAVSAAVSAPGMRLAQTA
ATVMAGYADRPAAGQRAFELNTDDATGRTSLRLLPRFETITYRELWQRVG
EVAAAWHEDPENPLRAGDEVALLGETSIDYATLDLADIHLGAVTVPLQAS
AAVSQLIAILTETSPRLLASTPEHLDAAVECLLAGTTPERLVVFDYHPED
DDQRAAFESARRRLADAGSLVIVETLDAVRARGRDLPAAPLFVPDTDDDP
LALLIYTSGSTGTPKGAMYTNRLAATMWQGNSMLQGNSQRVGINLNYMPM
SHIAGRISLEGVLARGGTAYFAAKSDMSTLFEDIGLVRPTEIFFVPRVCD
MVFQRYQSELDRRSVAGADLDTLDREVKADLRQNYLGGRFLVAVVGSAPL
AAEMKTFMESVLDLPLHDGYGSTEAGASVLLDNQIQRPPVLDYKLVDVPE
LGYFRTDRPHPRGELLLKAETTIPGYYKRPEVTAEFFDEDGFYKTGDIVA
ELEHDRLVYVDRRNNVLKLSQGEFVTVAHLEAVFASSPLIRQIFIYGSSE
RSYLLAVIVPTDDALRGRDTATLKSALAESIQRIAKDANLQPYEIPRDFL
IETEPFTIANGLLSGIAKTLRPNLKERYGAQLEQMYTDLATGQADELLAL
RREAADLPVLETVSRAAKAMLGVASADMRPDAHFTDLGGDSLSALSFSNL
LHEIFGVEVPVGVVVSPANELRDLANYILAERNSGAKRPTFTSVHGGGSE
IRAADLTLDKFIDARTLAAADSIPHAPVPAQTVLLTGANGYLGRFLCLEW
LERLDKTGGTLICVVRGSDAAAARKRLDSAFDSGDPGLLEHYQQLAARTL
EVLAGDIGDPNLGLDDATWQRLAETVDLWHPAALVNHVLPYTQLFGPNVV
GTAEIVRLAITARRKPVTYLSTVGVADQVDPAEYQEDSDVREMSAVRVVR
ESYANGYGNSKWAGEVLLREAHDLCGLPVAVERSDMILAHSRYAGQLNVQ
DVFIRLILSLVATGIAPYSFYRTDADGNRQRAHYDGLPADETAAAITALG
IQATEGFRTYDVLNPYDDGISLDEFVDWLVESGHPIQRITDYSDWFHRFE
TAIRALPEKQRQASVLPLLDAYRNPCPAVRGAILPAKEFQAAVQTAKIGP
EQDIPHLSAPLIDKYVSDLELLQLL SEQ ID No 19:
*Escherichia Coli* Phosphopantetheinyl transferase
MVDMKTTHTSLPFAGHTLHFVEFDPANFCEQDLLWLPHYAQLQHAGRKRK
TEHLAGRIAAVYALREYGYKCVPAIGELRQPVWPAEVYGSISHCGTTALA
VVSRQPIGIDILEIFSVQTARELTDNIITPAEHERLADCGLAFSLALTLA
FSAKESAFKASEIQTDAGFLDYQIISWNTKQQVIIHRENEMFAVHWQIKE
KIVITLCQHD SEQ ID No 20:
*Saccharomyces cerevisiae* Aldehyde dehydrogenase 6
MTKLHFDTAEPVKITLPNGLTYEQPTGLFINNKFMKAQDGKTYPVEDPST
ENTVCEVSSATTEDVEYAIECADRAFHDTEWATQDPRERGRLLSKLADEL
ESQTDLVSSTEALDNGKTLALARGDVTIAINCLRDAAAYADKVNGRTINT
GDGYMNFTTLEPIGVCGQILPWNFPIMMLAWKIAPALAMGNVCILKPAAV
TPLNIALYFASLCKKVGIPAGVVNIVPGPGRTVGAALTNDPRIRKLAFTG
STEVGKSVAVDSSESNLKKITLELGGKSAHLVEDDANIKKTLPNLVNGIF
KNAGQICSSGSRIYVQEGIYDELLAAFKAYLETEIKVGNPFDKANFQGAI
TNRQQFDTIMNYIDIGKKEGAKILTGGEKVGDKGYFIRPTVFYDVNEDMR
WKEEIFGPVVTVAKEKTLEEGVEMANSSEFGLGSGIETESLSTGLKVAKM
LKAGTVWINTYNDFDSRVPFGGVKQSGYGREMGEEVYHAYTEVKAVRLKL SEQ ID No 21:
ADN *Saccharomyces cerevisiae* Aldehyde
dehydrogenase 6
ATGACTAAGCTACACTTTGACACTGCTGAACCAGTCAAGATCACACTTCC
AAATGGTTTGACATACGAGCAACCAACCGGTCTATTCATTAACAACAAGT
TTATGAAAGCTCAAGACGGTAAGACCTATCCCGTCGAAGATCCTTCCACT
GAAAACACCGTTTGTGAGGTCTCTTCTGCCACCACTGAAGATGTTGAATA
TGCTATCGAATGTGCCGACCGTGCTTTCCACGACACTGAATGGGCTACCC
AAGACCCAAGAGAAAGAGGCCGTCTACTAAGTAAGTTGGCTGACGAATTG
GAAAGCCAAATTGACTTGGTTTCTTCCATTGAAGCTTTGGACAATGGTAA
AACTTTGGCCTTAGCCCGTGGGGATGTTACCATTGCAATCAACTGTCTAA
GAGATGCTGCTGCCTATGCCGACAAAGTCAACGGTAGAACAATCAACACC
GGTGACGGCTACATGAACTTCACCACCTTAGAGCCAATCGGTGTCTGTGG
TCAAATTATTCCATGGAACTTTCCAATAATGATGTTGGCTTGGAAGATCG
CCCCAGCATTGGCCATGGGTAACGTCTGTATCTTGAAACCCGCTGCTGTC
ACACCTTTAAATGCCCTATACTTTGCTTCTTTATGTAAGAAGGTTGGTAT
TCCAGCTGGTGTCGTCAACATCGTTCCAGGTCCTGGTAGAACTGTTGGTG
CTGCTTTGACCAACGACCCAAGAATCAGAAAGCTGGCTTTTACCGGTTCT
ACAGAAGTCGGTAAGAGTGTTGCTGTCGACTCTTCTGAATCTAACTTGAA
GAAAATCACTTTGGAACTAGGTGGTAAGTCCGCCCATTTGGTCTTTGACG
ATGCTAACATTAAGAAGACTTTACCAAATCTAGTAAACGGTATTTTCAAG
AACGCTGGTCAAATTTGTTCCTCTGGTTCTAGAATTTACGTTCAAGAAGG
TATTTACGACGAACTATTGGCTGCTTTCAAGGCTTACTTGGAAACCGAAA
TCAAAGTTGGTAATCCATTTGACAAGGCTAACTTCCAAGGTGCTATCACT
AACCGTCAACAATTCGACACAATTATGAACTACATCGATATCGGTAAGAA
AGAAGGCGCCAAGATCTTAACTGGTGGCGAAAAAGTTGGTGACAAGGGTT
ACTTCATCAGACCAACCGTTTTCTACGATGTTAATGAAGACATGAGAATT
GTTAAGGAAGAAATTTTTGGACCAGTTGTCACTGTCGCAAAGTTCAAGAC
TTTAGAAGAAGGTGTCGAAATGGCTAACAGCTCTGAATTCGGTCTAGGTT
CTGGTATCGAAACAGAATCTTTGAGCACAGGTTTGAAGGTGGCCAAGATG
TTGAAGGCCGGTACCGTCTGGATCAACACATACAACGATTTTGACTCCAG
AGTTCCATTCGGTGGTGTTAAGCAATCTGGTTACGGTAGAGAAATGGGTG
AAGAAGTCTACCATGCATACACTGAAGTAAAAGCTGTCAGAATTAAGTTG
TAA SEQ ID No 22:
Optimized ADN *Medicago sativa* caffeic acid O-
methyltransferase
ATGGGTTCTACTGGTGAAACTCAAATTACTCCAACTCACATTTCTGATGA
AGAAGCTAACTTGTTCGCTATGCAATTGGCTTCTGCTTCTGTTTTGCCAA
TGATTTTGAAGTCTGCTTTGGAATTGGATTTGTTGGAAATTATTGCTAAG
GCTGGTCCAGGTGCTCAAATTTCTCCAATTGAAATTGCTTCTCAATTGCC
AACTACTAACCCAGATGCTCCAGTTATGTTGGATAGAATGTTGAGATTGT
TGGCTTGTTACAACATTTTGACTTGTTCTGTTAGAACTCAACAAGATGGT
AAGGTTCAAAGATTGTACGGTTTGGCTACTGTTGCTAAGTACTTGGTTAA
GAACGAAGATGGTGTTTCTATTTCTGCTTTGAACTTGATGAACCAAGATA
AGGTTTTGATGGAATCTTGGTACCACTTGAAGGATGCTGTTTTGGATGGT
GGTATTCCATTCAACAAGGCTTACGGTATGACTGCTTTCGAATACCACGG
TACTGATCCAAGATTCAACAAGGTTTTCAACAAGGGTATGTCTGATCACT
CTACTATTACTATGAAGAAGATTTTGGAAACTTACACTGGTTTCGAAGGT
TTGAAGTCTTTGGTTGATGTTGGTGGTGGTACTGGTGCTGTTATTAACAC
TATTGTTTCTAAGTACCCAACTATTAAGGGTATTAACTTCGATTTGCCAC
ACGTTATTGAAGATGCTCCATCTTACCCAGGTGTTGAACACGTTGGTGGT
GATATGTTCGTTTCTATTCCAAAGGCTGATGCTGTTTTCATGAAGTGGAT
TTGTCACGATTGGTCTGATGAACACTGTTTGAAGTTCTTGAAGAACTGTT
ACGAAGCTTTGCCAGATAACGGTAAGGTTATTGTTGCTGAATGTATTTTG
CCAGTTGCTCCAGATTCTTCTTTGGCTACTAAGGGTGTTGTTCACATTGA
TGTTATTATGTTGGCTCACAACCCAGGTGGTAAGGAAAGAACTCAAAAGG
AATTCGAAGATTTGGCTAAGGGTGCTGGTTTCCAAGGTTTCAAGGTTCAC
TGTAACGCTTTCAACACTTACATTATGGAATTCTTGAAGAAGGTTTGA SEQ ID No 23:
Optinlized ADN *Rosa chinensis* caffeic acid O-
methyltransferase
ATGGGTTCTACTGGTGAAACTCAAATGACTCCAACTCAAGTTTCTGATGA
AGAAGCTAACTTGTTCGCTATGCAATTGGCTTCTGCTTCTGTTTTGCCAA
TGGTTTTGAAGGCTGCTATTGAATTGGATTTGTTGGAAATTATGGCTAAG
GCTGGTCCAGGTGCTTTCTTGTCTCCAAACGATTTGGCTTCTCAATTGCC
AACTAAGAACCCAGAAGCTCCAGTTATGTTGGATAGAATGTTGAGATTGT
TGGCTTCTTACTCTATTTTGACTTACTCTTTGAGAACTTTGCCAGATGGT
AAGGTTGAAAGATTGTACGGTTTGGGTCCAGTTTGTAAGTTCTTGACTAA
GAACGAAGATGGTGTTTCTATTGCTGCTTTGTGTTTGATGAACCAAGATA
AGGTTTTGGTTGAATCTTGGTACCACTTGAAGGATGCTGTTTTGGATGGT
GGTATTCCATTCAACAAGGCTTACGGTATGACTGCTTTCGATTACCACGG
TACTGATCCAAGATTCAACAAGGTTTTCAACAAGGGTATGGCTGATCACT
CTACTATTACTATGAAGAAGATTTTGGAAACTTACAAGGGTTTCGAAGGT
TTGACTTCTATTGTTGATGTTGGTGGTGGTACTGGTGCTGTTGTTAACAT
GATTGTTTCTAAGTACCCATCTATTAAGGGTATTAACTTCGATTTGCCAC
ACGTTATTGAAGATGCTCCACAATACCCAGGTGTTCAACACGTTGGTGGT
GATATGTTCGTTTCTGTTCCAAAGGGTGATGCTATTTTCATGAAGIGGAT
TTGTCACGATTGGTCTGATGAACACTGTTTGAAGTTCTTGAAGAACTGTT
ACGCTGCTTTGCCAGATAACGGTAAGGTTATTTTGGGTGAATGTATTTTG
CCAGTTGCTCCAGATACTTCTTTGGCTACTAAGGGTGTTGTTCACATTGA
TGTTATTATGTTGGCTCACAACCCAGGTGGTAAGGAAAGAACTGGTCAAG
AATTCGAAGCTTTGGCTAAGGGTTCTGGTTTCCAAGGTATTAGAGTTGCT
TGTAACGCTTTCAACACTTACGTTATTGAATTCTTGAAGAAGATTTAA SEQ ID No 24:
Optimized ADN *Vanilla planifolia* caffeic acid O-
methyltransferase
ATGGCTACTTGGGTTGAACACCAACAACAACAAAACGGTTCTAAGGATGT
TGATGAAGAAGCTTGTATGTACGCTATGCAATTGTCTTCTATGGTTGTTT
TGCCAATGACTTTGAGAGTTGCTGTTGAATTGGGTATTTTGGAACAAATT
CAAGCTGGTGGTCCAGATTCTTACTTGACTGCTGAAGATTTGGCTGCTAG
ATTGGGTAACTCTAACCCATTGGCTCCAGTTATGATTGAAAGAATTTTGA
GATTGTTGACTTCTTACTCTATTTTGAACTTCACTGATACTGTTGATGGT
GAAGGTAGAACTGTTAGATCTTACGGTGCTGCTCACGTTTGTAAGTACTT
GACTCCAAACCAAGATGGTGTTTCTATGGCTCCATTGGTTTTGATGAACA
CTGATAAGGTTTTGATGGAATCTTGGTACCACATGAAGGATGCTGTTACT
AACGGTGGTATTCCATTCAACTTGGCTTACGGTATGACTGCTTTCGAATA
CCACGGTAAGGATTTGAGATTCAACAAGGTTTTCAACGAAGGTATGAAGA
ACAACTCTATTATTATTACTAAGAAGATTTTGGAAAGATACAAGAGATTC
GAAGATGTTAACGTTTTGATTGATGTTGGTGGTGGTATTGGTGGTACTAT
TTCTATGATTACTGCTAAGTACCCACACATTCACGGTATTAACTTCGATT
TGCCACACGTTGTTTCTGAAGCTCCACCATTCCAAGGTGTTGAACACGTT -continued

SEQUENCE LISTING

GGTGGTAACATGTTCGAATCTGTTCCAATTGGTGATGCTATTTTCATTAA
GTGGATTTTGCACGATTGGTCTGATGAACACTGTTTGAAGTTGTTGAGAA
ACTGTGCTAAGTCTTTGCCAGATAAGGGTAAGGTTATTGTTGTTGAATGT
ATTTTGCCAGATGCTCCATTGGTTACTCCAGAAGCTGAAGGTGTTTTCCA
CTTGGATATGATTATGTTGGCTCACAACCCAGGTGGTAAGGAAAGAACTA
AGAAGGAATTCAAGGAATTGGCTATGTTGTCTGGTTTCTCTAACTTCAAG
GCTTTGTTCTCTTACGCTAACGTTTGGGTTATGGAATTCAACAAGTGA

SEQ ID No 25:
Optimized ADN *Homo sapiens* catechol acid O-methyltransferase
ATGCCGGAGGCCCCGCCTCTGCTGTTGGCAGCTGTGTTGCTGGGCCTGGT
GCTGCTGGTGGTGCTGCTGCTGCTTCTGAGGCACTGGGGCTGGGGCCTGT
GCCTTATCGGCTGGAACGAGTTCATCCTGCAGCCCATCCACAACCTGCTC
ATGGGTGACACCAAGGAGCAGCGCATCCTGAACCACGTGCTGCAGCATGC -continued

SEQUENCE LISTING

GGAGCCCGGGAACGCACAGAGCGTGCTGGAGGCCATTGACACCTACTGCG
AGCAGAAGGAGTGGGCCATGAACGTGGGCGACAAGAAAGGCAAGATCGTG
GACGCCGTGATTCAGGAGCACCAGCCCTCCGTGCTGCTGGAGCTGGGGGC
CTACTGTGGCTACTCAGCTGTGCGCATGGCCCGCCTGCTGTCACCAGGGG
CGAGGCTCATCACCATCGAGATCAACCCCGACTGTGCCGCCATCACCCAG
CGGATGGTGGATTTCGCTGGCGTGAAGGACAAGGTCACCCTTGTGGTTGG
AGCGTCCCAGGACATCATCCCCCAGCTGAAGAAGAAGTATGATGTGGACA
CACTGGACATGGTCTTCCTCGACCACTGGAAGGACCGGTACCTGCCGGAC
ACGCTTCTCTTGGAGGAATGTGGCCTGCTGCGGAAGGGGACAGTGCTACT
GGCTGACAACGTGATCTGCCCAGGTGCGCCAGACTTCCTAGCACACGTGC
GCGGGAGCAGCTGCTTTGAGTGCACACACTACCAATCGTTCCTGGAATAC
AGGGAGGTGGTGGACGGCCTGGAGAAGGCCATCTACAAGGGCCCAGGCAG
CGAAGCAGGGCCTTAA

The invention claimed is:

1. A method for producing a substantially pure vanilloid of formula (I):

(I)

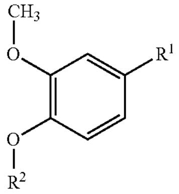

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3$COOH; —$CH_2$NHC(═O)$R^3$; wherein $R^3$ is a lower alkyl, $R^2$ being different from a methyl (—$CH_3$), comprising the steps of:

a) providing a recombinant unicellular host capable of producing said vanilloid, wherein said recombinant host expresses at least a nucleic acid coding for a 3-dehydroshikimate dehydratase (3DSD) and at least a nucleic acid coding for an aromatic carboxylic acid reductase (ACAR);

b) cultivating said host in a suitable medium; and c) recovering the produced vanilloid from said host or from the culture supernatant thereof, wherein said recombinant host expresses at least a nucleic acid coding for a caffeic acid 3-O-methyltransferase polypeptide that is suitable for methylating selectively the 3-OH of a protocatechuic aldehyde.

2. The method according to claim 1, wherein said recombinant host expresses at least a nucleic acid coding for a caffeic acid 3-O-methyltransferase polypeptide from *Medicago sativa, Rosa chinensis*, and/or *Vanilla planifolia.*

3. The method according to claim 1, wherein in said vanilloid of formula (I), $R^2$ is H.

4. The method according to claim 1, wherein in said vanilloid of formula (I), $R^1$ is —CHO.

5. The method according to claim 1, wherein the caffeic acid 3-O-methyltransferase polypeptide comprises a sequence selected from SEQ ID NO: 1, 2 or 3.

6. The method according to claim 1, wherein said recombinant host expresses at least a nucleic acid coding for a phosphopantetheinyl transferase (PPTase).

7. The method according to claim 1, wherein said recombinant host is a recombinant unicellular microorganism selected from a bacterium, an archaeon, a yeast, a protozoon, an alga, and a fungus.

8. The method according to claim 7, wherein said recombinant host is selected from *Saccharomyces cerevisiae* and *Schizosaccharomyces pombe.*

9. The method according to claim 8, wherein said recombinant host is *Saccharomyces cerevisiae* and expresses at least a nucleic acid encoding a 3-dehydroshikimate dehydratase (3DSD), at least a nucleic acid encoding an aromatic carboxylic acid reductase (ACAR), and at least a nucleic acid encoding a phosphopantetheinyl transferase (PPTase).

10. The method according to claim 1, wherein said recombinant host does not express a functional alcohol dehydrogenase ADH6.

11. The method according to claim 1, wherein said suitable medium comprises at least one compound selected from glucose, galactose, fructose, arabinose, lactose, mannose, erythrose-4-phosphate, dehydroshikimic acid, catechol, protocatechuic acid, protocatechuic aldehyde, ethanol, glycerol and derivatives thereof.

12. The method according to claim 1, wherein said suitable medium does not comprise aromatic amino acids.

13. A yeast suitable for producing a substantially pure vanilloid of formula (I):

(I)

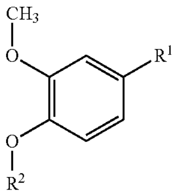

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3$COOH; —$CH_2$NHC(═O)$R^3$; wherein $R^3$ is a lower alkyl, $R^2$ being different from a methyl (—$CH_3$), expressing at least a nucleic acid coding for an aromatic carboxylic acid reductase (ACAR) and a 3-dehydroshikimate dehydratase (3DSD), wherein said yeast expresses at least a nucleic acid coding for a caffeic acid 3-O-methyltransferase polypeptide that is suitable for methylating selectively the 3-OH of a protocatechuic aldehyde.

14. A method for converting a protocatechuic aldehyde into a substantially pure vanilloid of formula (I):

(I)

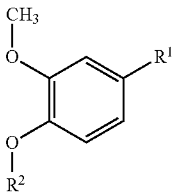

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, $R^2$ being different from a methyl (—$CH_3$), and comprising the steps of:

a) providing a recombinant unicellular host capable of producing said vanilloid, wherein said recombinant host expresses at least a nucleic acid coding for an aromatic carboxylic acid reductase (ACAR) and does not express nucleic acids coding for the following enzymes: a phenylalanine ammonia lyase (PAL) or a tyrosine ammonia lyase (TAL) or a phenylalanine/tyrosine ammonia lyase (PAL/TAL), a coA ligase, and a crotonase;

b) cultivating said host in a suitable medium; and c) recovering the produced vanilloid from said host or from the culture supernatant thereof, wherein said recombinant host expresses at least a nucleic acid coding for a caffeic acid 3-O-methyltransferase polypeptide that is suitable for methylating selectively the 3-OH of a protocatechuic aldehyde.

15. A method for converting a protocatechuic aldehyde into a substantially pure vanilloid of formula (I):

(I)

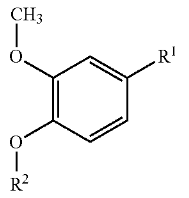

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, $R^2$ being different from a methyl (—$CH_3$), and comprising the steps of:

a) providing a recombinant unicellular host capable of producing said vanilloid, wherein said recombinant host expresses at least a nucleic acid coding for an aromatic carboxylic acid reductase (ACAR) and at least one nucleic acid coding for a 3-dehydroshikimate dehydratase (3DSD);

b) cultivating said host in a suitable medium; and c) recovering the produced vanilloid from said host or from the culture supernatant thereof, wherein said recombinant host expresses at least a nucleic acid coding for a caffeic acid 3-O-methyltransferase polypeptide that is suitable for methylating selectively the 3-OH of a protocatechuic aldehyde.

16. A yeast suitable for converting a protocatechuic aldehyde into a substantially pure vanilloid of formula (I):

(I)

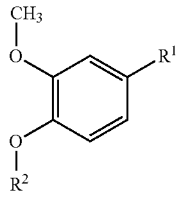

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, $R^2$ being different from a methyl (—$CH_3$), expressing at least a nucleic acid coding for an aromatic carboxylic acid reductase (ACAR), wherein said yeast expresses at least a nucleic acid coding for a caffeic acid 3-O-methyltransferase polypeptide that is suitable for methylating selectively the 3-OH of a protocatechuic aldehyde, and does not express nucleic acids coding for the following enzymes: a phenylalanine ammonia lyase (PAL) or a tyrosine ammonia lyase (TAL) or a phenylalanine/tyrosine ammonia lyase (PAL/TAL), a coA ligase, and a crotonase.

17. A yeast suitable for converting a protocatechuic aldehyde into a substantially pure vanilloid of formula (I):

(I)

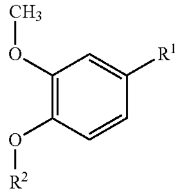

$R^1$ being selected from the group consisting of —CHO; —COOH; —$COOR^3$; —$CH_2OH$; —$CH_2COOH$; —C(═O)$CH_3$; —$CR^3$(OH)COOH; —$CHR^3COOH$; —$CH_2NHC$(═O)$R^3$; wherein $R^3$ is a lower alkyl, $R^2$ being different from a methyl (—$CH_3$), expressing at least a nucleic acid coding for an aromatic carboxylic acid reductase (ACAR) and at least a nucleic acid coding for a 3-dehydroshikimate dehydratase (3DSD), wherein said yeast expresses at least a nucleic acid coding for a caffeic acid 3-O-methyltransferase polypeptide that is suitable for methylating selectively the 3-OH of a protocatechuic aldehyde.

18. A composition comprising a vanilloid obtained by the method according to claim 1.

19. A method for providing a flavor or a fragrance to a composition, comprising a step of producing a substantially pure vanilloid in said composition by the method according to claim 1.

20. A composition comprising a vanilloid obtained by the method according to claim 14.

21. A composition comprising a vanilloid obtained by the method according to claim 15.

22. A method for providing a flavor or a fragrance, comprising a step of producing a composition comprising a vanilloid obtained by the method according to claim 14.

23. A method for providing a flavor or a fragrance, comprising a step of producing a composition comprising a vanilloid obtained by the method according to claim 15.

* * * * *

SEQUENCE LISTING

```
<160> NUMBER OF SEQ ID NOS: 25

<210> SEQ ID NO 1
<211> LENGTH: 365
<212> TYPE: PRT
<213> ORGANISM: Medicago sativa

<400> SEQUENCE: 1

Met Gly Ser Thr Gly Glu Thr Gln Ile Thr Pro Thr His Ile Ser Asp
1               5                   10                  15

Glu Glu Ala Asn Leu Phe Ala Met Gln Leu Ala Ser Ala Ser Val Leu
            20                  25                  30

Pro Met Ile Leu Lys Ser Ala Leu Glu Leu Asp Leu Leu Glu Ile Ile
        35                  40                  45

Ala Lys Ala Gly Pro Gly Ala Gln Ile Ser Pro Ile Glu Ile Ala Ser
    50                  55                  60

Gln Leu Pro Thr Thr Asn Pro Asp Ala Pro Val Met Leu Asp Arg Met
65                  70                  75                  80

Leu Arg Leu Leu Ala Cys Tyr Asn Ile Leu Thr Cys Ser Val Arg Thr
                85                  90                  95

Gln Gln Asp Gly Lys Val Gln Arg Leu Tyr Gly Leu Ala Thr Val Ala
            100                 105                 110

Lys Tyr Leu Val Lys Asn Glu Asp Gly Val Ser Ile Ser Ala Leu Asn
        115                 120                 125

Leu Met Asn Gln Asp Lys Val Leu Met Glu Ser Trp Tyr His Leu Lys
    130                 135                 140

Asp Ala Val Leu Asp Gly Gly Ile Pro Phe Asn Lys Ala Tyr Gly Met
145                 150                 155                 160

Thr Ala Phe Glu Tyr His Gly Thr Asp Pro Arg Phe Asn Lys Val Phe
                165                 170                 175

Asn Lys Gly Met Ser Asp His Ser Thr Ile Thr Met Lys Lys Ile Leu
            180                 185                 190

Glu Thr Tyr Thr Gly Phe Glu Gly Leu Lys Ser Leu Val Asp Val Gly
        195                 200                 205

Gly Gly Thr Gly Ala Val Ile Asn Thr Ile Val Ser Lys Tyr Pro Thr
    210                 215                 220

Ile Lys Gly Ile Asn Phe Asp Leu Pro His Val Ile Glu Asp Ala Pro
225                 230                 235                 240

Ser Tyr Pro Gly Val Glu His Val Gly Gly Asp Met Phe Val Ser Ile
                245                 250                 255
```

```
Pro Lys Ala Asp Ala Val Phe Met Lys Trp Ile Cys His Asp Trp Ser
            260                 265                 270

Asp Glu His Cys Leu Lys Phe Leu Lys Asn Cys Tyr Glu Ala Leu Pro
        275                 280                 285

Asp Asn Gly Lys Val Ile Val Ala Glu Cys Ile Leu Pro Val Ala Pro
    290                 295                 300

Asp Ser Ser Leu Ala Thr Lys Gly Val Val His Ile Asp Val Ile Met
305                 310                 315                 320

Leu Ala His Asn Pro Gly Gly Lys Glu Arg Thr Gln Lys Glu Phe Glu
                325                 330                 335

Asp Leu Ala Lys Gly Ala Gly Phe Gln Gly Phe Lys Val His Cys Asn
            340                 345                 350

Ala Phe Asn Thr Tyr Ile Met Glu Phe Leu Lys Lys Val
        355                 360                 365


<210> SEQ ID NO 2
<211> LENGTH: 365
<212> TYPE: PRT
<213> ORGANISM: Rosa chinensis

<400> SEQUENCE: 2

Met Gly Ser Thr Gly Glu Thr Gln Met Thr Pro Thr Gln Val Ser Asp
1               5                   10                  15

Glu Glu Ala Asn Leu Phe Ala Met Gln Leu Ala Ser Ala Ser Val Leu
            20                  25                  30

Pro Met Val Leu Lys Ala Ala Ile Glu Leu Asp Leu Leu Glu Ile Met
        35                  40                  45

Ala Lys Ala Gly Pro Gly Ala Phe Leu Ser Pro Asn Asp Leu Ala Ser
    50                  55                  60

Gln Leu Pro Thr Lys Asn Pro Glu Ala Pro Val Met Leu Asp Arg Met
65                  70                  75                  80

Leu Arg Leu Leu Ala Ser Tyr Ser Ile Leu Thr Tyr Ser Leu Arg Thr
                85                  90                  95

Leu Pro Asp Gly Lys Val Glu Arg Leu Tyr Gly Leu Gly Pro Val Cys
            100                 105                 110

Lys Phe Leu Thr Lys Asn Glu Asp Gly Val Ser Ile Ala Ala Leu Cys
        115                 120                 125

Leu Met Asn Gln Asp Lys Val Leu Val Glu Ser Trp Tyr His Leu Lys
    130                 135                 140

Asp Ala Val Leu Asp Gly Gly Ile Pro Phe Asn Lys Ala Tyr Gly Met
145                 150                 155                 160

Thr Ala Phe Asp Tyr His Gly Thr Asp Pro Arg Phe Asn Lys Val Phe
                165                 170                 175

Asn Lys Gly Met Ala Asp His Ser Thr Ile Thr Met Lys Lys Ile Leu
            180                 185                 190

Glu Thr Tyr Lys Gly Phe Glu Gly Leu Thr Ser Ile Val Asp Val Gly
        195                 200                 205

Gly Gly Thr Gly Ala Val Val Asn Met Ile Val Ser Lys Tyr Pro Ser
    210                 215                 220

Ile Lys Gly Ile Asn Phe Asp Leu Pro His Val Ile Glu Asp Ala Pro
225                 230                 235                 240

Gln Tyr Pro Gly Val Gln His Val Gly Gly Asp Met Phe Val Ser Val
                245                 250                 255

Pro Lys Gly Asp Ala Ile Phe Met Lys Trp Ile Cys His Asp Trp Ser
```

-continued

```
            260                 265                 270

Asp Glu His Cys Leu Lys Phe Leu Lys Asn Cys Tyr Ala Ala Leu Pro
        275                 280                 285

Asp Asn Gly Lys Val Ile Leu Gly Glu Cys Ile Leu Pro Val Ala Pro
    290                 295                 300

Asp Thr Ser Leu Ala Thr Lys Gly Val Val His Ile Asp Val Val Met
305                 310                 315                 320

Leu Ala His Asn Pro Gly Gly Lys Glu Arg Thr Glu Gln Glu Phe Glu
                325                 330                 335

Ala Leu Ala Lys Gly Ser Gly Phe Gln Gly Ile Arg Val Ala Cys Asn
            340                 345                 350

Ala Phe Asn Thr Tyr Val Ile Glu Phe Leu Lys Lys Ile
        355                 360                 365


<210> SEQ ID NO 3
<211> LENGTH: 365
<212> TYPE: PRT
<213> ORGANISM: Vanilla planifolia

<400> SEQUENCE: 3

Met Ala Thr Trp Val Glu His Gln Gln Gln Gln Asn Gly Ser Lys Asp
1               5                   10                  15

Val Asp Glu Glu Ala Cys Met Tyr Ala Met Gln Leu Ser Ser Met Val
            20                  25                  30

Val Leu Pro Met Thr Leu Arg Val Ala Val Glu Leu Gly Ile Leu Glu
        35                  40                  45

Gln Ile Gln Ala Gly Gly Pro Asp Ser Tyr Leu Thr Ala Glu Asp Leu
    50                  55                  60

Ala Ala Arg Leu Gly Asn Ser Asn Pro Leu Ala Pro Val Met Ile Glu
65                  70                  75                  80

Arg Ile Leu Arg Leu Leu Thr Ser Tyr Ser Ile Leu Asn Phe Thr Asp
                85                  90                  95

Thr Val Asp Gly Glu Gly Arg Thr Val Arg Ser Tyr Gly Ala Ala His
            100                 105                 110

Val Cys Lys Tyr Leu Thr Pro Asn Gln Asp Gly Val Ser Met Ala Pro
        115                 120                 125

Leu Val Leu Met Asn Thr Asp Lys Val Leu Met Glu Ser Trp Tyr His
    130                 135                 140

Met Lys Asp Ala Val Thr Asn Gly Gly Ile Pro Phe Asn Leu Ala Tyr
145                 150                 155                 160

Gly Met Thr Ala Phe Glu Tyr His Gly Lys Asp Leu Arg Phe Asn Lys
                165                 170                 175

Val Phe Asn Glu Gly Met Lys Asn Asn Ser Ile Ile Ile Thr Lys Lys
            180                 185                 190

Ile Leu Glu Arg Tyr Lys Arg Phe Glu Asp Val Asn Val Leu Ile Asp
        195                 200                 205

Val Gly Gly Gly Ile Gly Gly Thr Ile Ser Met Ile Thr Ala Lys Tyr
    210                 215                 220

Pro His Ile His Gly Ile Asn Phe Asp Leu Pro His Val Val Ser Glu
225                 230                 235                 240

Ala Pro Pro Phe Gln Gly Val Glu His Val Gly Gly Asn Met Phe Glu
                245                 250                 255

Ser Val Pro Ile Gly Asp Ala Ile Phe Ile Lys Trp Ile Leu His Asp
            260                 265                 270
```

-continued

```
Trp Ser Asp Glu His Cys Leu Lys Leu Leu Arg Asn Cys Ala Lys Ser
        275                 280                 285

Leu Pro Asp Lys Gly Lys Val Ile Val Val Glu Cys Ile Leu Pro Asp
    290                 295                 300

Ala Pro Leu Val Thr Pro Glu Ala Glu Gly Val Phe His Leu Asp Met
305                 310                 315                 320

Ile Met Leu Ala His Asn Pro Gly Gly Lys Glu Arg Thr Lys Lys Glu
                325                 330                 335

Phe Lys Glu Leu Ala Met Leu Ser Gly Phe Ser Asn Phe Lys Ala Leu
            340                 345                 350

Phe Ser Tyr Ala Asn Val Trp Val Met Glu Phe Asn Lys
        355                 360                 365


<210> SEQ ID NO 4
<211> LENGTH: 271
<212> TYPE: PRT
<213> ORGANISM: Homo sapiens

<400> SEQUENCE: 4

Met Pro Glu Ala Pro Pro Leu Leu Leu Ala Ala Val Leu Leu Gly Leu
1               5                   10                  15

Val Leu Leu Val Val Leu Leu Leu Leu Leu Arg His Trp Gly Trp Gly
            20                  25                  30

Leu Cys Leu Ile Gly Trp Asn Glu Phe Ile Leu Gln Pro Ile His Asn
        35                  40                  45

Leu Leu Met Gly Asp Thr Lys Glu Gln Arg Ile Leu Asn His Val Leu
    50                  55                  60

Gln His Ala Glu Pro Gly Asn Ala Gln Ser Val Leu Glu Ala Ile Asp
65                  70                  75                  80

Thr Tyr Cys Glu Gln Lys Glu Trp Ala Met Asn Val Gly Asp Lys Lys
                85                  90                  95

Gly Lys Ile Val Asp Ala Val Ile Gln Glu His Gln Pro Ser Val Leu
            100                 105                 110

Leu Glu Leu Gly Ala Tyr Cys Gly Tyr Ser Ala Val Arg Met Ala Arg
        115                 120                 125

Leu Leu Ser Pro Gly Ala Arg Leu Ile Thr Ile Glu Ile Asn Pro Asp
    130                 135                 140

Cys Ala Ala Ile Thr Gln Arg Met Val Asp Phe Ala Gly Val Lys Asp
145                 150                 155                 160

Lys Val Thr Leu Val Val Gly Ala Ser Gln Asp Ile Ile Pro Gln Leu
                165                 170                 175

Lys Lys Lys Tyr Asp Val Asp Thr Leu Asp Met Val Phe Leu Asp His
            180                 185                 190

Trp Lys Asp Arg Tyr Leu Pro Asp Thr Leu Leu Leu Glu Glu Cys Gly
        195                 200                 205

Leu Leu Arg Lys Gly Thr Val Leu Leu Ala Asp Asn Val Ile Cys Pro
    210                 215                 220

Gly Ala Pro Asp Phe Leu Ala His Val Arg Gly Ser Ser Cys Phe Glu
225                 230                 235                 240

Cys Thr His Tyr Gln Ser Phe Leu Glu Tyr Arg Glu Val Val Asp Gly
                245                 250                 255

Leu Glu Lys Ala Ile Tyr Lys Gly Pro Gly Ser Glu Ala Gly Pro
            260                 265                 270
```

<210> SEQ ID NO 5
<211> LENGTH: 1098
<212> TYPE: DNA
<213> ORGANISM: Medicago sativa

<400> SEQUENCE: 5
atgggttcaa caggtgaaac tcaaataaca ccaacccaca tatcagatga agaagcaaac 60
ctcttcgcca tgcaactagc aagtgcttca gttcttccca tgattttgaa atcagctctt 120
gaacttgatc tcttagaaat cattgctaaa gctggacctg gtgctcaaat ttcacctatt 180
gaaattgctt ctcagcttcc aacaactaac cctgatgcac cagtcatgtt ggaccgaatg 240
ttgcgtctct tggcttgtta caatatcctc acttgttctg ttcgtactca acaagatgga 300
aaggttcaga gactttacgg tttggctact gttgctaagt atttggttaa gaatgaagat 360
ggtgtttcta tttctgctct taatctcatg aatcaggata aagtgctcat ggaaagctgg 420
taccacctaa aagatgcagt ccttgatggg ggcattccat tcaacaaggc ttatggaatg 480
acagcctttg aataccatgg aacagatcca aggtttaaca aggttttcaa caaggggatg 540
tctgatcact ctaccatcac aatgaagaaa attcttgaga cctacacagg ttttgaaggc 600
cttaaatctc ttgttgatgt aggtggtggt accggagctg taattaacac gattgtctca 660
aaatatccca ctattaaggg tattaatttt gatttacccc atgtcattga agatgctcca 720
tcttatccag gagttgagca tgttggtgga gacatgtttg tcagtattcc aaaggctgat 780
gctgttttta tgaagtggat ttgtcatgac tggagtgatg agcactgctt gaaatttttg 840
aagaactgct atgaggcact gccagacaat ggaaaagtga ttgtggcaga atgcatactt 900
ccagtggctc cagattcaag cctggccaca aaaggtgtgg ttcacattga tgtgatcatg 960
ttggctcata atccaggtgg gaaagagaga acacaaaaag agtttgagga tcttgccaaa 1020
ggtgctggat tccaaggttt caaagtccat tgtaatgctt tcaacacata catcatggag 1080
tttcttaaga aggtttaa 1098

<210> SEQ ID NO 6
<211> LENGTH: 1098
<212> TYPE: DNA
<213> ORGANISM: Rosa chinensis

<400> SEQUENCE: 6
atgggttcaa ccggcgagac tcagatgact ccgacccaag tctccgacga ggaagccaac 60
ctcttcgcca tgcaactcgc cagcgcctcc gtcctcccca tggttctcaa agccgccatt 120
gagctcgacc tcttggagat catggccaag gccggacccg gcgcgttcct ctcccctaat 180
gacctagcct ctcagcttcc gaccaagaac cccgaagctc cagtcatgct tgaccggatg 240
cttcgccttc tggccagcta ctccattcta acctactcct tgcgtacact tccggacggc 300
aaagttgaga ggctctacgg tttgggacct gtgtgtaaat tcttgaccaa gaacgaagat 360
ggtgtctcca ttgctgctct ctgcctcatg aaccaagaca aggtcctcgt cgagagctgg 420
tatcatctaa aggatgcagt tcttgatggt gggattccat ttaacaaggc ctatggaatg 480
actgcttttg attaccatgg aactgaccct agattcaaca aggtcttcaa caagggaatg 540
gctgaccact ccaccattac catgaagaaa atccttgaga cttataaagg ctttgagggc 600
ctcacatcca tcgttgatgt cggaggcggc accggagctg ttgttaacat gatcgtttct 660
aagtaccctt cgatcaaggg catcaacttt gacttgcctc atgtgatcga agatgctcct 720

-continued caatatcctg gtgtgcaaca tgttggaggg gacatgtttg taagtgtacc gaaaggagat 780
gcaattttca tgaagtggat atgtcacgac tggagtgacg agcactgctt gaaattcttg 840
aagaattgct atgcagcgct tccagacaat gggaaagtga ttcttggtga gtgcattctg 900
ccggtagcac cggacactag cctcgccacc aagggagttg tccatatcga cgtggtcatg 960
ttggctcaca accccggtgg caaagagagg acggagcagg agtttgaagc cctggctaag 1020
gggtctggat ttcaaggcat tcgagtagca tgtaatgctt tcaacaccta tgtcatcgaa 1080
tttcttaaga agatctga 1098

<210> SEQ ID NO 7
<211> LENGTH: 1098
<212> TYPE: DNA
<213> ORGANISM: Vanilla planifolia

<400> SEQUENCE: 7
atggctacat gggtggagca ccaacagcag caaaatggat ccaaggacgt ggacgaggag 60
gcgtgcatgt acgccatgca gttgtcgagc atggtcgtcc tcccgatgac gcttagggta 120
gccgtcgagc tcggcatact cgaacaaatc caggccgggg gcccagattc gtaccttact 180
gccgaggatt tggcggcgag gctcggcaac tccaacccct tagctccggt catgatcgag 240
cggatcctgc gcctgctcac cagctactcc atccttaact tcaccgacac cgtcgacggg 300
gagggtagga ccgtccggag ctacggcgcg gcgcatgtct gcaagtacct gactcccaac 360
caggacggcg tctccatggc gcctctcgtc ctcatgaaca cggataaggt ccttatggag 420
agctggtacc acatgaagga tgcagtgaca aatggtggaa taccattcaa tctagcatat 480
gggatgacag cttttgagta tcatgggaaa gatctaaggt ttaataaggt gttcaacgag 540
ggcatgaaga acaactcgat cattataacg aagaagattt tagagagata caaaaggttt 600
gaagatgtca atgttttaat tgatgttggt ggtggaattg gtggaactat cagtatgatt 660
actgcaaagt atccacatat acatgggatt aattttgacc ttcctcatgt tgtttctgaa 720
gctccacctt tccaaggggt agaacatgtc ggtggaaaca tgtttgaaag tgtccccatt 780
ggtgatgcaa tcttcataaa gtggattctt catgattgga gtgatgagca ttgtttgaag 840
ctcctaagaa attgtgcaaa atctttacct gacaaaggaa aagtcatagt tgtggaatgc 900
attcttcccg atgcaccttt ggtgacgcca gaggctgaag gtgtctttca tttggacatg 960
ataatgttgg ctcacaatcc tggggggaaag gagagaacaa agaaagagtt taaagaattg 1020
gctatgctat ctggtttctc taatttcaag gcacttttta gttatgctaa tgtttgggtc 1080
atggaattca acaaatag 1098

<210> SEQ ID NO 8
<211> LENGTH: 816
<212> TYPE: DNA
<213> ORGANISM: Homo sapiens

<400> SEQUENCE: 8
atgccggagg ccccgcctct gctgttggca gctgtgttgc tgggcctggt gctgctggtg 60
gtgctgctgc tgcttctgag gcactggggc tggggcctgt gccttatcgg ctggaacgag 120
ttcatcctgc agcccatcca caacctgctc atgggtgaca ccaaggagca gcgcatcctg 180
aaccatgtgc tgcagcatgc ggagcccggg aacgcacaga gcgtgctgga ggccattgac 240
acctactgcg agcagaagga gtgggccatg aacgtgggcg acaagaaagg caagatcgtg 300
gacgccgtga ttcaggagca ccagccctcc gtgctgctgg agctgggggc ctactgtggc 360

```
tactcagctg tgcgcatggc ccgcctgctg tcaccagggg cgaggctcat caccatcgag    420

atcaaccccg actgtgccgc catcacccag cggatggtgg atttcgctgg catgaaggac    480

aaggtcaccc ttgtggttgg agcgtcccag gacatcatcc cccagctgaa gaagaagtat    540

gatgtggaca cactggacat ggtcttcctc gaccactgga aggaccggta cctgccggac    600

acgcttctct tggaggaatg tggcctgctg cggaagggga cagtgctact ggctgacaac    660

gtgatctgcc caggtgcgcc agacttccta gcacacgtgc gcgggagcag ctgctttgag    720

tgcacacact accaatcgtt cctggaatac agggaggtgg tggacggcct ggagaaggcc    780

atctacaagg gcccaggcag cgaagcaggg ccctga                              816
```

<210> SEQ ID NO 9
<211> LENGTH: 481
<212> TYPE: PRT
<213> ORGANISM: Arabidopsis thaliana

<400> SEQUENCE: 9

```
Met His Ile Thr Lys Pro His Ala Ala Met Phe Ser Ser Pro Gly Met
1               5                   10                  15

Gly His Val Ile Pro Val Ile Glu Leu Gly Lys Arg Leu Ser Ala Asn
            20                  25                  30

Asn Gly Phe His Val Thr Val Phe Val Leu Glu Thr Asp Ala Ala Ser
        35                  40                  45

Ala Gln Ser Lys Phe Leu Asn Ser Thr Gly Val Asp Ile Val Lys Leu
    50                  55                  60

Pro Ser Pro Asp Ile Tyr Gly Leu Val Asp Pro Asp Asp His Val Val
65                  70                  75                  80

Thr Lys Ile Gly Val Ile Met Arg Ala Ala Val Pro Ala Leu Arg Ser
                85                  90                  95

Lys Ile Ala Ala Met His Gln Lys Pro Thr Ala Leu Ile Val Asp Leu
            100                 105                 110

Phe Gly Thr Asp Ala Leu Cys Leu Ala Lys Glu Phe Asn Met Leu Ser
        115                 120                 125

Tyr Val Phe Ile Pro Thr Asn Ala Arg Phe Leu Gly Val Ser Ile Tyr
    130                 135                 140

Tyr Pro Asn Leu Asp Lys Asp Ile Lys Glu Glu His Thr Val Gln Arg
145                 150                 155                 160

Asn Pro Leu Ala Ile Pro Gly Cys Glu Pro Val Arg Phe Glu Asp Thr
                165                 170                 175

Leu Asp Ala Tyr Leu Val Pro Asp Glu Pro Val Tyr Arg Asp Phe Val
            180                 185                 190

Arg His Gly Leu Ala Tyr Pro Lys Ala Asp Gly Ile Leu Val Asn Thr
        195                 200                 205

Trp Glu Glu Met Glu Pro Lys Ser Leu Lys Ser Leu Leu Asn Pro Lys
    210                 215                 220

Leu Leu Gly Arg Val Ala Arg Val Pro Val Tyr Pro Ile Gly Pro Leu
225                 230                 235                 240

Cys Arg Pro Ile Gln Ser Ser Glu Thr Asp His Pro Val Leu Asp Trp
                245                 250                 255

Leu Asn Glu Gln Pro Asn Glu Ser Val Leu Tyr Ile Ser Phe Gly Ser
            260                 265                 270

Gly Gly Cys Leu Ser Ala Lys Gln Leu Thr Glu Leu Ala Trp Gly Leu
        275                 280                 285
```

Glu Gln Ser Gln Gln Arg Phe Val Trp Val Val Arg Pro Pro Val Asp
    290                 295                 300

Gly Ser Cys Cys Ser Glu Tyr Val Ser Ala Asn Gly Gly Gly Thr Glu
305                 310                 315                 320

Asp Asn Thr Pro Glu Tyr Leu Pro Glu Gly Phe Val Ser Arg Thr Ser
                325                 330                 335

Asp Arg Gly Phe Val Val Pro Ser Trp Ala Pro Gln Ala Glu Ile Leu
            340                 345                 350

Ser His Arg Ala Val Gly Gly Phe Leu Thr His Cys Gly Trp Ser Ser
        355                 360                 365

Thr Leu Glu Ser Val Val Gly Gly Val Pro Met Ile Ala Trp Pro Leu
    370                 375                 380

Phe Ala Glu Gln Asn Met Asn Ala Ala Leu Leu Ser Asp Glu Leu Gly
385                 390                 395                 400

Ile Ala Val Arg Leu Asp Asp Pro Lys Glu Asp Ile Ser Arg Trp Lys
                405                 410                 415

Ile Glu Ala Leu Val Arg Lys Val Met Thr Glu Lys Glu Gly Glu Ala
            420                 425                 430

Met Arg Arg Lys Val Lys Lys Leu Arg Asp Ser Ala Glu Met Ser Leu
        435                 440                 445

Ser Ile Asp Gly Gly Gly Leu Ala His Glu Ser Leu Cys Arg Val Thr
    450                 455                 460

Lys Glu Cys Gln Arg Phe Leu Glu Arg Val Val Asp Leu Ser Arg Gly
465                 470                 475                 480

Ala

<210> SEQ ID NO 10
<211> LENGTH: 480
<212> TYPE: PRT
<213> ORGANISM: Arabidopsis thaliana

<400> SEQUENCE: 10

Met Glu Glu Ser Lys Thr Pro His Val Ala Ile Ile Pro Ser Pro Gly
1               5                   10                  15

Met Gly His Leu Ile Pro Leu Val Glu Phe Ala Lys Arg Leu Val His
            20                  25                  30

Leu His Gly Leu Thr Val Thr Phe Val Ile Ala Gly Glu Gly Pro Pro
        35                  40                  45

Ser Lys Ala Gln Arg Thr Val Leu Asp Ser Leu Pro Ser Ser Ile Ser
    50                  55                  60

Ser Val Phe Leu Pro Pro Val Asp Leu Thr Asp Leu Ser Ser Ser Thr
65                  70                  75                  80

Arg Ile Glu Ser Arg Ile Ser Leu Thr Val Thr Arg Ser Asn Pro Glu
                85                  90                  95

Leu Arg Lys Val Phe Asp Ser Phe Val Glu Gly Gly Arg Leu Pro Thr
            100                 105                 110

Ala Leu Val Val Asp Leu Phe Gly Thr Asp Ala Phe Asp Val Ala Val
        115                 120                 125

Glu Phe His Val Pro Pro Tyr Ile Phe Tyr Pro Thr Thr Ala Asn Val
    130                 135                 140

Leu Ser Phe Phe Leu His Leu Pro Lys Leu Asp Glu Thr Val Ser Cys
145                 150                 155                 160

Glu Phe Arg Glu Leu Thr Glu Pro Leu Met Leu Pro Gly Cys Val Pro
                165                 170                 175

-continued

```
Val Ala Gly Lys Asp Phe Leu Asp Pro Ala Gln Asp Arg Lys Asp Asp
            180                 185                 190

Ala Tyr Lys Trp Leu Leu His Asn Thr Lys Arg Tyr Lys Glu Ala Glu
        195                 200                 205

Gly Ile Leu Val Asn Thr Phe Phe Glu Leu Glu Pro Asn Ala Ile Lys
    210                 215                 220

Ala Leu Gln Glu Pro Gly Leu Asp Lys Pro Pro Val Tyr Pro Val Gly
225                 230                 235                 240

Pro Leu Val Asn Ile Gly Lys Gln Glu Ala Lys Gln Thr Glu Glu Ser
                245                 250                 255

Glu Cys Leu Lys Trp Leu Asp Asn Gln Pro Leu Gly Ser Val Leu Tyr
            260                 265                 270

Val Ser Phe Gly Ser Gly Gly Thr Leu Thr Cys Glu Gln Leu Asn Glu
        275                 280                 285

Leu Ala Leu Gly Leu Ala Asp Ser Glu Gln Arg Phe Leu Trp Val Ile
    290                 295                 300

Arg Ser Pro Ser Gly Ile Ala Asn Ser Ser Tyr Phe Asp Ser His Ser
305                 310                 315                 320

Gln Thr Asp Pro Leu Thr Phe Leu Pro Pro Gly Phe Leu Glu Arg Thr
                325                 330                 335

Lys Lys Arg Gly Phe Val Ile Pro Phe Trp Ala Pro Gln Ala Gln Val
            340                 345                 350

Leu Ala His Pro Ser Thr Gly Gly Phe Leu Thr His Cys Gly Trp Asn
        355                 360                 365

Ser Thr Leu Glu Ser Val Val Ser Gly Ile Pro Leu Ile Ala Trp Pro
    370                 375                 380

Leu Tyr Ala Glu Gln Lys Met Asn Ala Val Leu Leu Ser Glu Asp Ile
385                 390                 395                 400

Arg Ala Ala Leu Arg Pro Arg Ala Gly Asp Asp Gly Leu Val Arg Arg
                405                 410                 415

Glu Glu Val Ala Arg Val Val Lys Gly Leu Met Glu Gly Glu Glu Gly
            420                 425                 430

Lys Gly Val Arg Asn Lys Met Lys Glu Leu Lys Glu Ala Ala Cys Arg
        435                 440                 445

Val Leu Lys Asp Asp Gly Thr Ser Thr Lys Ala Leu Ser Leu Val Ala
    450                 455                 460

Leu Lys Trp Lys Ala His Lys Lys Glu Leu Glu Gln Asn Gly Asn His
465                 470                 475                 480
```

<210> SEQ ID NO 11
<211> LENGTH: 1714
<212> TYPE: DNA
<213> ORGANISM: Arabidopsis thaliana

<400> SEQUENCE: 11

```
atagaaacac atcattaaca aaacaaagcc tctctaaata aaaacaaaaa gctaactgaa      60

taagaagaag tagtgatgca tatcacaaaa ccacacgccg ccatgttttc cagtcccgga     120

atgggccatg tcatcccggt gatcgagctt ggaaagcgtc tctccgctaa caacggcttc     180

cacgtcaccg tcttcgtcct cgaaaccgac gcagcctccg ctcaatccaa gttcctaaac     240

tcaaccggcg tcgacatcgt caaacttcca tcgccggaca tttatggttt agtggacccc     300

gacgaccatg tagtgaccaa gatcggagtc attatgcgtg cagcagttcc agccctccga     360

tccaagatcg ctgccatgca tcaaaagcca acggctctga tcgttgactt gtttggcaca     420
```

-continued

```
gatgcgttat gtctcgcaaa ggaatttaac atgttgagtt atgtgtttat ccctaccaac    480

gcacgttttc tcggagtttc gatttattat ccaaatttgg acaaagatat caaggaagag    540

cacacagtgc aaagaaaccc actcgctata ccggggtgtg aaccggttag gttcgaagat    600

actctggatg catatctggt tcccgacgaa ccggtgtacc gggattttgt tcgtcatggt    660

ctggcttacc caaaagccga tggaatttg gtaaatacat gggaagagat ggagcccaaa    720

tcattgaagt cccttctaaa cccaaagctc ttgggccggg ttgctcgtgt accggtctat    780

ccaatcggtc ccttatgcag accgatacaa tcatccgaaa ccgatcaccc ggttttggat    840

tggttaaacg aacaaccgaa cgagtcggtt ctctatatct ccttcgggag tggtggttgt    900

ctatcggcga aacagttaac tgaattggcg tggggactcg agcagagcca gcaacggttc    960

gtatgggtgg ttcgaccacc ggtcgacggt tcgtgttgta gcgagtatgt ctcggctaac   1020

ggtggtggaa ccgaagacaa cacgccagag tatctaccgg aagggttcgt gagtcgtact   1080

agtgatagag gtttcgtggt cccctcatgg gccccacaag ctgaaatcct gtcccatcgg   1140

gccgttggtg ggtttttgac ccattgcggt tggagctcga cgttggaaag cgtcgttggc   1200

ggcgttccga tgatcgcatg gccacttttt gccgagcaga atatgaatgc ggcgttgctc   1260

agcgacgaac tgggaatcgc agtcagattg gatgatccaa aggaggatat ttctaggtgg   1320

aagattgagg cgttggtgag gaaggttatg actgagaagg aaggtgaagc gatgagaagg   1380

aaagtgaaga agttgagaga ctcggcggag atgtcactga gcattgacgg tggtggtttg   1440

gcgcacgagt cgctttgcag agtcaccaag gagtgtcaac ggtttttgga acgtgtcgtg   1500

gacttgtcac gtggtgctta gaaattgtta ccgttttcta gctcttttat tattagtggt   1560

tgaattatac gtgtcgttcc tctgttagtg tataatataa taatcgattt actctttgta   1620

atataatgat gtttttgata tttttcaact aattttccat tgtaatattg aataatcggg   1680

tgttgttgta attaataatg agaaacaatt tgtt                               1714


<210> SEQ ID NO 12
<211> LENGTH: 1858
<212> TYPE: DNA
<213> ORGANISM: Arabidopsis thaliana

<400> SEQUENCE: 12

aatgattcac acaaactctc tatataaagc cattacttaa taccacacaa attacaaaaa     60

aaaaaagaaa aaaggagata ataatcacaa actacaaaag tagaaagaag aaaaaagaac    120

aaagtatcag ttcttgaata tttgcatcaa tggaggaatc caaaacacct cacgttgcga    180

tcataccaag tccgggaatg ggtcatctca taccactcgt cgagtttgct aaacgactcg    240

tccatcttca cggcctcacc gttaccttcg tcatcgccgg cgaaggtcca ccatcaaaag    300

ctcagagaac cgtcctcgac tctctccctt cttcaatctc ctccgtcttt ctccctcctg    360

ttgatctcac cgatctctct tcgtccactc gcatcgaatc tcggatctcc ctcaccgtga    420

ctcgttcaaa cccggagctc cggaaagtct tcgactcgtt cgtggaggga ggtcgtttgc    480

caacggcgct cgtcgtcgat ctcttcggta cggacgcttt cgacgtggcc gtagaatttc    540

acgtgccacc gtatattttc tacccaacaa cggccaacgt cttgtcgttt tttctccatt    600

tgcctaaact agacgaaacg gtgtcgtgtg agttcaggga attaaccgaa ccgcttatgc    660

ttcctggatg tgtaccggtt gccgggaaag atttccttga cccggcccaa gaccggaaag    720

acgatgcata caaatggctt ctccataaca ccaagaggta caaagaagcc gaaggtattc    780

ttgtgaatac cttctttgag ctagagccaa atgctataaa ggccttgcaa gaaccgggtc    840
```

```
ttgataaacc accggtttat ccggttggac cgttggttaa cattggtaag caagaggcta    900

agcaaaccga agagtctgaa tgtttaaagt ggttggataa ccagccgctc ggttcggttt    960

tatatgtgtc ctttggtagt ggcggtaccc tcacatgtga gcagctcaat gagcttgctc   1020

ttggtcttgc agatagtgag caacggtttc tttgggtcat acgaagtcct agtgggatcg   1080

ctaattcgtc gtattttgat tcacatagcc aaacagatcc attgacattt ttaccaccgg   1140

gatttttaga gcggactaaa aaaagaggtt ttgtgatccc tttttgggct ccacaagccc   1200

aagtcttggc gcatccatcc acgggaggat ttttaactca ttgtggatgg aattcgactc   1260

tagagagtgt agtaagcggt attccactta tagcatggcc attatacgca gaacagaaga   1320

tgaatgcggt tttgttgagt gaagatattc gtgcggcact taggccgcgt gccggggacg   1380

atgggttagt tagaagagaa gaggtggcta gagtggtaaa aggattgatg gaaggtgaag   1440

aaggcaaagg agtgaggaac aagatgaagg agttgaagga agcagcttgt agggtgttga   1500

aggatgatgg gacttcgaca aaagcactta gtcttgtggc cttaaagtgg aaagcccaca   1560

aaaaagagtt agagcaaaat ggcaaccact aaatatttga tgttctaata tgatttgtat   1620

aatcaacggt gggatttgtg caaatgtgtt tctgtatgta tatgtatgtt ctacttttct   1680

ttgcttcgtt tgtctcaact tttatttgta tatgtttttg gcttttgatt aattcgtaga   1740

agatgttgca attaagatca gcttagaaga agatgttgca tatatagtta aatattgttc   1800

aagagaatca tcaattgtct atcgtcaata gttaaatata tatatggctt ataaaaat     1858
```

<210> SEQ ID NO 13
<211> LENGTH: 367
<212> TYPE: PRT
<213> ORGANISM: Podospora anserina

<400> SEQUENCE: 13

```
Met Pro Ser Lys Leu Ala Ile Thr Ser Met Ser Leu Gly Arg Cys Tyr
1               5                   10                  15

Ala Gly His Ser Phe Thr Thr Lys Leu Asp Met Ala Arg Lys Tyr Gly
            20                  25                  30

Tyr Gln Gly Leu Glu Leu Phe His Glu Asp Leu Ala Asp Val Ala Tyr
        35                  40                  45

Arg Leu Ser Gly Glu Thr Pro Ser Pro Cys Gly Pro Ser Pro Ala Ala
    50                  55                  60

Gln Leu Ser Ala Ala Arg Gln Ile Leu Arg Met Cys Gln Val Arg Asn
65                  70                  75                  80

Ile Glu Ile Val Cys Leu Gln Pro Phe Ser Gln Tyr Asp Gly Leu Leu
                85                  90                  95

Asp Arg Glu Glu His Glu Arg Arg Leu Glu Gln Leu Glu Phe Trp Ile
            100                 105                 110

Glu Leu Ala His Glu Leu Asp Thr Asp Ile Ile Gln Ile Pro Ala Asn
        115                 120                 125

Phe Leu Pro Ala Glu Glu Val Thr Glu Asp Ile Ser Leu Ile Val Ser
    130                 135                 140

Asp Leu Gln Glu Val Ala Asp Met Gly Leu Gln Ala Asn Pro Pro Ile
145                 150                 155                 160

Arg Phe Val Tyr Glu Ala Leu Cys Trp Ser Thr Arg Val Asp Thr Trp
                165                 170                 175

Glu Arg Ser Trp Glu Val Val Gln Arg Val Asn Arg Pro Asn Phe Gly
            180                 185                 190
```

-continued

Val Cys Leu Asp Thr Phe Asn Ile Ala Gly Arg Val Tyr Ala Asp Pro
195 200 205

Thr Val Ala Ser Gly Arg Thr Pro Asn Ala Glu Glu Ala Ile Arg Lys
210 215 220

Ser Ile Ala Arg Leu Val Glu Arg Val Asp Val Ser Lys Val Phe Tyr
225 230 235 240

Val Gln Val Val Asp Ala Glu Lys Leu Lys Lys Pro Leu Val Pro Gly
245 250 255

His Arg Phe Tyr Asp Pro Glu Gln Pro Ala Arg Met Ser Trp Ser Arg
260 265 270

Asn Cys Arg Leu Phe Tyr Gly Glu Lys Asp Arg Gly Ala Tyr Leu Pro
275 280 285

Val Lys Glu Ile Ala Trp Ala Phe Phe Asn Gly Leu Gly Phe Glu Gly
290 295 300

Trp Val Ser Leu Glu Leu Phe Asn Arg Arg Met Ser Asp Thr Gly Phe
305 310 315 320

Gly Val Pro Glu Glu Leu Ala Arg Arg Gly Ala Val Ser Trp Ala Lys
325 330 335

Leu Val Arg Asp Met Lys Ile Thr Val Asp Ser Pro Thr Gln Gln Gln
340 345 350

Ala Thr Gln Gln Pro Ile Arg Met Leu Ser Leu Ser Ala Ala Leu
355 360 365

<210> SEQ ID NO 14
<211> LENGTH: 345
<212> TYPE: PRT
<213> ORGANISM: Ustilago maydis

<400> SEQUENCE: 14

Met Ser Ser Ile Ala Ser Thr Ser Ala Ser Thr Met Gln His Pro Arg
1 5 10 15

Tyr Ser Ile Phe Thr His Ser Val Gly Tyr His Thr Ser Lys His Gly
20 25 30

Leu Leu Ser Lys Leu Asp Ala Ile Ser Ala Ala Gly Leu Ala Gly Val
35 40 45

Glu Met Phe Thr Asp Asp Leu Trp Ser Phe Ala Gln Ser Asp Glu Phe
50 55 60

Gly Ser Ile Leu Ala Ala Ser Glu Arg Glu Thr Glu Leu Leu Thr Pro
65 70 75 80

Pro Asp Ser Pro Leu Ser Gln Pro Ala Ser Leu Arg Asn Lys Thr Arg
85 90 95

Ile His Glu Asn Ala Glu Arg Ala Gly Gln His Tyr Ser Ala His Gly
100 105 110

Ala Cys Thr Pro Asp Glu Arg Gln Arg Glu Ile Ala Ala Ala Thr Phe
115 120 125

Ile Arg Ser Tyr Cys Ala Ser Arg Arg Leu Gln Val Glu Cys Leu Gln
130 135 140

Pro Leu Arg Asp Val Glu Gly Trp Leu Lys Asp Glu Asp Arg Glu Asn
145 150 155 160

Ala Ile Glu Arg Val Lys Ser Arg Phe Asp Ile Met Arg Ala Leu Asp
165 170 175

Thr His Leu Leu Leu Ile Cys Ser Gln Asn Thr Arg Ala Pro Gln Thr
180 185 190

Thr Gly Asp Met Ala Thr Ile Val Arg Asp Leu Thr His Ile Ser Asp
195 200 205

```
Leu Ala Ala Ala Tyr Thr Ala Gln Thr Gly Phe Glu Ile Lys Ile Gly
    210                 215                 220

Tyr Glu Ala Leu Ser Trp Gly Ala His Ile Asp Leu Trp Ser Gln Ala
225                 230                 235                 240

Trp Asn Ile Val Arg Thr Val Asp Arg Asp Asn Ile Gly Leu Ile Leu
                245                 250                 255

Asp Ser Phe Asn Thr Leu Ala Arg Glu Phe Ala Asp Pro Cys Thr Arg
            260                 265                 270

Ser Gly Ile Gln Glu Pro Ile Cys Thr Thr Leu Thr Ser Leu His Ser
        275                 280                 285

Ser Leu Gln Ala Ile Gln Ser Val Pro Ala Asp Lys Ile Phe Leu Leu
    290                 295                 300

Gln Ile Gly Asp Ala Arg Arg Leu Pro Glu Pro Leu Val Pro Ser Pro
305                 310                 315                 320

Arg Asp Gly Glu Pro Arg Pro Ser Arg Met Ile Trp Ser Arg Ser Ser
                325                 330                 335

Arg Leu Met Pro Ser Ser Lys Ala Ser
            340                 345


<210> SEQ ID NO 15
<211> LENGTH: 486
<212> TYPE: PRT
<213> ORGANISM: Acinetobacter sp.

<400> SEQUENCE: 15

Met Lys Leu Thr Ser Leu Arg Val Ser Leu Leu Ala Leu Gly Leu Val
1               5                   10                  15

Thr Ser Gly Phe Ala Ala Ala Glu Thr Tyr Thr Val Asp Arg Tyr Gln
            20                  25                  30

Asp Asp Ser Glu Lys Gly Ser Leu Arg Trp Ala Ile Glu Gln Ser Asn
        35                  40                  45

Ala Asn Ser Ala Gln Glu Asn Gln Ile Leu Ile Gln Ala Val Gly Lys
    50                  55                  60

Ala Pro Tyr Val Ile Lys Val Asp Lys Pro Leu Pro Pro Ile Lys Ser
65                  70                  75                  80

Ser Val Lys Ile Ile Gly Thr Glu Trp Asp Lys Thr Gly Glu Phe Ile
                85                  90                  95

Ala Ile Asp Gly Ser Asn Tyr Ile Lys Gly Glu Gly Glu Lys Ala Cys
            100                 105                 110

Pro Gly Ala Asn Pro Gly Gln Tyr Gly Thr Asn Val Arg Thr Met Thr
        115                 120                 125

Leu Pro Gly Leu Val Leu Gln Asp Val Asn Gly Val Thr Leu Lys Gly
    130                 135                 140

Leu Asp Val His Arg Phe Cys Ile Gly Val Leu Val Asn Arg Ser Ser
145                 150                 155                 160

Asn Asn Leu Ile Gln His Asn Arg Ile Ser Asn Asn Tyr Gly Gly Ala
                165                 170                 175

Gly Val Met Ile Thr Gly Asp Asp Gly Lys Gly Asn Pro Thr Ser Thr
            180                 185                 190

Thr Thr Asn Asn Asn Lys Val Leu Asp Asn Val Phe Ile Asp Asn Gly
        195                 200                 205

Asp Gly Leu Glu Leu Thr Arg Gly Ala Ala Phe Asn Leu Ile Ala Asn
    210                 215                 220

Asn Leu Phe Thr Ser Thr Lys Ala Asn Pro Glu Pro Ser Gln Gly Ile
```

-continued

```
225                 230                 235                 240

Glu Ile Leu Trp Gly Asn Asp Asn Ala Val Val Gly Asn Lys Phe Glu
                245                 250                 255

Asn Tyr Ser Asp Gly Leu Gln Ile Asn Trp Gly Lys Arg Asn Tyr Ile
            260                 265                 270

Ala Tyr Asn Glu Leu Thr Asn Asn Ser Leu Gly Phe Asn Leu Thr Gly
        275                 280                 285

Asp Gly Asn Ile Phe Asp Ser Asn Lys Val His Gly Asn Arg Ile Gly
    290                 295                 300

Ile Ala Ile Arg Ser Glu Lys Asp Ala Asn Ala Arg Ile Thr Leu Thr
305                 310                 315                 320

Lys Asn Gln Ile Trp Asp Asn Gly Lys Asp Ile Lys Arg Cys Glu Ala
                325                 330                 335

Gly Gly Ser Cys Val Pro Asn Gln Arg Leu Gly Ala Ile Val Phe Gly
            340                 345                 350

Val Pro Ala Leu Glu His Glu Gly Phe Val Gly Ser Arg Gly Gly Gly
        355                 360                 365

Val Val Ile Glu Pro Ala Lys Leu Gln Lys Thr Cys Thr Gln Pro Asn
    370                 375                 380

Gln Gln Asn Cys Asn Ala Ile Pro Asn Gln Gly Ile Gln Ala Pro Lys
385                 390                 395                 400

Leu Thr Val Ser Lys Lys Gln Leu Thr Val Glu Val Lys Gly Thr Pro
                405                 410                 415

Asn Gln Arg Tyr Asn Val Glu Phe Phe Gly Asn Arg Asn Ala Ser Ser
            420                 425                 430

Ser Glu Ala Glu Gln Tyr Leu Gly Ser Ile Val Val Val Thr Asp His
        435                 440                 445

Gln Gly Leu Ala Lys Ala Asn Trp Ala Pro Lys Val Ser Met Pro Ser
    450                 455                 460

Val Thr Ala Asn Val Thr Asp His Leu Gly Ala Thr Ser Glu Leu Ser
465                 470                 475                 480

Ser Ala Val Lys Met Arg
                485


<210> SEQ ID NO 16
<211> LENGTH: 371
<212> TYPE: PRT
<213> ORGANISM: Aspergillus niger

<400> SEQUENCE: 16

Met Pro Asn Arg Leu Gly Ile Ala Ser Met Ser Leu Gly Arg Pro Gly
1               5                   10                  15

Ile His Ser Leu Pro Trp Lys Leu His Glu Ala Ala Arg His Gly Tyr
            20                  25                  30

Ser Gly Ile Glu Leu Phe Phe Asp Asp Leu Asp His Tyr Ala Thr Thr
        35                  40                  45

His Phe Asn Gly Ser His Ile Ala Ala Ala His Ala Val His Ala Leu
    50                  55                  60

Cys Thr Thr Leu Asn Leu Thr Ile Ile Cys Leu Gln Pro Phe Ser Phe
65                  70                  75                  80

Tyr Glu Gly Leu Val Asp Arg Lys Gln Thr Glu Tyr Leu Leu Thr Val
                85                  90                  95

Lys Leu Pro Thr Trp Phe Gln Leu Ala Arg Ile Leu Asp Thr Asp Met
            100                 105                 110
```

-continued

```
Ile Gln Val Pro Ser Asn Phe Ala Pro Ala Gln Gln Thr Thr Gly Asp
        115                 120                 125

Arg Asp Val Ile Val Gly Asp Leu Gln Arg Leu Ala Asp Ile Gly Leu
    130                 135                 140

Ala Gln Ser Pro Pro Phe Arg Phe Val Tyr Glu Ala Leu Ala Trp Gly
145                 150                 155                 160

Thr Arg Val Asn Leu Trp Asp Glu Ala Tyr Glu Ile Val Glu Ala Val
                165                 170                 175

Asp Arg Pro Asn Phe Gly Ile Cys Leu Asp Thr Phe Asn Leu Ala Gly
            180                 185                 190

Arg Val Tyr Ala His Pro Gly Arg Gln Asp Gly Lys Thr Val Asn Ala
        195                 200                 205

Glu Ala Asp Leu Ala Ala Ser Leu Lys Lys Leu Arg Glu Thr Val Asp
    210                 215                 220

Val Lys Lys Val Phe Tyr Val Gln Val Val Asp Gly Glu Arg Leu Glu
225                 230                 235                 240

Arg Pro Leu Asp Glu Thr His Pro Phe His Val Glu Gly Gln Pro Val
                245                 250                 255

Arg Met Asn Trp Ser Arg Asn Ala Arg Leu Phe Ala Phe Glu Glu Asp
            260                 265                 270

Arg Gly Gly Tyr Leu Pro Ile Glu Glu Thr Ala Arg Ala Phe Phe Asp
        275                 280                 285

Thr Gly Phe Glu Gly Trp Val Ser Leu Glu Leu Phe Ser Arg Thr Leu
    290                 295                 300

Ala Glu Lys Gly Thr Gly Val Val Thr Glu His Ala Arg Arg Gly Leu
305                 310                 315                 320

Glu Ser Trp Lys Glu Leu Cys Arg Arg Leu Glu Phe Lys Gly Ala Glu
                325                 330                 335

Pro Gly Leu Asp Phe Val Pro Gly Glu Val Lys Val Gln Ser Val Ala
            340                 345                 350

Val Gly Ser Gly Lys Gly Val Glu Gln Glu Glu Met Gly Val Val Gln
        355                 360                 365

His Arg Leu
    370
```

<210> SEQ ID NO 17
<211> LENGTH: 1116
<212> TYPE: DNA
<213> ORGANISM: Aspergillus niger

<400> SEQUENCE: 17

```
atgcccaacc gtctcggcat cgcctccatg tcccttggac gcccaggcat ccactccctc      60

ccctggaagc tccacgaagc cgcccgccac ggctacagcg ggatcgagct cttcttcgac     120

gacctggacc actacgcaac cacccacttc aatggcagcc acatcgcggc tgctcacgcc     180

gtgcacgctc tctgcacgac cctcaacctc accatcatct gcctgcaacc cttctccttc     240

tacgaggggc tcgtcgaccg caagcaaacc gagtatctat tgaccgtgaa gctgcccaca     300

tggttccagc tcgctcgcat cctcgacacc gacatgatcc aggtgccctc gaacttcgcg     360

cccgcccagc aaaccacggg tgaccgggac gtgatcgtcg gcgacctcca gcgcctcgca     420

gacatcggcc tggcacagtc ccccaccctc cgcttcgtat acgaagcact ggcctggggc     480

acgcgggtga acctgtggga cgaggcgtac gagatcgtcg aggccgtgga ccgtcccaac     540

ttcggtatct gtcttgatac gtttaacctt gcgggtcggg tgtatgcgca ccctggtcgg     600
```

```
caggacggga agacggtcaa cgcggaggcg gatctggctg cgtcgttgaa gaagttgcgc    660

gagacggtgg atgtcaagaa ggtgttctac gtgcaggttg tggatggaga gaggctggag    720

aggccgttgg atgagaccca tccgtttcat gtggaggggc agccggtgcg gatgaactgg    780

agtcgcaatg cgaggttgtt tgcgtttgag gaggatcgcg gcgggtattt gcccattgag    840

gagaccgcga gggcgttctt tgatacgggg ttcgagggct gggtgtcgtt ggagttgttt    900

agtcgcacgt tggcggagaa gggcacgggg gtggtcacgg agcatgcgag acgcgggttg    960

gagtcgtgga aggagttgtg taggaggttg gagtttaagg gggcggagcc gggactggat   1020

tttgttcctg gggaggtgaa ggtgcagtcg gttgctgtgg ggagtgggaa gggggtggaa   1080

caggaggaga tgggggttgt gcagcatcgg ttgtag                             1116
```

```
<210> SEQ ID NO 18
<211> LENGTH: 1174
<212> TYPE: PRT
<213> ORGANISM: Nocardia iowensis

<400> SEQUENCE: 18

Met Ala Val Asp Ser Pro Asp Glu Arg Leu Gln Arg Arg Ile Ala Gln
1               5                   10                  15

Leu Phe Ala Glu Asp Glu Gln Val Lys Ala Ala Arg Pro Leu Glu Ala
            20                  25                  30

Val Ser Ala Ala Val Ser Ala Pro Gly Met Arg Leu Ala Gln Ile Ala
        35                  40                  45

Ala Thr Val Met Ala Gly Tyr Ala Asp Arg Pro Ala Ala Gly Gln Arg
    50                  55                  60

Ala Phe Glu Leu Asn Thr Asp Asp Ala Thr Gly Arg Thr Ser Leu Arg
65                  70                  75                  80

Leu Leu Pro Arg Phe Glu Thr Ile Thr Tyr Arg Glu Leu Trp Gln Arg
                85                  90                  95

Val Gly Glu Val Ala Ala Ala Trp His His Asp Pro Glu Asn Pro Leu
            100                 105                 110

Arg Ala Gly Asp Phe Val Ala Leu Leu Gly Phe Thr Ser Ile Asp Tyr
        115                 120                 125

Ala Thr Leu Asp Leu Ala Asp Ile His Leu Gly Ala Val Thr Val Pro
    130                 135                 140

Leu Gln Ala Ser Ala Ala Val Ser Gln Leu Ile Ala Ile Leu Thr Glu
145                 150                 155                 160

Thr Ser Pro Arg Leu Leu Ala Ser Thr Pro Glu His Leu Asp Ala Ala
                165                 170                 175

Val Glu Cys Leu Leu Ala Gly Thr Thr Pro Glu Arg Leu Val Val Phe
            180                 185                 190

Asp Tyr His Pro Glu Asp Asp Asp Gln Arg Ala Ala Phe Glu Ser Ala
        195                 200                 205

Arg Arg Arg Leu Ala Asp Ala Gly Ser Leu Val Ile Val Glu Thr Leu
    210                 215                 220

Asp Ala Val Arg Ala Arg Gly Arg Asp Leu Pro Ala Ala Pro Leu Phe
225                 230                 235                 240

Val Pro Asp Thr Asp Asp Asp Pro Leu Ala Leu Leu Ile Tyr Thr Ser
                245                 250                 255

Gly Ser Thr Gly Thr Pro Lys Gly Ala Met Tyr Thr Asn Arg Leu Ala
            260                 265                 270

Ala Thr Met Trp Gln Gly Asn Ser Met Leu Gln Gly Asn Ser Gln Arg
        275                 280                 285
```

-continued

```
Val Gly Ile Asn Leu Asn Tyr Met Pro Met Ser His Ile Ala Gly Arg
    290                 295                 300

Ile Ser Leu Phe Gly Val Leu Ala Arg Gly Gly Thr Ala Tyr Phe Ala
305                 310                 315                 320

Ala Lys Ser Asp Met Ser Thr Leu Phe Glu Asp Ile Gly Leu Val Arg
                325                 330                 335

Pro Thr Glu Ile Phe Phe Val Pro Arg Val Cys Asp Met Val Phe Gln
            340                 345                 350

Arg Tyr Gln Ser Glu Leu Asp Arg Arg Ser Val Ala Gly Ala Asp Leu
        355                 360                 365

Asp Thr Leu Asp Arg Glu Val Lys Ala Asp Leu Arg Gln Asn Tyr Leu
    370                 375                 380

Gly Gly Arg Phe Leu Val Ala Val Val Gly Ser Ala Pro Leu Ala Ala
385                 390                 395                 400

Glu Met Lys Thr Phe Met Glu Ser Val Leu Asp Leu Pro Leu His Asp
                405                 410                 415

Gly Tyr Gly Ser Thr Glu Ala Gly Ala Ser Val Leu Leu Asp Asn Gln
            420                 425                 430

Ile Gln Arg Pro Pro Val Leu Asp Tyr Lys Leu Val Asp Val Pro Glu
        435                 440                 445

Leu Gly Tyr Phe Arg Thr Asp Arg Pro His Pro Arg Gly Glu Leu Leu
    450                 455                 460

Leu Lys Ala Glu Thr Thr Ile Pro Gly Tyr Tyr Lys Arg Pro Glu Val
465                 470                 475                 480

Thr Ala Glu Ile Phe Asp Glu Asp Gly Phe Tyr Lys Thr Gly Asp Ile
                485                 490                 495

Val Ala Glu Leu Glu His Asp Arg Leu Val Tyr Val Asp Arg Arg Asn
            500                 505                 510

Asn Val Leu Lys Leu Ser Gln Gly Glu Phe Val Thr Val Ala His Leu
        515                 520                 525

Glu Ala Val Phe Ala Ser Ser Pro Leu Ile Arg Gln Ile Phe Ile Tyr
    530                 535                 540

Gly Ser Ser Glu Arg Ser Tyr Leu Leu Ala Val Ile Val Pro Thr Asp
545                 550                 555                 560

Asp Ala Leu Arg Gly Arg Asp Thr Ala Thr Leu Lys Ser Ala Leu Ala
                565                 570                 575

Glu Ser Ile Gln Arg Ile Ala Lys Asp Ala Asn Leu Gln Pro Tyr Glu
            580                 585                 590

Ile Pro Arg Asp Phe Leu Ile Glu Thr Glu Pro Phe Thr Ile Ala Asn
        595                 600                 605

Gly Leu Leu Ser Gly Ile Ala Lys Leu Leu Arg Pro Asn Leu Lys Glu
    610                 615                 620

Arg Tyr Gly Ala Gln Leu Glu Gln Met Tyr Thr Asp Leu Ala Thr Gly
625                 630                 635                 640

Gln Ala Asp Glu Leu Leu Ala Leu Arg Arg Glu Ala Ala Asp Leu Pro
                645                 650                 655

Val Leu Glu Thr Val Ser Arg Ala Ala Lys Ala Met Leu Gly Val Ala
            660                 665                 670

Ser Ala Asp Met Arg Pro Asp Ala His Phe Thr Asp Leu Gly Gly Asp
        675                 680                 685

Ser Leu Ser Ala Leu Ser Phe Ser Asn Leu Leu His Glu Ile Phe Gly
    690                 695                 700
```

-continued

```
Val Glu Val Pro Val Gly Val Val Val Ser Pro Ala Asn Glu Leu Arg
705                 710                 715                 720

Asp Leu Ala Asn Tyr Ile Glu Ala Glu Arg Asn Ser Gly Ala Lys Arg
                725                 730                 735

Pro Thr Phe Thr Ser Val His Gly Gly Gly Ser Glu Ile Arg Ala Ala
            740                 745                 750

Asp Leu Thr Leu Asp Lys Phe Ile Asp Ala Arg Thr Leu Ala Ala Ala
        755                 760                 765

Asp Ser Ile Pro His Ala Pro Val Pro Ala Gln Thr Val Leu Leu Thr
    770                 775                 780

Gly Ala Asn Gly Tyr Leu Gly Arg Phe Leu Cys Leu Glu Trp Leu Glu
785                 790                 795                 800

Arg Leu Asp Lys Thr Gly Gly Thr Leu Ile Cys Val Val Arg Gly Ser
                805                 810                 815

Asp Ala Ala Ala Ala Arg Lys Arg Leu Asp Ser Ala Phe Asp Ser Gly
            820                 825                 830

Asp Pro Gly Leu Leu Glu His Tyr Gln Gln Leu Ala Ala Arg Thr Leu
        835                 840                 845

Glu Val Leu Ala Gly Asp Ile Gly Asp Pro Asn Leu Gly Leu Asp Asp
    850                 855                 860

Ala Thr Trp Gln Arg Leu Ala Glu Thr Val Asp Leu Ile Val His Pro
865                 870                 875                 880

Ala Ala Leu Val Asn His Val Leu Pro Tyr Thr Gln Leu Phe Gly Pro
                885                 890                 895

Asn Val Val Gly Thr Ala Glu Ile Val Arg Leu Ala Ile Thr Ala Arg
            900                 905                 910

Arg Lys Pro Val Thr Tyr Leu Ser Thr Val Gly Val Ala Asp Gln Val
        915                 920                 925

Asp Pro Ala Glu Tyr Gln Glu Asp Ser Asp Val Arg Glu Met Ser Ala
    930                 935                 940

Val Arg Val Val Arg Glu Ser Tyr Ala Asn Gly Tyr Gly Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Ser Asp Met Ile Leu Ala His Ser Arg Tyr
            980                 985                 990

Ala Gly Gln Leu Asn Val Gln Asp Val Phe Thr Arg Leu Ile Leu Ser
        995                 1000                1005

Leu Val Ala Thr Gly Ile Ala Pro Tyr Ser Phe Tyr Arg Thr Asp Ala
    1010                1015                1020

Asp Gly Asn Arg Gln Arg Ala His Tyr Asp Gly Leu Pro Ala Asp Phe
1025                1030                1035                1040

Thr Ala Ala Ala Ile Thr Ala Leu Gly Ile Gln Ala Thr Glu Gly Phe
                1045                1050                1055

Arg Thr Tyr Asp Val Leu Asn Pro Tyr Asp Asp Gly Ile Ser Leu Asp
            1060                1065                1070

Glu Phe Val Asp Trp Leu Val Glu Ser Gly His Pro Ile Gln Arg Ile
        1075                1080                1085

Thr Asp Tyr Ser Asp Trp Phe His Arg Phe Glu Thr Ala Ile Arg Ala
    1090                1095                1100

Leu Pro Glu Lys Gln Arg Gln Ala Ser Val Leu Pro Leu Leu Asp Ala
1105                1110                1115                1120

Tyr Arg Asn Pro Cys Pro Ala Val Arg Gly Ala Ile Leu Pro Ala Lys
```

```
                1125                1130                1135

Glu Phe Gln Ala Ala Val Gln Thr Ala Lys Ile Gly Pro Glu Gln Asp
            1140                1145                1150

Ile Pro His Leu Ser Ala Pro Leu Ile Asp Lys Tyr Val Ser Asp Leu
        1155                1160                1165

Glu Leu Leu Gln Leu Leu
    1170


<210> SEQ ID NO 19
<211> LENGTH: 209
<212> TYPE: PRT
<213> ORGANISM: Escherichia coli

<400> SEQUENCE: 19

Met Val Asp Met Lys Thr Thr His Thr Ser Leu Pro Phe Ala Gly His
1               5                   10                  15

Thr Leu His Phe Val Glu Phe Asp Pro Ala Asn Phe Cys Glu Gln Asp
            20                  25                  30

Leu Leu Trp Leu Pro His Tyr Ala Gln Leu Gln His Ala Gly Arg Lys
        35                  40                  45

Arg Lys Thr Glu His Leu Ala Gly Arg Ile Ala Ala Val Tyr Ala Leu
    50                  55                  60

Arg Glu Tyr Gly Tyr Lys Cys Val Pro Ala Ile Gly Glu Leu Arg Gln
65                  70                  75                  80

Pro Val Trp Pro Ala Glu Val Tyr Gly Ser Ile Ser His Cys Gly Thr
                85                  90                  95

Thr Ala Leu Ala Val Val Ser Arg Gln Pro Ile Gly Ile Asp Ile Glu
            100                 105                 110

Glu Ile Phe Ser Val Gln Thr Ala Arg Glu Leu Thr Asp Asn Ile Ile
        115                 120                 125

Thr Pro Ala Glu His Glu Arg Leu Ala Asp Cys Gly Leu Ala Phe Ser
    130                 135                 140

Leu Ala Leu Thr Leu Ala Phe Ser Ala Lys Glu Ser Ala Phe Lys Ala
145                 150                 155                 160

Ser Glu Ile Gln Thr Asp Ala Gly Phe Leu Asp Tyr Gln Ile Ile Ser
                165                 170                 175

Trp Asn Lys Gln Gln Val Ile Ile His Arg Glu Asn Glu Met Phe Ala
            180                 185                 190

Val His Trp Gln Ile Lys Glu Lys Ile Val Ile Thr Leu Cys Gln His
        195                 200                 205

Asp


<210> SEQ ID NO 20
<211> LENGTH: 500
<212> TYPE: PRT
<213> ORGANISM: Saccharomyces cerevisiae

<400> SEQUENCE: 20

Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Thr Glu Asp
    50                  55                  60
```

```
Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Gly Val Lys Gln Ser Gly Tyr Gly Arg
465                 470                 475                 480
```

-continued

```
Glu Met Gly Glu Glu Val Tyr His Ala Tyr Thr Glu Val Lys Ala Val
                485                 490                 495

Arg Ile Lys Leu
            500


<210> SEQ ID NO 21
<211> LENGTH: 1503
<212> TYPE: DNA
<213> ORGANISM: Saccharomyces cerevisiae

<400> SEQUENCE: 21

atgactaagc tacactttga cactgctgaa ccagtcaaga tcacacttcc aaatggtttg      60

acatacgagc aaccaaccgg tctattcatt aacaacaagt ttatgaaagc tcaagacggt     120

aagacctatc ccgtcgaaga tccttccact gaaaacaccg tttgtgaggt ctcttctgcc     180

accactgaag atgttgaata tgctatcgaa tgtgccgacc gtgctttcca cgacactgaa     240

tgggctaccc aagacccaag agaaagaggc cgtctactaa gtaagttggc tgacgaattg     300

gaaagccaaa ttgacttggt ttcttccatt gaagctttgg acaatggtaa aactttggcc     360

ttagcccgtg gggatgttac cattgcaatc aactgtctaa gagatgctgc tgcctatgcc     420

gacaaagtca acggtagaac aatcaacacc ggtgacggct acatgaactt caccacctta     480

gagccaatcg gtgtctgtgg tcaaattatt ccatggaact ttccaataat gatgttggct     540

tggaagatcg ccccagcatt ggccatgggt aacgtctgta tcttgaaacc cgctgctgtc     600

acacctttaa atgccctata ctttgcttct ttatgtaaga aggttggtat tccagctggt     660

gtcgtcaaca tcgttccagg tcctggtaga actgttggtg ctgctttgac caacgaccca     720

agaatcagaa agctggcttt taccggttct acagaagtcg gtaagagtgt tgctgtcgac     780

tcttctgaat ctaacttgaa gaaaatcact ttggaactag gtggtaagtc cgcccatttg     840

gtctttgacg atgctaacat taagaagact ttaccaaatc tagtaaacgg tattttcaag     900

aacgctggtc aaatttgttc ctctggttct agaatttacg ttcaagaagg tatttacgac     960

gaactattgg ctgctttcaa ggcttacttg gaaaccgaaa tcaaagttgg taatccattt    1020

gacaaggcta acttccaagg tgctatcact aaccgtcaac aattcgacac aattatgaac    1080

tacatcgata tcggtaagaa agaaggcgcc aagatcttaa ctggtggcga aaaagttggt    1140

gacaagggtt acttcatcag accaaccgtt ttctacgatg ttaatgaaga catgagaatt    1200

gttaaggaag aaatttttgg accagttgtc actgtcgcaa agttcaagac tttagaagaa    1260

ggtgtcgaaa tggctaacag ctctgaattc ggtctaggtt ctggtatcga aacagaatct    1320

ttgagcacag gtttgaaggt ggccaagatg ttgaaggccg gtaccgtctg gatcaacaca    1380

tacaacgatt ttgactccag agttccattc ggtggtgtta agcaatctgg ttacggtaga    1440

gaaatgggtg aagaagtcta ccatgcatac actgaagtaa aagctgtcag aattaagttg    1500

taa                                                                  1503


<210> SEQ ID NO 22
<211> LENGTH: 1098
<212> TYPE: DNA
<213> ORGANISM: Artificial Sequence
<220> FEATURE:
<223> OTHER INFORMATION: Synthetic Codon Optimized

<400> SEQUENCE: 22

atgggttcta ctggtgaaac tcaaattact ccaactcaca tttctgatga agaagctaac      60

ttgttcgcta tgcaattggc ttctgcttct gttttgccaa tgattttgaa gtctgctttg     120
```

gaattggatt tgttggaaat tattgctaag gctggtccag gtgctcaaat ttctccaatt 180
gaaattgctt ctcaattgcc aactactaac ccagatgctc cagttatgtt ggatagaatg 240
ttgagattgt tggcttgtta caacattttg acttgttctg ttagaactca acaagatggt 300
aaggttcaaa gattgtacgg tttggctact gttgctaagt acttggttaa gaacgaagat 360
ggtgtttcta tttctgcttt gaacttgatg aaccaagata aggttttgat ggaatcttgg 420
taccacttga aggatgctgt tttggatggt ggtattccat tcaacaaggc ttacggtatg 480
actgctttcg aataccacgg tactgatcca agattcaaca aggttttcaa caagggtatg 540
tctgatcact ctactattac tatgaagaag attttggaaa cttacactgg tttcgaaggt 600
ttgaagtctt tggttgatgt tggtggtggt actggtgctg ttattaacac tattgtttct 660
aagtacccaa ctattaaggg tattaacttc gatttgccac acgttattga agatgctcca 720
tcttacccag gtgttgaaca cgttggtggt gatatgttcg tttctattcc aaaggctgat 780
gctgttttca tgaagtggat ttgtcacgat tggtctgatg aacactgttt gaagttcttg 840
aagaactgtt acgaagcttt gccagataac ggtaaggtta ttgttgctga atgtattttg 900
ccagttgctc cagattcttc tttggctact aagggtgttg ttcacattga tgttattatg 960
ttggctcaca acccaggtgg taaggaaaga actcaaaagg aattcgaaga tttggctaag 1020
ggtgctggtt tccaaggttt caaggttcac tgtaacgctt tcaacactta cattatggaa 1080
ttcttgaaga aggtttga 1098

<210> SEQ ID NO 23
<211> LENGTH: 1098
<212> TYPE: DNA
<213> ORGANISM: Artificial Sequence
<220> FEATURE:
<223> OTHER INFORMATION: Synthetic Codon Optimized

<400> SEQUENCE: 23
atgggttcta ctggtgaaac tcaaatgact ccaactcaag tttctgatga agaagctaac 60
ttgttcgcta tgcaattggc ttctgcttct gttttgccaa tggttttgaa ggctgctatt 120
gaattggatt tgttggaaat tatggctaag gctggtccag gtgctttctt gtctccaaac 180
gatttggctt ctcaattgcc aactaagaac ccagaagctc cagttatgtt ggatagaatg 240
ttgagattgt tggcttctta ctctattttg acttactctt tgagaacttt gccagatggt 300
aaggttgaaa gattgtacgg tttgggtcca gtttgtaagt tcttgactaa gaacgaagat 360
ggtgtttcta ttgctgcttt gtgtttgatg aaccaagata aggttttggt tgaatcttgg 420
taccacttga aggatgctgt tttggatggt ggtattccat tcaacaaggc ttacggtatg 480
actgctttcg attaccacgg tactgatcca agattcaaca aggttttcaa caagggtatg 540
gctgatcact ctactattac tatgaagaag attttggaaa cttacaaggg tttcgaaggt 600
ttgacttcta ttgttgatgt tggtggtggt actggtgctg ttgttaacat gattgtttct 660
aagtacccat ctattaaggg tattaacttc gatttgccac acgttattga agatgctcca 720
caatacccag gtgttcaaca cgttggtggt gatatgttcg tttctgttcc aaagggtgat 780
gctattttca tgaagtggat ttgtcacgat tggtctgatg aacactgttt gaagttcttg 840
aagaactgtt acgctgcttt gccagataac ggtaaggtta ttttgggtga atgtattttg 900
ccagttgctc cagatacttc tttggctact aagggtgttg ttcacattga tgttattatg 960
ttggctcaca acccaggtgg taaggaaaga actggtcaag aattcgaagc tttggctaag 1020

-continued

```
ggttctggtt tccaaggtat tagagttgct tgtaacgctt tcaacactta cgttattgaa   1080

ttcttgaaga agatttaa                                                 1098


<210> SEQ ID NO 24
<211> LENGTH: 1098
<212> TYPE: DNA
<213> ORGANISM: Artificial Sequence
<220> FEATURE:
<223> OTHER INFORMATION: Synthetic Codon Optimized

<400> SEQUENCE: 24

atggctactt gggttgaaca ccaacaacaa caaaacggtt ctaaggatgt tgatgaagaa     60

gcttgtatgt acgctatgca attgtcttct atggttgttt tgccaatgac tttgagagtt    120

gctgttgaat tgggtatttt ggaacaaatt caagctggtg gtccagattc ttacttgact    180

gctgaagatt tggctgctag attgggtaac tctaacccat tggctccagt tatgattgaa    240

agaattttga gattgttgac ttcttactct attttgaact tcactgatac tgttgatggt    300

gaaggtagaa ctgttagatc ttacggtgct gctcacgttt gtaagtactt gactccaaac    360

caagatggtg tttctatggc tccattggtt ttgatgaaca ctgataaggt tttgatggaa    420

tcttggtacc acatgaagga tgctgttact aacggtggta ttccattcaa cttggcttac    480

ggtatgactg ctttcgaata ccacggtaag gatttgagat tcaacaaggt tttcaacgaa    540

ggtatgaaga acaactctat tattattact aagaagattt tggaaagata caagagattc    600

gaagatgtta acgttttgat tgatgttggt ggtggtattg gtggtactat ttctatgatt    660

actgctaagt acccacacat tcacggtatt aacttcgatt tgccacacgt tgtttctgaa    720

gctccaccat tccaaggtgt tgaacacgtt ggtggtaaca tgttcgaatc tgttccaatt    780

ggtgatgcta ttttcattaa gtggattttg cacgattggt ctgatgaaca ctgtttgaag    840

ttgttgagaa actgtgctaa gtctttgcca gataagggta aggttattgt tgttgaatgt    900

attttgccag atgctccatt ggttactcca gaagctgaag gtgttttcca cttggatatg    960

attatgttgg ctcacaaccc aggtggtaag gaaagaacta agaaggaatt caaggaattg   1020

gctatgttgt ctggtttctc taacttcaag gctttgttct cttacgctaa cgtttgggtt   1080

atggaattca acaagtga                                                 1098


<210> SEQ ID NO 25
<211> LENGTH: 816
<212> TYPE: DNA
<213> ORGANISM: Artificial Sequence
<220> FEATURE:
<223> OTHER INFORMATION: Synthetic Codon Optimized

<400> SEQUENCE: 25

atgccggagg ccccgcctct gctgttggca gctgtgttgc tgggcctggt gctgctggtg     60

gtgctgctgc tgcttctgag gcactggggc tggggcctgt gccttatcgg ctggaacgag    120

ttcatcctgc agcccatcca caacctgctc atgggtgaca ccaaggagca gcgcatcctg    180

aaccacgtgc tgcagcatgc ggagcccggg aacgcacaga gcgtgctgga ggccattgac    240

acctactgcg agcagaagga gtgggccatg aacgtgggcg acaagaaagg caagatcgtg    300

gacgccgtga ttcaggagca ccagccctcc gtgctgctgg agctgggggc ctactgtggc    360

tactcagctg tgcgcatggc ccgcctgctg tcaccagggg cgaggctcat caccatcgag    420

atcaaccccg actgtgccgc catcacccag cggatggtgg atttcgctgg cgtgaaggac    480

aaggtcaccc ttgtggttgg agcgtcccag gacatcatcc cccagctgaa gaagaagtat    540
```

-continued

```
gatgtggaca cactggacat ggtcttcctc gaccactgga aggaccggta cctgccggac    600

acgcttctct tggaggaatg tggcctgctg cggaagggga cagtgctact ggctgacaac    660

gtgatctgcc caggtgcgcc agacttccta gcacacgtgc gcgggagcag ctgctttgag    720

tgcacacact accaatcgtt cctggaatac agggaggtgg tggacggcct ggagaaggcc    780

atctacaagg gcccaggcag cgaagcaggg ccttaa                              816
```